United States Patent
Wadhwa et al.

(10) Patent No.: US 8,591,893 B2
(45) Date of Patent: Nov. 26, 2013

(54) PARATOPE AND EPITOPE OF ANTI-MORTALIN ANTIBODY

(75) Inventors: Renu Wadhwa, Ibaraki (JP); Sunil Kaul, Ibaraki (JP); Maki Shiota, Ibaraki (JP); Atsushi Inoue, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 680 days.

(21) Appl. No.: 12/602,358

(22) PCT Filed: May 28, 2008

(86) PCT No.: PCT/JP2008/059834
§ 371 (c)(1),
(2), (4) Date: Aug. 5, 2010

(87) PCT Pub. No.: WO2008/146854
PCT Pub. Date: Dec. 4, 2008

(65) Prior Publication Data
US 2010/0297664 A1 Nov. 25, 2010

(30) Foreign Application Priority Data

May 28, 2007 (JP) .................................. 2007-140943
Nov. 15, 2007 (JP) .................................. 2007-296405
Feb. 18, 2008 (JP) .................................. 2008-036343

(51) Int. Cl.
*A61K 39/00* (2006.01)
*A61K 39/395* (2006.01)

(52) U.S. Cl.
USPC .................. 424/133.1; 424/135.1; 424/138.1; 424/178.1

(58) Field of Classification Search
None
See application file for complete search history.

(56) References Cited

U.S. PATENT DOCUMENTS

| | | | |
|---|---|---|---|
| 7,179,892 B2 * | 2/2007 | Basi et al. ................... | 530/387.3 |
| 2007/0122414 A1 * | 5/2007 | Georges et al. ............ | 424/155.1 |
| 2008/0260739 A1 | 10/2008 | Wadhwa et al. | |

FOREIGN PATENT DOCUMENTS

| | | |
|---|---|---|
| AU | 16740/92 A1 | 12/1992 |
| JP | 8-500084 A | 1/1996 |
| JP | 11-502414 A | 3/1999 |
| JP | 2004-045433 A | 2/2004 |
| JP | 2005-500808 A | 1/2005 |
| JP | 2006-89471 A | 4/2006 |
| WO | WO 92/19759 A1 | 11/1992 |
| WO | 93/23062 A1 | 11/1993 |
| WO | WO 96/30400 | 10/1996 |
| WO | 02/46237 A2 | 6/2002 |

OTHER PUBLICATIONS

WO 2006/022344, Kaul et al, Feb. 3, 2006, abstract Only.*
Rudikoff et al (Proc Natl Acad Sci USA 1982 vol. 79 p. 1979).*
MacCallum et al. J. Mol. Biol. (1996) 262, 732-745.*
Pascalis et al. (The Journal of Immunology, 2002, 169: 3076-3084).*
Casset et al. (2003) BBRC 307, 198-205.*
Kofler et al (J Clinical Investigation, 1988, 82:852-860).*
HUGO Gene Nomenclature Committee, Gene Symbol Report for HSPA9, printed Feb. 2013.*
Domanico et al (Molecular and Cellular Biology, 1993, 13:3598-3610).*
Maki Shiota et al. "Internalizing Antibody-Based Targeted Gene Delivery for Human Cancer Cells." Human Gene Therapy, Nov. 2007, 18: pp. 1153-1160.
Zeenia Kaul et. al. "An antibody-conjugated internalizing quantum dot suitable for long-term live imaging of cells." Biochem. Cell Biol., Feb. 21, 2007, vol. 85: pp. 133-140.
Zeenia Kaul et. al. "Quantum dot-based Mortalin Staining as a Visual Assay for Detection of Induced Senescence in Cancer Cells." Ann. N.Y. Academy of Sciences. 2007, 1100: pp. 368-372.
Japanese Office Action dated Jan. 24, 2012 for corresponding Japanese patent application No. 2008-036343.
International Search Report issued Jul. 22, 2008, in PCT/JP2008/059834.
Ivan A. Bespalov et al., "Recombinant Phabs Reactive with 7,8-Dihydro-8-oxoguanine, a Major Oxidative DNA Lesion", Biochemistry, 1996, 35: 2067-2078.

* cited by examiner

*Primary Examiner* — Laura B Goddard
(74) *Attorney, Agent, or Firm* — Sughrue Mion, PLLC

(57) ABSTRACT

The amino acid sequences of paratope regions involved in internalizing function of an anti-mortalin antibody into tumor cells were determined for the L-chain and H-chain variable regions of cellular internalizing anti-mortalin antibodies and non-internalizing anti-mortalin antibodies. Cancer-cell-specific drug delivery is provided by using the mortalin-binding activity of a single-chain antibody (scFv) wherein L-chain and H-chain variable regions both having the paratope region are linked together via a peptide linker. Also, the sequence of 6 amino acids of an epitope to be recognized by an anti-mortalin antibody having the internalizing function was determined. With the use of an expression vector comprising a nucleic acid that encodes the epitope, an agent for accelerating internalization of a mortalin antibody, a drug bound thereto, and the like into cancer cells is provided.

5 Claims, 23 Drawing Sheets

FIG. 1

Light Chain

| L chain | signal sequence | FR1 | CDR1 | FR2 |
|---|---|---|---|---|
| 37-1(kappa) | MMSPAQFLFLLVLWIRETNG | DVVMTQTPLTLSVTIGQPASISC | KSSQSLLDSDGKTYLN | WLLQRPGQSPKRLIY |
| 37-6(kappa) | MMSPAQFLFLLVLWIRETNG | DVVMTQTPLTLSVTIGQPASISC | KSSQSLLDSDGKTYLN | WLLQRPGQSPKRLIY |
| 38-5(kappa) | MMSPAQFLFLLVLWIRETTG | DVVMTQTPLTLSVTIGQPASISC | KSSQSLLDSDGKTYLN | WLLQRPGQSPKRLIY |
| 96-5(kappa) | MMSPAQFLFLLVLWIRETNG | DVVMTQTPLTLSVTIGQPASISC | KSSQSLLDSDGKTYLN | WLLQRPGQSPKRLIY |
| 52-3(kappa) | MRFSAQLLGLLVLWIPGSTAE | KIVMTQAAFSNPVTLGTSASISC | RSSKSLLYSNGITYLY | WYLQKPGQSPQLLIY |
| 71-1(kappa) | MDMRVPAHVFGFLLLWFPGTRC | DIQMTQSPSSLSASLGERVSLTC | RASQEISGYLS | WLQQKPDGTIKRLIY |

| L chain | CDR2 | FR3 | CDR3 | FR4 |
|---|---|---|---|---|
| 37-1(kappa) | LVSKLDS | GVPDRFTGSGSGTDFTLKISRVEAEDLGVYYC | WQGTHFPRT | FGGGTKLEIK |
| 37-6(kappa) | LVSKLDS | GVPDRFTGSGSGTDFTLKISRVEAEDLGVYYC | WQGTHFPRT | FGGGTKLEIK |
| 38-5(kappa) | LVSKLDS | GVPDRFTGSGSGTDFTLKISRVESEDLGVYYC | WQGTHFPRT | FGGGTKLEIK |
| 96-5(kappa) | LVSKLDS | GVPDRFTGSGSGTDFTLKISRVEAEDLGVYYC | WQGTHFPRT | FGGGTKLEIK |
| 52-3(kappa) | QMSNLAS | GVPDRFSSSGSGTDFTLRISRVEAEDVGVYYC | AQNLELPWT | FGGGTKLEIK |
| 71-1(kappa) | AASTLDS | GVPKRFSGSRSGSDYSLTISSLESEDFADYYC | LQYASYPPT | FGGGTKLEIK |

Heavy Chain

| H chain | signal sequence | FR1 | CDR1 | FR2 |
|---|---|---|---|---|
| 37-1(IgG1) | MGWSCIILFLVSTATGVHS | QVQLQQPGAELVKPGASVKLSCKASGYTFT | SYWMH | WVKQRPGQGLEWIG |
| 37-6(IgG1) | MGWSCIILFLVSTATGVHS | QVQLQQPGAELVKPGASVKLSCKASGYTFT | SYWMH | WVKQRPGQGLEWIG |
| 38-5(IgG1) | MGWSCIILFLVSTATGVHS | QVQLQQPGAELVKPGASVKLSCKASGYTFT | SYWMH | WVKQRPGQGLEWIG |
| 96-5(IgG2b) | MGWSCIILFLVSTATGVHS | QVQLQQPGAELVKPGASVKLSCKASGYTFT | SYWMH | WVKQRPGQGLEWIG |
| 52-3(IgG2b) | MGWSYIILFLVATATDVHS | QVQLQQPGAELVKPGASVKLSCKASGYTFT | SYWMH | WVKQRPGQGLEWIG |
| 71-1(IgG3) | MLLGLKWVFFVVFYQGVHC | EVQLVETGGGLVQPKGSLKLSCAASGFTFN | TNAMN | WVRQAPGKGLEWVA |

| H chain | CDR2 | FR3 | CDR3 | FR4 |
|---|---|---|---|---|
| 37-1(IgG1) | EIDPSDSYTKYNQKFKG | KATLTVDKSSSTAYMQLSSLTSEDSAVYYCAR | GDY | WGQGTTLTVSS |
| 37-6(IgG1) | EIDPSDSYTKYNQKFKG | KATLTVDKSSSTAYMQLSSLTSEDSAVYYCAR | GDY | WGQGTTLTVSS |
| 38-5(IgG1) | EIDPSDSYTKYNQKFKG | KATLTVDKSSSTAYMQLSSLTSEDSAVYYCAR | GDY | WGQGTILRVSS |
| 96-5(IgG2b) | EIDPSDSYTDYNQNFKG | KATLTVDKSSSTAYMQLSSLTSEDSAVYYCAR | GDY | WGQGTTLTVSS |
| 52-3(IgG2b) | EINPSNGRTNYNEKFKS | KATLTVDKSSSTAYMQLSSLTSEDSAVYYCAR | SRYYGSCYFDY | WGQGTTLTVSS |
| 71-1(IgG3) | RIRSKSNNYATYYADSVKD | RFTISRDDSQSMLYLQMNNLKTEDTAMYCVR | DGYYSY | WGQGTLVTVSA | cDNA cloning and paratope characterization of mortalin antibodies

FIG. 2

IgG subtypes of mortalin antibodies

| Antibody Clone | cDNA Sequence | IgG Subclass | SEQ ID NO: |
|---|---|---|---|
| 37-1 | GGGCCAGTGGATAGACAGATG | IgG1 | 36 |
| 37-6 | GGGCCAGTGGATAGACAGATG | IgG1 | 36 |
| 38-4 | GGGCCAGTGGATAGACAGATG | IgG1 | 36 |
| 71-1 | CAGGGACCAAGGGATAGACAG | IgG3 | 39 |
| 96-5 | CAGGGGCCAGTGGATAGACTGATG | IgG2b | 40 |
| 52-3 | CAGGGGCCAGTGGATAGACTGATG | IgG2b | 40 |

ANTI-MORTALIN ANTIBODY

MONOCLONAL ANTIBODY 37-1 (37-6)

CONSTRUCTION OF scFv FLAGMENT

PRIMER 1 (36 mer)
CCATGACTACAAAGATGTTGTGATGACCCAGACTC (SEQ ID NO: 32)

PRIMER 2 (80 mer)
GGATCCCGAAGCAGCAGAACTAGTTCCCGAGCAGAACTACTGTTGCTCCGCCGTTGAGGCCGTTGATTTCCAGCTTGGTGC
(SEQ ID NO: 33)

PRIMER 3 (34 mer)
AGTTCTGCTTCGGGATCCCAGGTCCAACTGCAGC (SEQ ID NO: 34)

PRIMER 4 (31 mer)
TTGCTAGCAGATGAGGAGGACTGTGAGAGTGG (SEQ ID NO: 35)

```
                    T7 PROMOTER PRIMER #69348-3
                    ───────────▶
                    T7 PROMOTER                    LAC OPERATOR           Xba I                                                        rbs
Bgl II
AGATCTCGATCCCGCGAAATTAATACGACTCACTATAGGGGAATTGTGAGCGGATAACAATTCCCCTCTAGAAATAATTTTGTTTAACTTTAAGAAGGAGA
                    Nde I      BspM I         peIB LEADER    BseR I                                            Msc I Nco I    BamH I EcoR I   Sac I
TATACATATGAAATACCTGCTGCCGACCGCTGCTGGTCTGCTGCTGCTGCTGCCAGCCGGCTGGCCATGGCCGATGCCATGGCGATATCGAATTCGATCCGAATTAATTCGAATTCGAGCTCC
                    Me|LysTyrIleuLeuProThrA|aA|aG|yLeuLeuLeuLeuLeuA|aA|aG|yLeuLeuLeuLeuA|aA|aG|nProA|aMetA|aMetA|aMetAspI|eG|y I |eAsnSerAspProAsnSerSerSer
                    Eag I
Sal I Hind III  Not I           Nhe I                                         HSV·TAG               SIGNAL PEPTIDASE    His·TAG®
GTCGACAAGCTTGCGGCCGCACTGGAGATCAACGGGCTAGCCAGCGAGATCAAACCCGGAAGAACTCGCCCGAGAGATGTCGAGCAGCCACCACCACCACCACCACTGAGATCCGGCTG
Va|aAspLysLeuA|aA|aA|aLeuG|uI|eLysArgA|aSerG|nProG|uLeuA|aProG|uAspProG|uAspVa|G|uHisHisHisHisHisHisEnd
                    Bpu1102 I
CTAACAAAGCCCCAAAGGAAGCTGAGTTGGCCTGCTGCCACCGCTGAGCAATAACTAGCATAACCCCCTTGGGGCCTCTAAACGGGTCTTCGAGGGTTTTTG
                          ◀───────────
                          T7 TERMINATOR PRIMER #69337-3
                    T7 TERMINATOR
``` pET-27b(+) CLONING/EXPRESSION REGION

FIG. 4

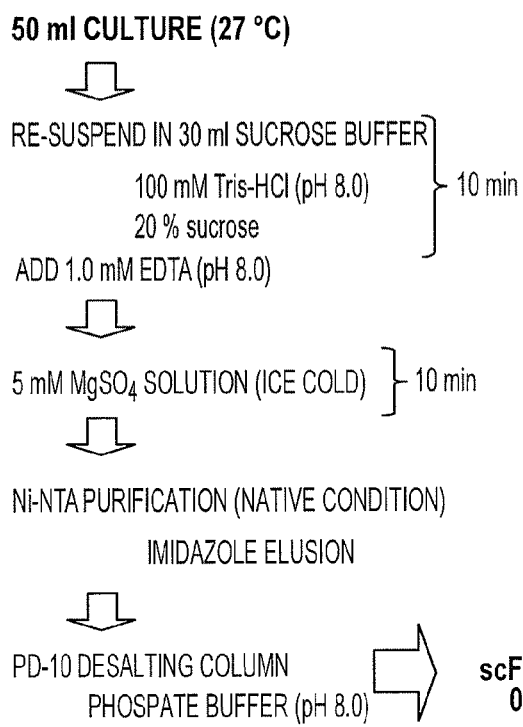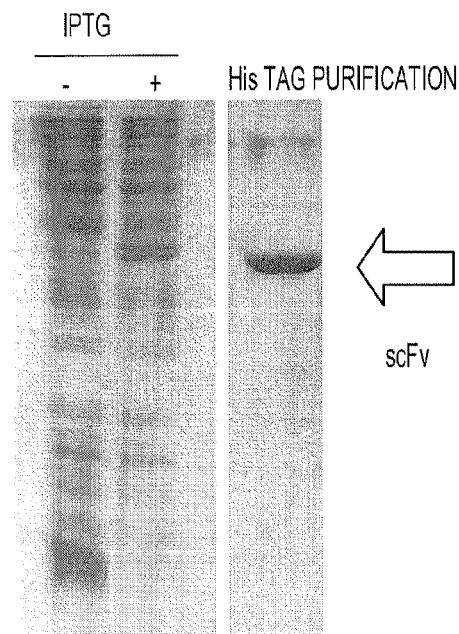
FIG. 6

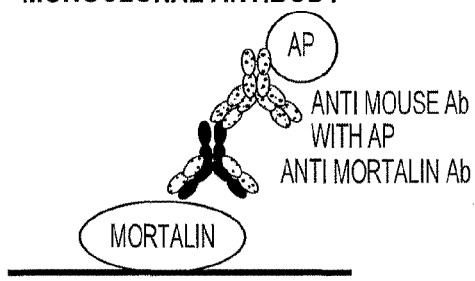
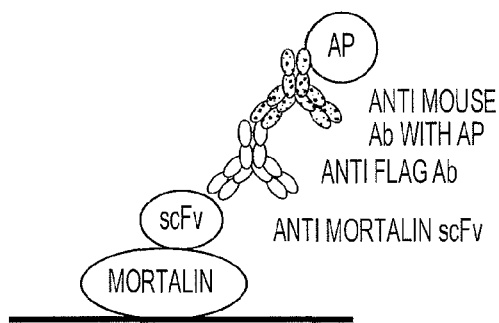
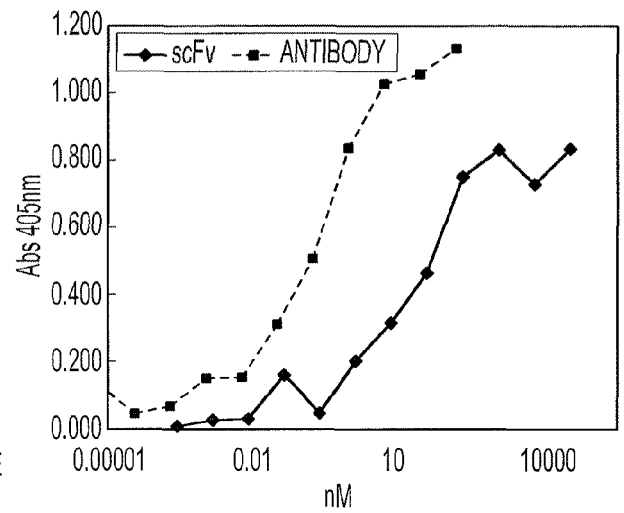
FIG. 7

FULL LENGTH  |His| 1 ─────────────────────── 679
Δmot #1(1-252) |His| 1 ──────── 252
Δmot #2(250-410)  |His| 205 ──────── 410
Δmot #3(310-435)  |His| 310 ──── 435
Δmot #4(403-679)  |His| 403 ─────────── 679
Δmot #5(1-435) |His| 1 ─────────── 435
Δmot #6(252-679)  |His| 252 ─────────── 679

| | Ab (38-4) | Ab (52-3) | Ab (96-5) |
|---|---|---|---|
| Mot-2 FULL LENGTH | + Kd(M) 3.35 x10$^{-9}$ | + Kd(M) 8.17 x10$^{-9}$ | + Kd(M) 6.10 x10$^{-9}$ |
| Δmot #1 1-252 | - | - | - |
| Δmot #2 250-410 | + | +/- | + |
| Δmot #3 310-435 | + | - | + |
| Δmot #4 403-679 | - | + Kd(M) 4.61 x10$^{-9}$ | - |
| Δmot #5 1-453 | + | + | + |
| Δmot #6 252 679 | - | + | - |

Ab 52-3 BINDS TO THE AMINO ACID RESIDUES 403-435

FIG. 8

ELISA OD$_{405}$ nm

| | 1-252 | 47-252 | 105-282 | 47-282 | 250-410 | 282-435 | 105-435 | 310-435 | 1-435 | 105-538 | mot-2 FULL LENGTH |
|---|---|---|---|---|---|---|---|---|---|---|---|
| Ab38-4 | 0.004 | 0.011 | 0.014 | 0.007 | 2.907 | 0.343 | 2.870 | 2.595 | 0.090 | 0.017 | 1.635 |
| Ab52-3 | 0.018 | 0.028 | 0.021 | 0.049 | 0.007 | 0.004 | 0.020 | 0.048 | 0.020 | 0.049 | 0.759 |
| Ab96-5 | 0.006 | 0.003 | 0.009 | 0.004 | 2.712 | 0.194 | 2.951 | 1.907 | 0.050 | 0.030 | 1.229 |

⇨

| | 1-252 | 47-252 | 105-282 | 47-282 | 250-410 | 282-435 | 105-435 | 310-435 | 1-435 | 105-538 | mot-2 FULL LENGTH |
|---|---|---|---|---|---|---|---|---|---|---|---|
| Ab38-4 | − | − | − | − | ++ | ++ | ++ | ++ | + | − | ++ |
| Ab52-3 | − | − | − | + | − | − | − | + | − | + | ++ |
| Ab96-5 | − | − | − | − | ++ | ++ | ++ | ++ | + | − | ++ |

ELISA ANALYSIS OF MORTALIN ANTIBODIES 38-4, 52-3, 96-5 AGAINST THE FULL-LENGTH MORTALIN AND DELETION MUTANTS AS INDICATED BY AMINO ACID RESIDUES.

Ab 38-4, 96-5 BINDS TO THE AMINO ACID RESIDUES 310-435.

FIG. 9

USE OF MOT scFv IN PLACE OF ANTIBODY FOR DETECTION OF MORTALIN PROTEIN FROM HUMAN CELL LYSATES. (NORMAL HUMAN SKIN FIBROBLASTS, TIG-1; LUNG FIBROBLASTS, MRC5; LUNG CARCINOMA, A549; BREAST CARCINOMA, MCF7 AND OSTEOCARCINOMA, U2OS).

USE OF MOT scFv IN PLACE OF ANTIBODY FOR IMMUNOPRECIPITATION OF MORTALIN PROTEIN FROM HUMAN CELL LYSATES. (NORMAL HUMAN SKIN FIBROBLASTS, TIG-1; LUNG FIBROBLASTS, MRC5; LUNG CARCINOMA, A549; BREAST CARCINOMA, MCF7 AND OSTEOCARCINOMA, U2OS).

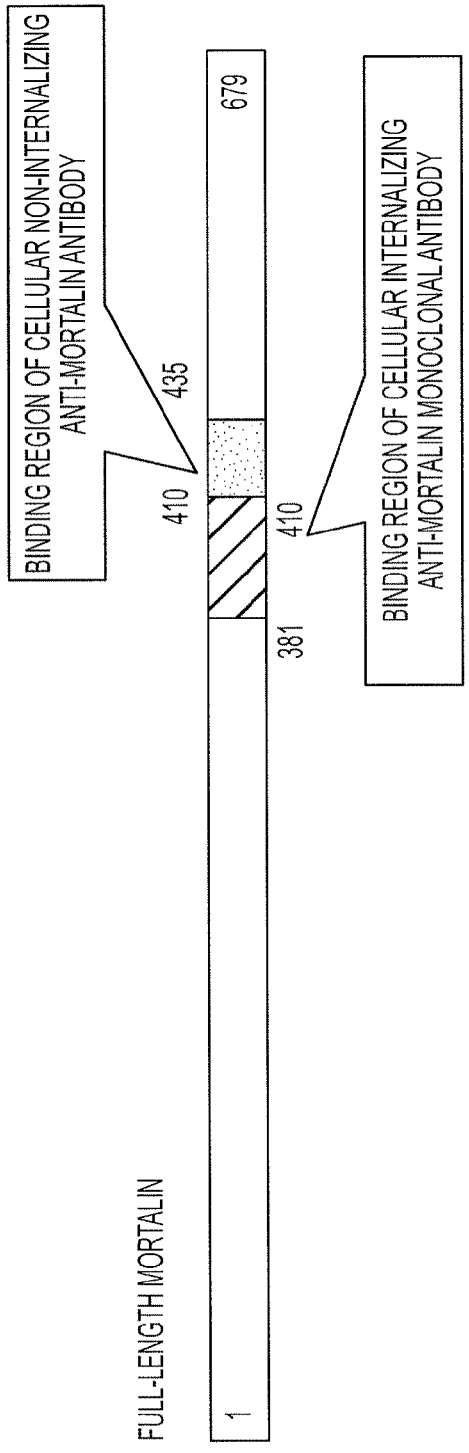

```
MOUSE    1' MISATRAAAARLVGTAASRSPAAARPQDGWNGLSHEAFRFVSRRDYASEAIKGAVVGIDL
            ****.********.****.*.***.**.**********.********************
HUMAN    1" MISASRAAAARLVGAAASRGPTAARHQDSWNGLSHEAFRLVSRRDYASEAIKGAVVGIDL

61' GTTNSCVAVMEGKQAKVLENAEGARTTPSVVAFTADGERLVGMPARRQAVTNPNNTFYAT
            *********************************************.**************
        61" GTTNSCVAVMEGKQAKVLENAEGARTTPSVVAFTADGERLVGMPAKRQAVTNPNNTFYAT

121' KRLIGRRYDDPEVQKDTKNVPFKIVRASNGDAWVEAHGKLYSPSQIGAFVLMKMKETAEN
            **************.*********************************************
       121" KRLIGRRYDDPEVQKDIKNVPFKIVRASNGDAWVEAHGKLYSPSQIGAFVLMKMKETAEN

181' YLGHTAKNAVITVPAYFNDSQRQATKDAGQISGLNVLRVINEPTAAALAYGLDKSEDKVI
            ************************************************************
       181" YLGHTAKNAVITVPAYFNDSQRQATKDAGQISGLNVLRVINEPTAAALAYGLDKSEDKVI

241' AVYDLGGGTFDISILEIQKGVFEVKSTNGDTFLGGEDFDQALLRHIVKEFKRETGVDLTK
            ************************************************************
       241" AVYDLGGGTFDISILEIQKGVFEVKSTNGDTFLGGEDFDQALLRHIVKEFKRETGVDLTK

301' DNMALQRVREAAEKAKCELSSSVQTDINLPYLTMDASGPKHLNMKLTRAQFEGIVTDLIK
            ***********************************.*********************.
       301" DNMALQRVREAAEKAKCELSSSVQTDINLPYLTMDSSGPKHLNMKLTRAQFEGIVTDLIR

361' RTIAPCQKAMQDAEVSKSDIGEVILVGGMTRMPKVQQTVQDLFGRAPSKAVNPDEAVAIG
            ************************************************************
       361" RTIAPCQKAMQDAEVSKSDIGEVILVGGMTRMPKVQQTVQDLFGRAPSKAVNPDEAVAIG

421' AAIQGGVLAGDVTDVLLLDVTPLSLGIETLGGVFTKLINRNTTIPTKKSQVFSTAADGQT
            ************************************************************
       421" AAIQGGVLAGDVTDVLLLDVTPLSLGIETLGGVFTKLINRNTTIPTKKSQVFSTAADGQT

481' QVEIKVCQGEREMAGDNKLLGQFTLIGIPPAPRGVPQIEVTSDIDANGIVHVSAKDKGTG
            *****************************************.****************
       481" QVEIKVCQGEREMAGDNKLLGQFTLIGIPPAPRGVPQIEVTFDIDANGIVHVSAKDKGTG

541' REQQIVIQSSGGLSKDDIENMVKNAEKYAEEDRRKKERVEAVNMAEGIIHDTETKMEEFK
            ************************************************************
       541" REQQIVIQSSGGLSKDDIENMVKNAEKYAEEDRRKKERVEAVNMAEGIIHDTETKMEEFK

601' DQLPADECNKLKEEISKMRALLAGKDSETGENIRQAASSLQQASLKLFEMAYKKMASERE
            ******************.***.********************************
       601" DQLPADECNKLKEEISKMRELLARKDSETGENIRQAASSLQQASLKLFEMAYKKMASERE

661' GSGSSGTGEQKEDQKEEKQ
            *******************
       661" GSGSSGTGEQKEDQKEEKQ
```

FIG. 13

PEPTIDE ARRAY SPANNING 103 AMINO ACIDS
aa348-RAQFEGIVTDLIRRTIAPCQKAMQDAEVSKSDIGEVILVGGMTRMPKVQQTVQDLFGRAPSKAVNPDEAVAIGAAIQG → TO FIG. 14B

| # | Sequence |
|---|---|
| 1 | RAQFEGIVTDLIRRT |
| 2 | AQFEGIVTDLIRRTI |
| 3 | QFEGIVTDLIRRTIA |
| 4 | FEGIVTDLIRRTIAP |
| 5 | EGIVTDLIRRTIAPC |
| 6 | GIVTDLIRRTIAPCQ |
| 7 | IVTDLIRRTIAPCQK |
| 8 | VTDLIRRTIAPCQKA |
| 9 | TDLIRRTIAPCQKAM |
| 10 | DLIRRTIAPCQKAMQ |
| 11 | LIRRTIAPCQKAMQD |
| 12 | IRRTIAPCQKAMQDA |
| 13 | RRTIAPCQKAMQDAE |
| 14 | RTIAPCQKAMQDAEV |
| 15 | TIAPCQKAMQDAEVS |
| 16 | IAPCQKAMQDAEVSK |
| 17 | APCQKAMQDAEVSKS |
| 18 | PCQKAMQDAEVSKSD |
| 19 | CQKAMQDAEVSKSDI |
| 20 | QKAMQDAEVSKSDIG |
| 21 | KAMQDAEVSKSDIGE ← |
| 22 | AMQDAEVSKSDIGEV |
| 23 | MQDAEVSKSDIGEVI |
| 24 | QDAEVSKSDIGEVIL | → TO FIG. 14B
| 25 | DAEVSKSDIGEVILV |
| 26 | AEVSKSDIGEVILVG |
| 27 | EVSKSDIGEVILVGG |
| 28 | VSKSDIGEVILVGGM |
| 29 | SKSDIGEVILVGGMT |
| 30 | KSDIGEVILVGGMTR |
| 31 | SDIGEVILVGGMTRM |
| 32 | DIGEVILVGGMTRMP |
| 33 | IGEVILVGGMTRMPK |
| 34 | GEVILVGGMTRMPKV ← |
| 35 | EVILVGGMTRMPKVQ ← |
| 36 | VILVGGMTRMPKVQQ |
| 37 | ILVGGMTRMPKVQQT |
| 38 | LVGGMTRMPKVQQTV |
| 39 | VGGMTRMPKVQQTVQ |
| 40 | GGMTRMPKVQQTVQD |
| 41 | GMTRMPKVQQTVQDL ← |
| 42 | MTRMPKVQQTVQDLF |
| 43 | TRMPKVQQTVQDLFG ← |
| 44 | RMPKVQQTVQDLFGR ← |
| 45 | MPKVQQTVQDLFGRA |
| 46 | PKVQQTVQDLFGRAP ← |

FIG. 14A

FROM FIG. 14A → GVLAGDVTDVLLLDVTPLSLGIETL –aa450

| | | |
|---|---|---|
| 46 | PKVQQTVQDLFGRAP | ← |
| 47 | KVQQTVQDLFGRAPS | ← |
| 48 | VQQTVQDLFGRAPSK | ← |
| 49 | QQTVQDLFGRAPSKA | ← |
| 50 | QTVQDLFGRAPSKAV | ← |
| 51 | TVQDLFGRAPSKAVN | ← |
| 52 | VQDLFGRAPSKAVNP | ← |
| 53 | QDLFGRAPSKAVNPD | ← |
| 54 | DLFGRAPSKAVNPDE | ← |
| 55 | LFGRAPSKAVNPDEA | ← |
| 56 | FGRAPSKAVNPDEAV | |
| 57 | GRAPSKAVNPDEAVA | |
| 58 | RAPSKAVNPDEAVAI | |
| 59 | APSKAVNPDEAVAIG | |
| 60 | PSKAVNPDEAVAIGA | |
| 61 | SKAVNPDEAVAIGAA | |
| 62 | KAVNPDEAVAIGAAI | |
| 63 | AVNPDEAVAIGAAIQ | |
| 64 | VNPDEAVAIGAAIQG | |
| 65 | NPDEAVAIGAAIQGG | |
| 66 | PDEAVAIGAAIQGGV | |
| 67 | DEAVAIGAAIQGGVL | |
| 68 | EAVAIGAAIQGGVLA | |
| 69 | AVAIGAAIQGGVLAG | |
| 70 | VAIGAAIQGGVLAGD | |
| 71 | AIGAAIQGGVLAGDV | |
| 72 | IGAAIQGGVLAGDVT | |
| 73 | GAAIQGGVLAGDVTD | |
| 74 | AAIQGGVLAGDVTDV | |
| 75 | AIQGGVLAGDVTDVL | |
| 76 | IQGGVLAGDVTDVLL | |
| 77 | QGGVLAGDVTDVLLL | |
| 78 | GGVLAGDVTDVLLLD | |
| 79 | GVLAGDVTDVLLLDV | |
| 80 | VLAGDVTDVLLLDVT | |
| 81 | LAGDVTDVLLLDVTP | |
| 82 | AGDVTDVLLLDVTPL | |
| 83 | GDVTDVLLLDVTPLS | |
| 84 | DVTDVLLLDVTPLSL | |
| 85 | VTDVLLLDVTPLSLG | |
| 86 | TDVLLLDVTPLSLGI | |
| 87 | DVLLLDVTPLSLGIE | |
| 88 | VLLLDVTPLSLGIET | |
| 89 | LLLDVTPLSLGIETL | |

FROM FIG. 14A →

FIG. 14B

PEPTIDE NUMBER

18. PCQKAMQDAEVSKSD
19. CQKAMQDAEVSKSDI
20. QKAMQDAEVSKSDIG
21. KAMQDAEVSKSDIGE ←
22. AMQDAEVSKSDIGEV
23. MQDAEVSKSDIGEVI
24. QDAEVSKSDIGEVIL
25. DAEVSKSDIGEVILV
26. AEVSKSDIGEVILVG
27. EVSKSDIGEVILVGG
28. VSKSDIGEVILVGGM
29. SKSDIGEVILVGGMT
30. KSDIGEVILVGGMTR
31. SDIGEVILVGGMTRM
32. DIGEVILVGGMTRMP
33. IGEVILVGGMTRMPK
34. GEVILVGGMTRMPKV ←
35. EVILVGGMTRMPKVQ ←
36. VILVGGMTRMPKVQQ
37. ILVGGMTRMPKVQQT
38. LVGGMTRMPKVQQTV
39. VGGMTRMPKVQQTVQ
40. GGMTRMPKVQQTVQD
41. GMTRMPKVQQTVQDL ←
42. MTRMPKVQQTVQDLF
43. TRMPKVQQTVQDLFG ←
44. RMPKVQQTVQDLFGR
45. MPKVQQTVQDLFGRA
46. PKVQQTVQDLFGRAP ←
47. KVQQTVQDLFGRAPS ←
48. VQQTVQDLFGRAPSK ←
49. QQTVQDLFGRAPSKA ←  [LFGRAP]
50. QTVQDLFGRAPSKAV ←
51. TVQDLFGRAPSKAVN ←
52. VQDLFGRAPSKAVNP ←
53. QDLFGRAPSKAVNPD ←
54. DLFGRAPSKAVNPDE ←
55. LFGRAPSKAVNPDEA ←
56. FGRAPSKAVNPDEAV
57. GRAPSKAVNPDEAVA
58. RAPSKAVNPDEAVAI aa 381- G E V I L V G G M T R M P K V Q Q T V Q D L F G R A P S K A -aa 410 SEQ ID NO: 56
aa 402- L F G R A P -aa 407 SEQ ID NO: 66

FIG. 18

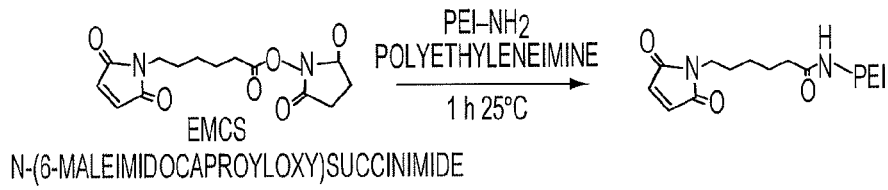
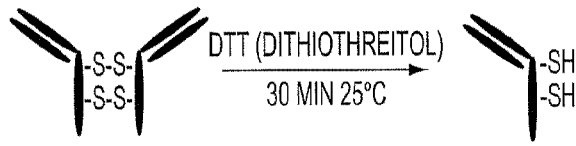
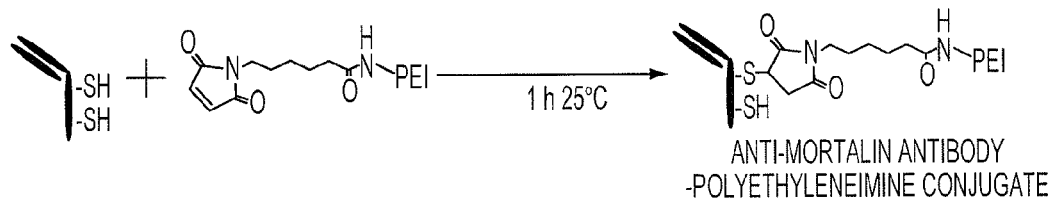
FIG. 19
FIG. 20

SEQUENCE LISTING

<160> NUMBER OF SEQ ID NOS: 176

<210> SEQ ID NO 1
<211> LENGTH: 16

```
<212> TYPE: PRT
<213> ORGANISM: Artificial Sequence
<220> FEATURE:
<223> OTHER INFORMATION: Synthetic polypeptide

<400> SEQUENCE: 1

Lys Ser Ser Gln Ser Leu Leu Asp Ser Asp Gly Lys Thr Tyr Leu Asn
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 2

Leu Val Ser Lys Leu Asp Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 3

Trp Gln Gly Thr His Phe Pro Arg Thr
1               5

<210> SEQ ID NO 4
<211> LENGTH: 132
<212> TYPE: PRT
<213> ORGANISM: Artificial Sequence
<220> FEATURE:
<223> OTHER INFORMATION: Synthetic polypeptide

<400> SEQUENCE: 4

Met Met Ser Pro Ala Gln Phe Leu Phe Leu Leu Val Leu Trp Ile Arg
1               5                   10                  15

Glu Thr Asn Gly Asp Val Val Met Thr Gln Thr Pro Leu Thr Leu Ser
            20                  25                  30

Val Thr Ile Gly Gln Pro Ala Ser Ile Ser Cys Lys Ser Ser Gln Ser
        35                  40                  45

Leu Leu Asp Ser Asp Gly Lys Thr Tyr Leu Asn Trp Leu Leu Gln Arg
    50                  55                  60

Pro Gly Gln Ser Pro Lys Arg Leu Ile Tyr Leu Val Ser Lys Leu Asp
65                  70                  75                  80

Ser Gly Val Pro Asp Arg Phe Thr Gly Ser Gly Ser Gly Thr Asp Phe
                85                  90                  95

Thr Leu Lys Ile Ser Arg Val Glu Ala Glu Asp Leu Gly Val Tyr Tyr
            100                 105                 110

Cys Trp Gln Gly Thr His Phe Pro Arg Thr Phe Gly Gly Gly Thr Lys
        115                 120                 125

Leu Glu Ile Lys
        130

<210> SEQ ID NO 5
<211> LENGTH: 132
<212> TYPE: PRT
<213> ORGANISM: Artificial Sequence
<220> FEATURE:
<223> OTHER INFORMATION: Synthetic polypeptide
```

```
<400> SEQUENCE: 5

Met Met Ser Pro Ala Gln Phe Leu Phe Leu Val Leu Trp Ile Arg
1               5                   10                  15

Glu Thr Thr Gly Asp Val Val Met Thr Gln Thr Pro Leu Thr Leu Ser
            20                  25                  30

Val Thr Ile Gly Gln Pro Ala Ser Ile Ser Cys Lys Ser Gln Ser
        35                  40                  45

Leu Leu Asp Ser Asp Gly Lys Thr Tyr Leu Asn Trp Leu Leu Gln Arg
    50                  55                  60

Pro Gly Gln Ser Pro Lys Arg Leu Ile Tyr Leu Val Ser Lys Leu Asp
65                  70                  75                  80

Ser Gly Val Pro Asp Arg Phe Thr Gly Ser Gly Ser Gly Thr Asp Phe
                85                  90                  95

Thr Leu Lys Ile Ser Arg Val Glu Ser Glu Asp Leu Gly Val Tyr Tyr
            100                 105                 110

Cys Trp Gln Gly Thr His Phe Pro Arg Thr Phe Gly Gly Gly Thr Lys
        115                 120                 125

Leu Glu Ile Lys
    130

<210> SEQ ID NO 6
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 6

Arg Ala Ser Gln Glu Ile Ser Gly Tyr Leu Ser
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 7

Ala Ala Ser Thr Leu Asp Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 8

Leu Gln Tyr Ala Ser Tyr Pro Pro Thr
1               5

<210> SEQ ID NO 9
<211> LENGTH: 129
<212> TYPE: PRT
<213> ORGANISM: Artificial Sequence
<220> FEATURE:
<223> OTHER INFORMATION: Synthetic polypeptide

<400> SEQUENCE: 9

Met Asp Met Arg Val Pro Ala His Val Phe Gly Phe Leu Leu Leu Trp
```

-continued

```
                 1               5                  10                  15
Phe Pro Gly Thr Arg Cys Asp Ile Gln Met Thr Gln Ser Pro Ser Ser
                    20                  25                  30

Leu Ser Ala Ser Leu Gly Glu Arg Val Ser Leu Thr Cys Arg Ala Ser
                    35                  40                  45

Gln Glu Ile Ser Gly Tyr Leu Ser Trp Leu Gln Gln Lys Pro Asp Gly
                    50                  55                  60

Thr Ile Lys Arg Leu Ile Tyr Ala Ala Ser Thr Leu Asp Ser Gly Val
 65                     70                  75                  80

Pro Lys Arg Phe Ser Gly Ser Arg Ser Gly Ser Asp Tyr Ser Leu Thr
                    85                  90                  95

Ile Ser Ser Leu Glu Ser Glu Asp Phe Ala Asp Tyr Tyr Cys Leu Gln
                    100                 105                 110

Tyr Ala Ser Tyr Pro Pro Thr Phe Gly Gly Gly Thr Lys Leu Glu Ile
                    115                 120                 125

Lys

<210> SEQ ID NO 10
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 10

Arg Ser Ser Lys Ser Leu Leu Tyr Ser Asn Gly Ile Thr Tyr Leu Tyr
 1               5                  10                  15

<210> SEQ ID NO 11
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 11

Gln Met Ser Asn Leu Ala Ser
 1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 12

Ala Gln Asn Leu Glu Leu Pro Trp Thr
 1               5

<210> SEQ ID NO 13
<211> LENGTH: 133
<212> TYPE: PRT
<213> ORGANISM: Artificial Sequence
<220> FEATURE:
<223> OTHER INFORMATION: Synthetic polypeptide

<400> SEQUENCE: 13

Met Arg Phe Ser Ala Gln Leu Leu Gly Leu Leu Val Leu Trp Ile Pro
 1               5                  10                  15

Gly Ser Thr Ala Glu Lys Ile Val Met Thr Gln Ala Ala Phe Ser Asn
                    20                  25                  30
```

```
Pro Val Thr Leu Gly Thr Ser Ala Ser Ile Ser Cys Arg Ser Ser Lys
        35                  40                  45

Ser Leu Leu Tyr Ser Asn Gly Ile Thr Tyr Leu Tyr Trp Tyr Leu Gln
    50                  55                  60

Lys Pro Gly Gln Ser Pro Gln Leu Leu Ile Tyr Gln Met Ser Asn Leu
65                  70                  75                  80

Ala Ser Gly Val Pro Asp Arg Phe Ser Ser Gly Ser Gly Thr Asp
                85                  90                  95

Phe Thr Leu Arg Ile Ser Arg Val Glu Ala Glu Asp Val Gly Val Tyr
                100                 105                 110

Tyr Cys Ala Gln Asn Leu Glu Leu Pro Trp Thr Phe Gly Gly Gly Thr
                115                 120                 125

Lys Leu Glu Ile Lys
        130

<210> SEQ ID NO 14
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 14

Ser Tyr Trp Met His
1               5

<210> SEQ ID NO 15
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 15

Glu Ile Asp Pro Ser Asp Ser Tyr Thr Lys Tyr Asn Gln Lys Phe Lys
1               5                   10                  15

Gly

<210> SEQ ID NO 16
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 16

Gly Asp Tyr
1

<210> SEQ ID NO 17
<211> LENGTH: 131
<212> TYPE: PRT
<213> ORGANISM: Artificial Sequence
<220> FEATURE:
<223> OTHER INFORMATION: Synthetic polypeptide

<400> SEQUENCE: 17

Met Gly Trp Ser Cys Ile Ile Leu Phe Leu Val Ser Thr Ala Thr Gly
1               5                   10                  15

Val His Ser Gln Val Gln Leu Gln Gln Pro Gly Ala Glu Leu Val Lys
                20                  25                  30

Pro Gly Ala Ser Val Lys Leu Ser Cys Lys Ala Ser Gly Tyr Thr Phe
            35                  40                  45
```

```
Thr Ser Tyr Trp Met His Trp Val Lys Gln Arg Pro Gly Gln Gly Leu
    50                  55                  60

Glu Trp Ile Gly Glu Ile Asp Pro Ser Asp Ser Tyr Thr Lys Tyr Asn
 65                  70                  75                  80

Gln Lys Phe Lys Gly Lys Ala Thr Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Gly Asp Tyr Trp Gly Gln Gly Thr Thr Leu Thr
            115                 120                 125

Val Ser Ser
    130
```

<210> SEQ ID NO 18
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 18

```
Glu Ile Asp Pro Ser Asp Ser Tyr Thr Asp Tyr Asn Gln Asn Phe Lys
 1                5                  10                  15

Gly
```

<210> SEQ ID NO 19
<211> LENGTH: 131
<212> TYPE: PRT
<213> ORGANISM: Artificial Sequence
<220> FEATURE:
<223> OTHER INFORMATION: Synthetic polypeptide

<400> SEQUENCE: 19

```
Met Gly Trp Ser Cys Ile Ile Leu Phe Leu Val Ser Thr Ala Thr Gly
 1                5                  10                  15

Val His Ser Gln Val Gln Leu Gln Pro Gly Ala Glu Leu Val Lys
                 20                  25                  30

Pro Gly Ala Ser Val Lys Leu Ser Cys Lys Ala Ser Gly Tyr Thr Phe
            35                  40                  45

Thr Ser Tyr Trp Met His Trp Val Lys Gln Arg Pro Gly Gln Gly Leu
    50                  55                  60

Glu Trp Ile Gly Glu Ile Asp Pro Ser Asp Ser Tyr Thr Asp Tyr Asn
 65                  70                  75                  80

Gln Asn Phe Lys Gly Lys Ala Thr Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Gly Asp Tyr Trp Gly Gln Gly Thr Thr Leu Thr
            115                 120                 125

Val Ser Ser
    130
```

<210> SEQ ID NO 20
<211> LENGTH: 131
<212> TYPE: PRT
<213> ORGANISM: Artificial Sequence
<220> FEATURE:
<223> OTHER INFORMATION: Synthetic polypeptide

<400> SEQUENCE: 20

```
Met Gly Trp Ser Cys Ile Ile Leu Phe Leu Val Ser Thr Ala Thr Gly
1               5                   10                  15

Val His Ser Gln Val Gln Leu Gln Gln Pro Gly Ala Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Trp Met His Trp Val Lys Gln Arg Pro Gly Gln Gly Leu
    50                  55                  60

Glu Trp Ile Gly Glu Ile Asp Pro Ser Asp Ser Tyr Thr Lys Tyr Asn
65                  70                  75                  80

Gln Lys Phe Lys Gly Lys Ala Thr Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Gly Asp Tyr Trp Gly Gln Gly Thr Ile Leu Arg
        115                 120                 125

Val Ser Ser
    130
```

<210> SEQ ID NO 21
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 21

```
Thr Asn Ala Met Asn
1               5
```

<210> SEQ ID NO 22
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 22

```
Arg Ile Arg Ser Lys Ser Asn Asn Tyr Ala Thr Tyr Tyr Ala Asp Ser
1               5                   10                  15

Val Lys Asp
```

<210> SEQ ID NO 23
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 23

```
Asp Gly Tyr Tyr Ser Tyr
1               5
```

<210> SEQ ID NO 24
<211> LENGTH: 136
<212> TYPE: PRT
<213> ORGANISM: Artificial Sequence
<220> FEATURE:
<223> OTHER INFORMATION: Synthetic polypeptide

<400> SEQUENCE: 24

```
Met Leu Leu Gly Leu Lys Trp Val Phe Phe Val Val Phe Tyr Gln Gly
```

```
                1               5                  10                  15
        Val His Cys Glu Val Gln Leu Val Glu Thr Gly Gly Gly Leu Val Gln
                        20                  25                  30

Pro Lys Gly Ser Leu Lys Leu Ser Cys Ala Ala Ser Gly Phe Thr Phe
                        35                  40                  45

Asn Thr Asn Ala Met Asn Trp Val Arg Gln Ala Pro Gly Lys Gly Leu
                        50                  55                  60

Glu Trp Val Ala Arg Ile Arg Ser Lys Ser Asn Asn Tyr Ala Thr Tyr
         65                  70                  75                  80

Tyr Ala Asp Ser Val Lys Asp Arg Phe Thr Ile Ser Arg Asp Asp Ser
                        85                  90                  95

Gln Ser Met Leu Tyr Leu Gln Met Asn Asn Leu Lys Thr Glu Asp Thr
                       100                 105                 110

Ala Met Tyr Tyr Cys Val Arg Asp Gly Tyr Tyr Ser Tyr Trp Gly Gln
                       115                 120                 125

Gly Thr Leu Val Thr Val Ser Ala
                       130                 135

<210> SEQ ID NO 25
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 25

Ser Tyr Trp Met His
1               5

<210> SEQ ID NO 26
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 26

Glu Ile Asn Pro Ser Asn Gly Arg Thr Asn Tyr Asn Glu Lys Phe Lys
1               5                   10                  15

Ser

<210> SEQ ID NO 27
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 27

Ser Arg Tyr Tyr Gly Ser Cys Tyr Phe Asp Tyr
1               5                   10

<210> SEQ ID NO 28
<211> LENGTH: 139
<212> TYPE: PRT
<213> ORGANISM: Artificial Sequence
<220> FEATURE:
<223> OTHER INFORMATION: Synthetic polypeptide

<400> SEQUENCE: 28

Met Gly Trp Ser Tyr Ile Ile Leu Phe Leu Val Ala Thr Ala Thr Asp
1               5                   10                  15
```

-continued

```
Val His Ser Gln Val Gln Leu Gln Gln Pro Gly Ala Glu Leu Val Lys
         20                  25                  30

Pro Gly Ala Ser Val Lys Leu Ser Cys Lys Ala Ser Gly Tyr Thr Phe
             35                  40                  45

Thr Ser Tyr Trp Met His Trp Val Lys Gln Arg Pro Gly Gln Gly Leu
 50                  55                  60

Glu Trp Ile Gly Glu Ile Asn Pro Ser Asn Gly Arg Thr Asn Tyr Asn
 65                  70                  75                  80

Glu Lys Phe Lys Ser Lys Ala Thr Leu Thr Val Asp Lys Ser Ser Ser
                 85                  90                  95

Thr Ala Tyr Met Gln Leu Ser Ser Leu Thr Ser Glu Asp Ser Ala Val
             100                 105                 110

Tyr Tyr Cys Ala Arg Ser Arg Tyr Tyr Gly Ser Cys Tyr Phe Asp Tyr
         115                 120                 125

Trp Gly Gln Gly Thr Thr Leu Thr Val Ser Ser
     130                 135
```

<210> SEQ ID NO 29
<211> LENGTH: 101
<212> TYPE: PRT
<213> ORGANISM: Artificial Sequence
<220> FEATURE:
<223> OTHER INFORMATION: Synthetic polypeptide

<400> SEQUENCE: 29

```
Glu Ala Ala Glu Lys Ala Lys Cys Glu Leu Ser Ser Ser Val Gln Thr
1               5                  10                  15

Asp Ile Asn Leu Pro Tyr Leu Thr Met Asp Ala Ser Gly Pro Lys His
             20                  25                  30

Leu Asn Met Lys Leu Thr Arg Ala Gln Phe Glu Gly Ile Val Thr Asp
         35                  40                  45

Leu Ile Lys Arg Thr Ile Ala Pro Cys Gln Lys Ala Met Gln Asp Ala
     50                  55                  60

Glu Val Ser Lys Ser Asp Ile Gly Glu Val Ile Leu Val Gly Gly Met
65                  70                  75                  80

Thr Arg Met Pro Lys Val Gln Gln Thr Val Gln Asp Leu Phe Gly Arg
                 85                  90                  95

Ala Pro Ser Lys Ala
             100
```

<210> SEQ ID NO 30
<211> LENGTH: 33
<212> TYPE: PRT
<213> ORGANISM: Artificial Sequence
<220> FEATURE:
<223> OTHER INFORMATION: Synthetic polypeptide

<400> SEQUENCE: 30

```
Phe Gly Arg Ala Pro Ser Lys Ala Val Asn Pro Asp Glu Ala Val Ala
1               5                  10                  15

Ile Gly Ala Ala Ile Gln Gly Gly Val Leu Ala Gly Asp Val Thr Asp
             20                  25                  30

Val
```

<210> SEQ ID NO 31
<211> LENGTH: 278
<212> TYPE: PRT
<213> ORGANISM: Artificial Sequence
<220> FEATURE:
<223> OTHER INFORMATION: Synthetic polypeptide

<400> SEQUENCE: 31

```
Met Asp Tyr Lys Asp Val Val Met Thr Gln Thr Pro Leu Thr Leu Ser
1               5                   10                  15
Val Thr Ile Gly Gln Pro Ala Ser Ile Ser Cys Lys Ser Ser Gln Ser
            20                  25                  30
Leu Leu Asp Ser Asp Gly Lys Thr Tyr Leu Asn Trp Leu Leu Gln Arg
        35                  40                  45
Pro Gly Gln Ser Pro Lys Arg Leu Ile Tyr Leu Val Ser Lys Leu Asp
    50                  55                  60
Ser Gly Val Pro Asp Arg Phe Thr Gly Ser Gly Ser Gly Thr Asp Phe
65                  70                  75                  80
Thr Leu Lys Ile Ser Arg Val Glu Ala Glu Asp Leu Gly Val Tyr Tyr
                85                  90                  95
Cys Trp Gln Gly Thr His Phe Pro Arg Thr Phe Gly Gly Gly Thr Lys
            100                 105                 110
Leu Glu Ile Lys Arg Pro Asn Gly Ala Ser Asn Ser Ser Ala Pro
        115                 120                 125
Glu Thr Ser Ser Ala Ser Gly Ser Gln Val Gln Leu Gln Gln Pro Gly
130                 135                 140
Ala Glu Leu Val Lys Pro Gly Ala Ser Val Lys Leu Ser Cys Lys Ala
145                 150                 155                 160
Ser Gly Tyr Thr Phe Thr Ser Tyr Trp Met His Trp Val Lys Gln Arg
                165                 170                 175
Pro Gly Gln Gly Leu Glu Trp Ile Gly Glu Ile Asp Pro Ser Asp Ser
            180                 185                 190
Tyr Thr Lys Tyr Asn Gln Lys Phe Lys Gly Lys Ala Thr Leu Thr Val
        195                 200                 205
Asp Lys Ser Ser Ser Thr Ala Tyr Met Gln Leu Ser Ser Leu Thr Ser
    210                 215                 220
Glu Asp Ser Ala Val Tyr Tyr Cys Ala Arg Gly Asp Tyr Trp Gly Gln
225                 230                 235                 240
Gly Thr Thr Leu Thr Val Leu Ser Ser Asp Tyr Lys Asp Asp Asp Asp
                245                 250                 255
Lys Ala Ser Gln Pro Glu Leu Ala Pro Glu Asp Pro Glu Asp Val Glu
            260                 265                 270
His His His His His His
        275
```

<210> SEQ ID NO 32
<211> LENGTH: 36
<212> TYPE: DNA
<213> ORGANISM: Artificial Sequence
<220> FEATURE:
<223> OTHER INFORMATION: Synthetic polynucleotide primer

<400> SEQUENCE: 32
ccatggacta caaagatgtt gtgatgaccc agactc        36

<210> SEQ ID NO 33
<211> LENGTH: 80
<212> TYPE: DNA
<213> ORGANISM: Artificial Sequence
<220> FEATURE:
<223> OTHER INFORMATION: Synthetic polynucleotide primer

<400> SEQUENCE: 33
ggatcccgaa gcagaactag tttccggagc agaactactg ttgctcgcgc cgttaggccg        60

```
tttgatttcc agcttggtgc                                                    80

<210> SEQ ID NO 34
<211> LENGTH: 34
<212> TYPE: DNA
<213> ORGANISM: Artificial Sequence
<220> FEATURE:
<223> OTHER INFORMATION: Synthetic polynucleotide primer

<400> SEQUENCE: 34
agttctgctt cgggatccca ggtccaactg cagc                                    34

<210> SEQ ID NO 35
<211> LENGTH: 31
<212> TYPE: DNA
<213> ORGANISM: Artificial Sequence
<220> FEATURE:
<223> OTHER INFORMATION: Synthetic polynucleotide primer

<400> SEQUENCE: 35
ttgctagcag atgagaggac tgtgagagtg g                                       31

<210> SEQ ID NO 36
<211> LENGTH: 21
<212> TYPE: DNA
<213> ORGANISM: Artificial Sequence
<220> FEATURE:
<223> OTHER INFORMATION: Synthetic polynucleotide primer

<400> SEQUENCE: 36
gggccagtgg atagacagat g                                                  21

<210> SEQ ID NO 37
<211> LENGTH: 21
<212> TYPE: DNA
<213> ORGANISM: Artificial Sequence
<220> FEATURE:
<223> OTHER INFORMATION: Synthetic polynucleotide primer

<400> SEQUENCE: 37
gggccagtgg atagacagat g                                                  21

<210> SEQ ID NO 38
<211> LENGTH: 21
<212> TYPE: DNA
<213> ORGANISM: Artificial Sequence
<220> FEATURE:
<223> OTHER INFORMATION: Synthetic polynucleotide primer

<400> SEQUENCE: 38
gggccagtgg atagacagat g                                                  21

<210> SEQ ID NO 39
<211> LENGTH: 21
<212> TYPE: DNA
<213> ORGANISM: Artificial Sequence
<220> FEATURE:
<223> OTHER INFORMATION: Synthetic polynucleotide primer

<400> SEQUENCE: 39
cagggaccaa gggatagaca g                                                  21

<210> SEQ ID NO 40
<211> LENGTH: 24
<212> TYPE: DNA
<213> ORGANISM: Artificial Sequence
```

-continued

```
<220> FEATURE:
<223> OTHER INFORMATION: Synthetic polynucleotide primer

<400> SEQUENCE: 40
caggggccag tggatagact gatg                                              24

<210> SEQ ID NO 41
<211> LENGTH: 24
<212> TYPE: DNA
<213> ORGANISM: Artificial Sequence
<220> FEATURE:
<223> OTHER INFORMATION: Synthetic polynucleotide primer

<400> SEQUENCE: 41
caggggccag tggatagact gatg                                              24

<210> SEQ ID NO 42
<211> LENGTH: 450
<212> TYPE: DNA
<213> ORGANISM: Artificial Sequence
<220> FEATURE:
<223> OTHER INFORMATION: Synthetic polynucleotide

<400> SEQUENCE: 42
atgatgagtc ctgcccagtt cctgtttctg ttagtgctct ggattcggga aaccaacggt       60
gatgttgtga tgacccagac tccactcact tgtcggtta ccattggaca accagcctcc      120
atctcttgca agtcaagtca gagcctccta gatagtgatg aaagacata tttgaattgg      180 ttgttacaga ggccaggcca gtctccaaag cgcctaatct atctggtgtc taaactggac      240
tctggagtcc ctgacaggtt cactggcagt ggatcaggga cagatttcac actgaaaatc      300
agcagagtgg aggctgagga tttgggagtt tattattgct ggcaaggtac acattttcct      360
cggacgttcg gtggaggcac caagctggaa atcaaacggg ctgatgctgc accaactgaa      420
tccatctttc ccaccatcca gggagcaaca                                        450

<210> SEQ ID NO 43
<211> LENGTH: 450
<212> TYPE: DNA
<213> ORGANISM: Artificial Sequence
<220> FEATURE:
<223> OTHER INFORMATION: Synthetic polynucleotide

<400> SEQUENCE: 43
atgatgagtc ctgcccagtt cctgtttctg ttagtgctct ggattcggga aaccaacggt       60
gatgttgtga tgacccagac tccactcact tgtcggtta ccattggaca accagcctcc      120
atctcttgca agtcaagtca gagcctccta gatagtgatg aaagacata tttgaattgg      180 ttgttacaga ggccaggcca gtctccaaag cgcctaatct atctggtgtc taaactggac      240
tctggagtcc ctgacaggtt cactggcagt ggatcaggga cagatttcac actgaaaatc      300
agcagagtgg aggctgagga tttgggagtt tattattgct ggcaaggtac acattttcct      360
cggacgttcg gtggaggcac caagctggaa atcaaacggg ctgatgctgc accaactgaa      420
tccatcttcc cgccatccag tgagccacga                                        450

<210> SEQ ID NO 44
<211> LENGTH: 450
<212> TYPE: DNA
<213> ORGANISM: Artificial Sequence
<220> FEATURE:
<223> OTHER INFORMATION: Synthetic polynucleotide

<400> SEQUENCE: 44
```

```
atgatgagtc ctgcccagtt cctgtttctg ttagtgctct ggattcggga aaccaccggt    60
gatgttgtga tgacccagac tccactcact ttgtcggtta ccattggaca accagcctcc   120
atctcttgca agtcaagtca gagcctctta gatagtgatg aaagacata tttgaattgg    180 ttgttacaga ggccaggcca gtctccaaag cgcctaatct atctggtgtc taaactggac   240
tctggagtcc ctgacaggtt cactggcagt ggatcaggga cagatttcac actgaaaatc   300
agcagagtgg agtctgagga tttgggagtt tattattgct ggcaaggtac acatttttcct  360 cggacgttcg gtggaggcac caagctggaa atcaaacggg ctgatgctgc ccccctgta   420 tccatcttcc cgccatccag tgagcaaagg                                    450
```

<210> SEQ ID NO 45
<211> LENGTH: 449
<212> TYPE: DNA
<213> ORGANISM: Artificial Sequence
<220> FEATURE:
<223> OTHER INFORMATION: Synthetic polynucleotide

<400> SEQUENCE: 45

```
atgatgagtc ctgcccagtt cctgtttctg ttagtgctct ggattcggga aaccaacggt    60
gatgttgtga tgacccagac tccactcact ttgtcggtta ccattggaca accagcctcc   120
atctcttgca agtcaagtca gagcctctta gatagtgatg aaagacata tttgaattgg    180 ttgttacaga ggccaggcca gtctccaaag cgcctaatct atctggtgtc taaactggac   240
tctggagtcc ctgacaggtt cactggcagt ggatcaggga cagatttcac actgaaaatc   300
agcagagtgg aggctgagga tttgggagtt tattattgct ggcaaggtac acattttcct   360
cggacgttcg gtggaggcac caagctggaa atcaaacggg ctgatgctgc accaactgta  420
tccatcttcc caccatccag tgagcaatc                                     449
```

<210> SEQ ID NO 46
<211> LENGTH: 433
<212> TYPE: DNA
<213> ORGANISM: Artificial Sequence
<220> FEATURE:
<223> OTHER INFORMATION: Synthetic polynucleotide

<400> SEQUENCE: 46

```
atggacatga gggttcctgc tcacgttttt ggcttcttgt tgctctggtt tccaggtacc    60
agatgtgaca tccagatgac ccagtctcca tcctccttat ctgcctctct gggagaaaga   120
gtcagtctca cttgtcgggc aagtcaggaa attagtggtt acttaagctg gcttcagcag   180
aaaccagatg gaactattaa acgcctgatc tacgccgcat ccactttaga ttctggtgtc   240
ccaaaaaggt tcagtggcag taggtctggg tcagattatt ctctcaccat cagcagcctt   300
gagtctgaag attttgcaga ctattactgt ctacaatatg ctagtcatcc tccgacgttc   360
ggtggaggca ccaagctgga aatcaaacgg gctgatgctg caccaactgt atccatcttc  420
ccaccatcca gtg                                                     433
```

<210> SEQ ID NO 47
<211> LENGTH: 450
<212> TYPE: DNA
<213> ORGANISM: Artificial Sequence
<220> FEATURE:
<223> OTHER INFORMATION: Synthetic polynucleotide

<400> SEQUENCE: 47

```
atgaggttct ctgctcagct tctggggctg cttgtgctct ggatccctgg atccactgca    60
```

```
gaaaaaattg tgatgacgca ggctgcattc tccaatccag tcactcttgg aacatcagct      120
tccatctcct gcaggtctag taagagtctc ctatatagta atggcatcac ttatttgtat      180
tggtatctgc agaagccagg ccagtctcct cagctcctga tttatcgat gtccaacctt       240 gcctcaggag tcccagacag gttcagtagc agtgggtcag gaactgattt cacactgaga      300
atcagcagag tggaggctga ggatgtgggt gtttattact gtgctcaaaa tctagaactt      360
ccgtggacgt tcggtggagg caccaagctg gaaatcaaac gggctgatgc tgcaccaact      420
gtatccatct tcccaccatc cagtgagcaa                                       450

<210> SEQ ID NO 48
<211> LENGTH: 410
<212> TYPE: DNA
<213> ORGANISM: Artificial Sequence
<220> FEATURE:
<223> OTHER INFORMATION: Synthetic polynucleotide

<400> SEQUENCE: 48
atgggatgga gctgtatcat cctcttcttg gtatcaacag ctacaggtgt ccactcccag      60
gtccaactgc agcagcctgg ggctgagctt gtgaagcctg ggcttcagt gaagctgtcc       120 tgcaaggctt ctggctacac cttcaccagc tactggatgc actgggtgaa gcagaggcct      180
ggacaaggcc ttgagtggat cggagagatt gatccttctg atagttatac taagtacaat     240
caaaagttca gggcaaggc cacattgact gtagacaaat cctccagcac agcctacatg       300
cagctcagca gcctgacatc tgaggactct gcggtctatt actgtgcaag gggggactac     360
tggggccaag gcaccactct cacagtctcc tcagccaaaa cgacaccccc                 410

<210> SEQ ID NO 49
<211> LENGTH: 430
<212> TYPE: DNA
<213> ORGANISM: Artificial Sequence
<220> FEATURE:
<223> OTHER INFORMATION: Synthetic polynucleotide

<400> SEQUENCE: 49
atgggatgga gctgtatcat cctcttcttg gtatcaacag ctacaggtgt ccactcccag      60
gtccaactgc agcagcctgg ggctgagctt gtgaagcctg ggcttcagt gaagctgtcc       120 tgcaaggctt ctggctacac cttcaccagc tactggatgc actgggtgaa gcagaggcct      180
ggacaaggcc ttgagtggat cggagagatt gatccttctg atagttatac taagtacaat     240
caaaagttca gggcaaggc cacattgact gtagacaaat cctccagcac agcctacatg       300
cagctcagca gcctgacatc tgaggactct gcggtctatt actgtgcaag gggggactac     360
tggggccaag gcaccactct cacagtcctc tcacccaacg acaccccaa aggttttgg       420 gaatctgtct                                                             430

<210> SEQ ID NO 50
<211> LENGTH: 414
<212> TYPE: DNA
<213> ORGANISM: Artificial Sequence
<220> FEATURE:
<223> OTHER INFORMATION: Synthetic polynucleotide

<400> SEQUENCE: 50
atgggatgga gctgtatcat cctcttcttg gtatcaacag ctacaggtgt ccactcccag      60
gtccaactgc agcagcctgg ggctgagctt gtgaagcctg ggcttcagt gaagctgtcc       120 tgcaaggctt ctggctacac cttcaccagc tactggatgc actgggtgaa gcagaggcct      180
```

```
ggacaaggcc ttgagtggat cggagagatt gatccttctg atagttatac taagtacaat    240
caaaagttca agggcaaggc cacattgact gtagacaaat catccagcac agcctacatg    300
cagctcagca gcctgacatc tgaggactct gcggtctatt actgtgcaag ggggactac     360 tggggccaag gcaccattct cagagtctcc tcagccaaaa cgacaccccc atct          414

<210> SEQ ID NO 51
<211> LENGTH: 456
<212> TYPE: DNA
<213> ORGANISM: Artificial Sequence
<220> FEATURE:
<223> OTHER INFORMATION: Synthetic polynucleotide

<400> SEQUENCE: 51
atgggatgga gctgtatcat cctcttcttg gtatcaacag ctacaggtgt ccactcccag     60
gtccaactgc agcagcctgg ggctgagctt gtgaagcctg ggcttcagt gaagctgtcc    120 tgcaaggctt ctggctacac cttcaccagc tactggatgc actgggtgaa gcagaggcct    180
ggacaaggcc ttgagtggat cggagagatt gatccttctg atagttatac tgactacaat    240
caaaatttca agggcaaggc cacattgact gtagacaaat cctccagcac agcctacatg    300
cagctcagca gcctgacatc tgaggactct gcggtctatt actgtgcaag ggggactac     360 tggggccaag gcaccactct cacagtctcc tcagccaaaa caacaccccc atcagtctat    420
ccactggccc ctgaatcgaa ttcctagtga attcgg                              456

<210> SEQ ID NO 52
<211> LENGTH: 439
<212> TYPE: DNA
<213> ORGANISM: Artificial Sequence
<220> FEATURE:
<223> OTHER INFORMATION: Synthetic polynucleotide

<400> SEQUENCE: 52
atgctgttgg ggctgaagtg ggttttcttt gttgtttttt atcaaggtgt gcattgtgag     60
gtgcagcttg ttgagactgg tggaggattg gtgcagccta agggtcatt gaaactctca    120 tgtgcagcct ctggattcac cttcaatacc aatgccatga actgggtccg ccaggctcca    180
ggaaagggtt tggaatgggt tgctcgcata agaagtaaaa gtaataatta tgcaacatat    240
tatgccgatt cagtgaaaga caggttcacc atctccagag atgattcaca aagcatgctc    300
tatctgcaaa tgaacaactt gaaaactgag gacacagcca tgtattactg tgtgagagat    360
ggttactatt cttactgggg ccaagggact ctggtcactg tctctgcagc tacaacaaca    420
gccccatctg tctatccct                                                 439

<210> SEQ ID NO 53
<211> LENGTH: 460
<212> TYPE: DNA
<213> ORGANISM: Artificial Sequence
<220> FEATURE:
<223> OTHER INFORMATION: Synthetic polynucleotide

<400> SEQUENCE: 53
atgggatgga gctatatcat cctctttttg gtagcaacag ctacagatgt ccactcccag     60
gtccaactgc agcagcctgg ggctgaactg gtgaagcctg ggcttcagt gaagctgtcc    120 tgcaaggctt ctggctacac cttcaccagc tactggatgc actgggtgaa acagaggcct    180
ggacaaggcc ttgagtggat tgagagatt aatcctagca acggtcgtac taactacaat    240
gaaaagttca gagcaaggc cacactgact gtagacaaat cctccagcac agcctacatg    300
```

```
caactcagca gcctgacatc tgaggactct gcggtctatt actgtgcaag atcgaggtac    360
tacggtagtt gctactttga ctactggggc caaggcacca ctctcacagt ctcctcagcc    420
aaaacaacac ccccatcagt ctatccactg gcccctgaat                          460
```

<210> SEQ ID NO 54
<211> LENGTH: 834
<212> TYPE: DNA
<213> ORGANISM: Artificial Sequence
<220> FEATURE:
<223> OTHER INFORMATION: Synthetic polynucleotide

<400> SEQUENCE: 54

```
atggactaca aagatgttgt gatgacccag actccactca ctttgtcggt taccattgga    60
caaccagcct ccatctcttg caagtcaagt cagagcctcc tagatagtga tggaaagaca    120
tatttgaatt ggttgttaca gaggccaggc cagtctccaa agcgcctaat ctatctggtg    180
tctaaactgg actctggagt ccctgacagg ttcactggca gtggatcagg gacagatttc    240
acactgaaaa tcagcagagt ggaggctgag gatttgggag tttattattg ctggcaaggt    300
acacattttc ctcggacgtt cggtggaggc accaagctgg aaatcaaacg gcctaacggc    360
gcgagcaaca gtagttctgc tccggaaact agttctgctt cgggatccca ggtccaactg    420
cagcagcctg ggctgagct tgtgaagcct ggggcttcag tgaagctgtc ctgcaaggct    480
tctggctaca ccttcaccag ctactggatg cactgggtga agcagaggcc tggacaaggc    540
cttgagtgga tcgagagat tgatccttct gatagttata ctaagtacaa tcaaaagttc    600
aagggcaagg ccacattgac tgtagacaaa tcctccagca cagcctacat gcagctcagc    660
agcctgacat ctgaggactc tgcggtctat tactgtgcaa gggggggacta ctggggccaa    720 ggcaccactc tcacagtcct ctcatctgac tacaaggacg acgacgacaa ggctagccag    780
ccagaactcg ccccggaaga ccccgaggat gtcgagcacc accaccacca ccac          834
```

<210> SEQ ID NO 55
<211> LENGTH: 101
<212> TYPE: PRT
<213> ORGANISM: Artificial Sequence
<220> FEATURE:
<223> OTHER INFORMATION: Synthetic human mortalin polypeptide

<400> SEQUENCE: 55

```
Glu Ala Ala Glu Lys Ala Lys Cys Glu Leu Ser Ser Ser Val Gln Thr
1               5                   10                  15

Asp Ile Asn Leu Pro Tyr Leu Thr Met Asp Ser Ser Gly Pro Lys His
            20                  25                  30

Leu Asn Met Lys Leu Thr Arg Ala Gln Phe Glu Gly Ile Val Thr Asp
        35                  40                  45

Leu Ile Arg Arg Thr Ile Ala Pro Cys Gln Lys Ala Met Gln Asp Ala
    50                  55                  60

Glu Val Ser Lys Ser Asp Ile Gly Glu Val Ile Leu Val Gly Gly Met
65                  70                  75                  80

Thr Arg Met Pro Lys Val Gln Gln Thr Val Gln Asp Leu Phe Gly Arg
                85                  90                  95

Ala Pro Ser Lys Ala
            100
```

<210> SEQ ID NO 56
<211> LENGTH: 30
<212> TYPE: PRT

-continued

```
<213> ORGANISM: Artificial Sequence
<220> FEATURE:
<223> OTHER INFORMATION: Synthetic mouse mortalin polypeptide

<400> SEQUENCE: 56

Gly Glu Val Ile Leu Val Gly Gly Met Thr Arg Met Pro Lys Val Gln
1               5                   10                  15

Gln Thr Val Gln Asp Leu Phe Gly Arg Ala Pro Ser Lys Ala
            20                  25                  30

<210> SEQ ID NO 57
<211> LENGTH: 679
<212> TYPE: PRT
<213> ORGANISM: Homo sapiens

<400> SEQUENCE: 57

Met Ile Ser Ala Ser Arg Ala Ala Ala Ala Arg Leu Val Gly Ala Ala
1               5                   10                  15

Ala Ser Arg Gly Pro Thr Ala Ala Arg His Gln Asp Ser Trp Asn Gly
            20                  25                  30

Leu Ser His Glu Ala Phe Arg Leu Val Ser Arg Arg Asp Tyr Ala Ser
        35                  40                  45

Glu Ala Ile Lys Gly Ala Val Val Gly Ile Asp Leu Gly Thr Thr Asn
    50                  55                  60

Ser Cys Val Ala Val Met Glu Gly Lys Gln Ala Lys Val Leu Glu Asn
65                  70                  75                  80

Ala Glu Gly Ala Arg Thr Thr Pro Ser Val Val Ala Phe Thr Ala Asp
                85                  90                  95

Gly Glu Arg Leu Val Gly Met Pro Ala Lys Arg Gln Ala Val Thr Asn
            100                 105                 110

Pro Asn Asn Thr Phe Tyr Ala Thr Lys Arg Leu Ile Gly Arg Arg Tyr
        115                 120                 125

Asp Asp Pro Glu Val Gln Lys Asp Ile Lys Asn Val Pro Phe Lys Ile
    130                 135                 140

Val Arg Ala Ser Asn Gly Asp Ala Trp Val Glu Ala His Gly Lys Leu
145                 150                 155                 160

Tyr Ser Pro Ser Gln Ile Gly Ala Phe Val Leu Met Lys Met Lys Glu
                165                 170                 175

Thr Ala Glu Asn Tyr Leu Gly His Thr Ala Lys Asn Ala Val Ile Thr
            180                 185                 190

Val Pro Ala Tyr Phe Asn Asp Ser Gln Arg Gln Ala Thr Lys Asp Ala
        195                 200                 205

Gly Gln Ile Ser Gly Leu Asn Val Leu Arg Val Ile Asn Glu Pro Thr
    210                 215                 220

Ala Ala Ala Leu Ala Tyr Gly Leu Asp Lys Ser Glu Asp Lys Val Ile
225                 230                 235                 240

Ala Val Tyr Asp Leu Gly Gly Gly Thr Phe Asp Ile Ser Ile Leu Glu
                245                 250                 255

Ile Gln Lys Gly Val Phe Glu Val Lys Ser Thr Asn Gly Asp Thr Phe
            260                 265                 270

Leu Gly Gly Glu Asp Phe Asp Gln Ala Leu Leu Arg His Ile Val Lys
        275                 280                 285

Glu Phe Lys Arg Glu Thr Gly Val Asp Leu Thr Lys Asp Asn Met Ala
    290                 295                 300

Leu Gln Arg Val Arg Glu Ala Glu Lys Ala Lys Cys Glu Leu Ser
305                 310                 315                 320
```

```
Ser Ser Val Gln Thr Asp Ile Asn Leu Pro Tyr Leu Thr Met Asp Ser
            325                 330                 335

Ser Gly Pro Lys His Leu Asn Met Lys Leu Thr Arg Ala Gln Phe Glu
            340                 345                 350

Gly Ile Val Thr Asp Leu Ile Arg Arg Thr Ile Ala Pro Cys Gln Lys
            355                 360                 365

Ala Met Gln Asp Ala Glu Val Ser Lys Ser Asp Ile Gly Glu Val Ile
        370                 375                 380

Leu Val Gly Gly Met Thr Arg Met Pro Lys Val Gln Gln Thr Val Gln
385                 390                 395                 400

Asp Leu Phe Gly Arg Ala Pro Ser Lys Ala Val Asn Pro Asp Glu Ala
            405                 410                 415

Val Ala Ile Gly Ala Ala Ile Gln Gly Gly Val Leu Ala Gly Asp Val
            420                 425                 430

Thr Asp Val Leu Leu Leu Asp Val Thr Pro Leu Ser Leu Gly Ile Glu
        435                 440                 445

Thr Leu Gly Gly Val Phe Thr Lys Leu Ile Asn Arg Asn Thr Thr Ile
    450                 455                 460

Pro Thr Lys Lys Ser Gln Val Phe Ser Thr Ala Ala Asp Gly Gln Thr
465                 470                 475                 480

Gln Val Glu Ile Lys Val Cys Gln Gly Glu Arg Glu Met Ala Gly Asp
            485                 490                 495

Asn Lys Leu Leu Gly Gln Phe Thr Leu Ile Gly Ile Pro Pro Ala Pro
            500                 505                 510

Arg Gly Val Pro Gln Ile Glu Val Thr Phe Asp Ile Asp Ala Asn Gly
            515                 520                 525

Ile Val His Val Ser Ala Lys Asp Lys Gly Thr Gly Arg Glu Gln Gln
        530                 535                 540

Ile Val Ile Gln Ser Ser Gly Gly Leu Ser Lys Asp Asp Ile Glu Asn
545                 550                 555                 560

Met Val Lys Asn Ala Glu Lys Tyr Ala Glu Asp Arg Arg Lys Lys
            565                 570                 575

Glu Arg Val Glu Ala Val Asn Met Ala Glu Gly Ile Ile His Asp Thr
            580                 585                 590

Glu Thr Lys Met Glu Glu Phe Lys Asp Gln Leu Pro Ala Asp Glu Cys
            595                 600                 605

Asn Lys Leu Lys Glu Glu Ile Ser Lys Met Arg Glu Leu Leu Ala Arg
        610                 615                 620

Lys Asp Ser Glu Thr Gly Glu Asn Ile Arg Gln Ala Ala Ser Ser Leu
625                 630                 635                 640

Gln Gln Ala Ser Leu Lys Leu Phe Glu Met Ala Tyr Lys Lys Met Ala
            645                 650                 655

Ser Glu Arg Glu Gly Ser Gly Ser Ser Gly Thr Gly Glu Gln Lys Glu
            660                 665                 670

Asp Gln Lys Glu Glu Lys Gln
        675

<210> SEQ ID NO 58
<211> LENGTH: 2845
<212> TYPE: DNA
<213> ORGANISM: Homo sapiens

<400> SEQUENCE: 58
ggtttccaga agcgctgccg ccaccgcatc gcgcagctct tgccgtcgg agcgcttgtt      60 tgctgcctcg tactcctcca tttatccgcc atgataagtg ccagccgagc tgcagcagcc    120
```

```
cgtctcgtgg gcgccgcagc ctcccggggc cctacggccg cccgccacca ggatagctgg    180
aatggcctta gtcatgaggc ttttagactt gtttcaaggc gggattatgc atcagaagca    240
atcaagggag cagttgttgg tattgatttg ggtactacca actcctgcgt ggcagttatg    300
gaaggtaaac aagcaaaggt gctggagaat gctgaaggtg ccagaaccac cccttcagtt    360 gtggcccttta cagcagatgg tgagcgactt gttggaatgc cggccaagcg acaggctgtc    420
accaacccaa acaatacatt ttatgctacc aagcgtctca ttggccggcg atatgatgat    480
cctgaagtac agaaagacat taaaaatgtt ccctttaaaa ttgtccgtgc ctccaatggt    540
gatgcctggg ttgaggctca tgggaaattg tattctccga gtcagattgg agcatttgtg    600
ttgatgaaga tgaaagagac tgcagaaaat tacttgggc acacagcaaa aaatgctgtg    660
atcacagtcc cagcttattt caatgactcg cagagacagg ccactaaaga tgctggccag    720
atatctggac tgaatgtgct tcgggtgatt aatgagccca cagctgctgc tcttgcctat    780
ggtctagaca aatcagaaga caaagtcatt gctgtatatg atttaggtgg tggaactttt    840
gatatttcta tcctggaaat tcagaaagga gtatttgagg tgaaatccac aaatggggat    900
accttcttag gtgggaaga ctttgaccag gccttgctac ggcacattgt gaaggagttc    960
aagagagaga caggggttga tttgactaaa gacaacatgg cacttcagag ggtacgggaa   1020
gctgctgaaa aggctaaatg tgaactctcc tcatctgtgc agactgacat caatttgccc   1080
tatcttacaa tggattcttc tggacccaag catttgaata tgaagttgac ccgtgctcaa   1140
tttgaaggga ttgtcactga tctaatcaga aggactatcg ctccatgcca aaaagctatg   1200
caagatgcag aagtcagcaa gagtgacata ggagaagtga ttcttgtggg tggcatgact   1260
aggatgccca aggttcagca gactgtacag gatcttttg gcagagcccc aagtaaagct   1320
gtcaatcctg atgaggctgt ggccattgga gctgccattc agggaggtgt gttggccggc   1380
gatgtcacgg atgtgctgct ccttgatgtc actcccctgt ctctgggtat tgaaactcta   1440
ggaggtgtct ttaccaaact tattaatagg aataccacta ttccaaccaa gaagagccag   1500
gtattctcta ctgccgctga tggtcaaacg caagtggaaa ttaaagtgtg tcagggtgaa   1560
agagagatgg ctggagacaa caaactcctt ggacagttta ctttgattgg aattccacca   1620
gcccctcgtg gagttcctca gattgaagtt acatttgaca ttgatgccaa tgggatagta   1680
catgtttctg ctaaagataa aggcacagga cgtgagcagc agattgtaat ccagtcttct   1740
ggtggattaa gcaaagatga tattgaaaat atggttaaaa atgcagagaa atatgctgaa   1800
gaagaccggc gaaagaagga acgagttgaa gcagttaata tggctgaagg aatcattcac   1860
gacacagaaa ccaagatgga agaattcaag gaccaattac ctgctgatga gtgcaacaag   1920 ctgaagaag agatttccaa aatgagggag ctcctggcta gaaaagacag cgaaacagga   1980
gaaaatatta gacaggcagc atcctctctt cagcaggcat cattgaagct gttcgaaatg    2040
gcatacaaaa agatggcatc tgagcgagaa ggctctggaa gttctggcac tggggaacaa   2100
aaggaagatc aaaaggagga aaacagtaa taatagcaga aattttgaag ccagaaggac    2160
aacatatgaa gcttaggagt gaagagactt cctgagcaga atgggcgaa cttcagtctt    2220 tttactgtgt ttttgcagta ttctatatat aatttcctta atttgtaaat ttagtgacca   2280
ttagctagtg atcatttaat ggacagtgat tctaacagta taaagttcac aatattctat   2340
gtccctagcc tgtcattttt cagctgcatg taaaggagg taggatgaat tgatcattat    2400
aaagatttaa ctattttatg ctgaagtgac catatttca aggggtgaaa ccatctcgca   2460
cacagcaatg aaggtagtca tccatagact tgaaatgaga ccacatatgg ggatgagatc   2520
```

```
cttctagtta gcctagtact gctgtactgg cctgtatgta catggggtcc ttcaactgag    2580
gccttgcaag tcaagctggc tgtgccatgt ttgtagatgg ggcagaggaa tctagaacaa    2640
tgggaaactt agctatttat attaggtaca gctattaaaa caaggtagga atgaggctag    2700
acctttaact tccctaaggc atactttttct agctaccttc tgccctgtgt ctggcaccta    2760
catccttgat gattgttctc ttacccattc tggaattttt ttttttttaa ataaatacag    2820
aaagcaaaaa aaaaaaaaaa aaaaa                                          2845

<210> SEQ ID NO 59
<211> LENGTH: 303
<212> TYPE: DNA
<213> ORGANISM: Artificial Sequence
<220> FEATURE:
<223> OTHER INFORMATION: Synthetic polynucleotide

<400> SEQUENCE: 59
gaagctgctg aaaaggctaa atgtgaactc tcctcatctg tgcagactga catcaatttg     60
ccctatctta caatggattc ttctggaccc aagcatttga atatgaagtt gacccgtgct    120
caatttgaag ggattgtcac tgatctaatc agaaggacta cgctccatg ccaaaaagct    180 atgcaagatg cagaagtcag caagagtgac ataggagaag tgattcttgt gggtggcatg    240
actaggatgc caaggttca gcagactgta caggatcttt ttggcagagc cccaagtaaa    300
gct                                                                  303

<210> SEQ ID NO 60
<211> LENGTH: 90
<212> TYPE: DNA
<213> ORGANISM: Artificial Sequence
<220> FEATURE:
<223> OTHER INFORMATION: Synthetic polynucleotide

<400> SEQUENCE: 60
ggagaagtga ttcttgtggg tggcatgact aggatgccca aggttcagca gactgtacag     60 gatcttttg gcagagcccc aagtaaagct                                       90

<210> SEQ ID NO 61
<211> LENGTH: 679
<212> TYPE: PRT
<213> ORGANISM: Mus musculus

<400> SEQUENCE: 61

Met Ile Ser Ala Ser Arg Ala Ala Ala Ala Arg Leu Val Gly Thr Ala
1               5                   10                  15

Ala Ser Arg Ser Pro Ala Ala Ala Arg Pro Gln Asp Gly Trp Asn Gly
            20                  25                  30

Leu Ser His Glu Ala Phe Arg Phe Val Ser Arg Arg Asp Tyr Ala Ser
        35                  40                  45

Glu Ala Ile Lys Gly Ala Val Val Gly Ile Asp Leu Gly Thr Thr Asn
    50                  55                  60

Ser Cys Val Ala Val Met Glu Gly Lys Gln Ala Lys Val Leu Glu Asn
65                  70                  75                  80

Ala Glu Gly Ala Arg Thr Thr Pro Ser Val Val Ala Phe Thr Ala Asp
                85                  90                  95

Gly Glu Arg Leu Val Gly Met Pro Ala Lys Arg Gln Ala Val Thr Asn
            100                 105                 110

Pro Asn Asn Thr Phe Tyr Ala Thr Lys Arg Ile Ile Gly Arg Arg Tyr
        115                 120                 125
```

```
Asp Asp Pro Glu Val Gln Lys Asp Thr Lys Asn Val Pro Phe Lys Ile
    130                 135                 140
Val Arg Ala Ser Asn Gly Asp Ala Trp Val Glu Ala His Gly Lys Leu
145                 150                 155                 160
Tyr Ser Pro Ser Gln Ile Gly Ala Phe Val Leu Met Lys Met Lys Glu
                165                 170                 175
Thr Ala Glu Asn Tyr Leu Gly His Thr Ala Lys Asn Ala Val Ile Thr
            180                 185                 190
Val Pro Ala Tyr Phe Asn Asp Ser Gln Arg Gln Ala Thr Lys Asp Ala
        195                 200                 205
Gly Gln Ile Ser Gly Leu Asn Val Leu Arg Val Ile Asn Glu Pro Thr
    210                 215                 220
Ala Ala Ala Leu Ala Tyr Gly Leu Asp Lys Ser Glu Asp Lys Val Ile
225                 230                 235                 240
Ala Val Tyr Asp Leu Gly Gly Gly Thr Phe Asp Ile Ser Ile Leu Glu
                245                 250                 255
Ile Gln Lys Gly Val Phe Glu Val Lys Ser Thr Asn Gly Asp Thr Phe
            260                 265                 270
Leu Gly Gly Glu Asp Phe Asp Gln Ala Leu Leu Arg His Ile Val Lys
        275                 280                 285
Glu Phe Lys Arg Glu Thr Gly Val Asp Leu Thr Lys Asp Asn Met Ala
    290                 295                 300
Leu Gln Arg Val Arg Glu Ala Ala Glu Lys Ala Lys Cys Glu Leu Ser
305                 310                 315                 320
Ser Ser Val Gln Thr Asp Ile Asn Leu Pro Tyr Leu Thr Met Asp Ala
                325                 330                 335
Ser Gly Pro Lys His Leu Asn Met Lys Leu Thr Arg Ala Gln Phe Glu
            340                 345                 350
Gly Ile Val Thr Asp Leu Ile Lys Arg Thr Ile Ala Pro Cys Gln Lys
        355                 360                 365
Ala Met Gln Asp Ala Glu Val Ser Lys Ser Asp Ile Gly Glu Val Ile
    370                 375                 380
Leu Val Gly Gly Met Thr Arg Met Pro Lys Val Gln Gln Thr Val Gln
385                 390                 395                 400
Asp Leu Phe Gly Arg Ala Pro Ser Lys Ala Val Asn Pro Asp Glu Ala
                405                 410                 415
Val Ala Ile Gly Ala Ala Ile Gln Gly Gly Val Leu Ala Gly Asp Val
            420                 425                 430
Thr Asp Val Leu Leu Leu Asp Val Thr Pro Leu Ser Leu Gly Ile Glu
        435                 440                 445
Thr Leu Gly Gly Val Phe Thr Lys Leu Ile Asn Arg Asn Thr Thr Ile
    450                 455                 460
Pro Thr Lys Lys Ser Gln Val Phe Ser Thr Ala Ala Asp Gly Gln Thr
465                 470                 475                 480
Gln Val Glu Ile Lys Val Cys Gln Gly Glu Arg Glu Met Ala Gly Asp
                485                 490                 495
Asn Lys Leu Leu Gly Gln Phe Thr Leu Ile Gly Ile Pro Pro Ala Pro
            500                 505                 510
Arg Gly Val Pro Gln Ile Glu Val Thr Phe Asp Ile Asp Ala Asn Gly
        515                 520                 525
Ile Val His Val Ser Ala Lys Asp Lys Gly Thr Gly Arg Glu Gln Gln
    530                 535                 540
Ile Val Ile Gln Ser Ser Gly Gly Leu Ser Lys Asp Asp Ile Glu Asn
```

```
                545                 550                 555                 560
Met Val Lys Asn Ala Glu Lys Tyr Ala Glu Glu Asp Arg Arg Lys Lys
                    565                 570                 575

Glu Arg Val Glu Ala Val Asn Met Ala Glu Gly Ile Ile His Asp Thr
                580                 585                 590

Glu Thr Lys Met Glu Glu Phe Lys Asp Gln Leu Pro Ala Asp Glu Cys
            595                 600                 605

Asn Lys Leu Lys Glu Glu Ile Ser Lys Met Arg Ala Leu Leu Ala Gly
                610                 615                 620

Lys Asp Ser Glu Thr Gly Glu Asn Ile Arg Gln Ala Ala Ser Ser Leu
625                 630                 635                 640

Gln Gln Ala Ser Leu Lys Leu Phe Glu Met Ala Tyr Lys Lys Met Ala
                    645                 650                 655

Ser Glu Arg Glu Gly Ser Gly Ser Ser Gly Thr Gly Glu Gln Lys Glu
                660                 665                 670

Asp Gln Lys Glu Glu Lys Gln
            675

<210> SEQ ID NO 62
<211> LENGTH: 101
<212> TYPE: PRT
<213> ORGANISM: Artificial Sequence
<220> FEATURE:
<223> OTHER INFORMATION: Synthetic mouse mortalin polypeptide

<400> SEQUENCE: 62

Glu Ala Ala Glu Lys Ala Lys Cys Glu Leu Ser Ser Val Gln Thr
1               5                   10                  15

Asp Ile Asn Leu Pro Tyr Leu Thr Met Asp Ala Ser Gly Pro Lys His
                20                  25                  30

Leu Asn Met Lys Leu Thr Arg Ala Gln Phe Glu Gly Ile Val Thr Asp
            35                  40                  45

Leu Ile Lys Arg Thr Ile Ala Pro Cys Gln Lys Ala Met Gln Asp Ala
        50                  55                  60

Glu Val Ser Lys Ser Asp Ile Gly Glu Val Ile Leu Val Gly Gly Met
65                  70                  75                  80

Thr Arg Met Pro Lys Val Gln Gln Thr Val Gln Asp Leu Phe Gly Arg
                    85                  90                  95

Ala Pro Ser Lys Ala
            100

<210> SEQ ID NO 63
<211> LENGTH: 2996
<212> TYPE: DNA
<213> ORGANISM: Mus musculus

<400> SEQUENCE: 63
caccaccgtg cacgcagctc cgggcccgtg ggtgttggtt cttgccctcg taaccccctc      60
tgtccagcca ccatgataag cgccagcaga gccgcggccg cgcgtctcgt gggcaccgct     120
gcgtcccgga gccccgcagc cgcccgtccc caggatggct ggaatggcct tagccatgag     180
gcttttagat ttgtttcaag aagagattat gcatcagaag caatcaaggg tgcagtggtt     240
ggtattgatt gggtactact aactcctgtg tggctgttat ggagggcaa acaagcaaag      300 gtcctggaga atgctgaagg tgccagaact accccttctg tggttgcctt tacagcagat     360
ggagaacgac ttgttggtat gccagcaaaa cggcaagctg tcaccaatcc aaacaatacc     420
ttctatgcta ctaagcgtat tattggacga cgatatgatg accctgaagt acagaaagac     480
```

```
actaagaatg ttcctttaa aattgtccgt gcctccaatg gtgatgcttg ggttgaggct      540
catggaaaac tctattctcc aagtcagatt ggagcatttg tgttgatgaa gatgaaagag      600
actgcagaaa attacttggg ccacacagca aaaaatgctg tgatcacagt ccctgcttat      660
ttcaatgatt cacagcgaca ggccactaag gatgctggcc agatatctgg gctaaatgtg      720
cttcgagtga tcaatgagcc tacagctgct gctctagctt acggtctgga caaatctgaa      780
gataaagtca ttgctgtgta tgatttaggt ggtggaacct ttgacatttc tatcctggaa      840
attcagaaag gagtgtttga ggtgaaatct accaatgggg acactttctt aggaggggaa      900
gactttgacc aagctttgtt gcggcacatt gtcaaggagt tcaagagaga gacagggtt       960 gatttgacca agacaacat ggcgcttcag agggttcggg aagctgctga aaggctaaa       1020 tgtgaacttt cctcatctgt gcagactgac atcaacttgc cataccttac catggatgct     1080
tctggaccaa agcatttgaa tatgaagctg actcgagctc agtttgaagg cattgtcaca     1140
gatctaatca agagaactat tgctccgtgt cagaaagcta tgcaggatgc agaagtcagc     1200
aagagtgaca taggagaagt gattctggtt ggtggcatga caaggatgcc caaggttcag     1260
cagactgtac aagatctttt tggcagagcc ccgagtaaag ctgttaatcc tgatgaggct     1320
gtagccatcg gagctgccat ccagggaggt gtgttggctg gtgacgttac agacgtgctg     1380
ctcctggatg tcactcccct ctctctgggt attgagactc tgggaggcgt ctttaccaaa     1440
cttattaata ggaacaccac tattccaacc aaaaagagcc aggtgttttc tactgctgct     1500
gatggacaaa ctcaagtaga gattaaagtg tgtcagggg aacgagagat ggctggagac     1560
aacaaacttc taggacagtt cactttgatt ggaattcccc cagcccctcg tggagtgccc     1620
cagattgaag ttacatttga cattgatgcc aatgggatt tgcacgtttc tgccaaagat      1680
aaaggcactg gtcgtgagca acagattgta atccagtctt ctggtggatt aagcaaagat     1740
gatattgaaa atatggttaa aaatgcagag aagtacgctg aggaagaccg caggaagaag     1800
gaacgtgttg aagcagttaa tatggctgaa ggaattattc atgacacaga aaccaagatg     1860
gaagaattta aggaccagtt gcctgctgat gagtgcaaca agctaaagga agagatttcc     1920
aaaatgagag cgctccttgc tggaaaggac agtgagacag gagagaacat caggcaggca     1980
gcatcttccc tacagcaggc gtcattgaaa ctcttcgaaa tggcgtacaa aaagatggca     2040
tctgaacggg aaggttctgg aagttctggc actggggaac agaaggaaga tcagaaggaa     2100
gagaaacagt aatcgtggca gtgcattgtg gagccagaag gacatactat gaagcttggg     2160
actaaaggga cttcctgagc agaaaagggg cagacttcag tcttttttact gtattttgc      2220 agtattctat atataatttc cttaatatat aaacttagtg acaattgcta actcatttaa     2280
tgggtaataa agtcagcaat agcaggttca tactgttctg tcactagcct gttattttca     2340
gctgcatgta aaggggtggg atggggctgt gaaccaatca ttaaggtaga tttggttttgt    2400 gctgaaatgg ctgtgatttc aaggtgggaa gcccatttca catgcagtgg aggtagtctg     2460
tcattgacct tgaattgaga tcatatgcag atgcttgttg gccaagagca ctactataaa     2520
gaatgacctc tgtatatttg ctcctacaac taatgccttt aagactgagc tacctgtacc     2580
atggtctgta ggtgcagaag ctaggtcagt ggatagcagt tgtgttagcc atagcttaaa     2640
gtatgatatg agaatgatat aagcctctca tgggcctgag gcatacttct ctagccaccc     2700
tcttggttgg ccaatgtctg gcatctgtat tcttgatgat tgttccttt tcatccactc      2760 tggatttttt aaataaaatt ctgaaagcct cttgatctcc tttgtgaatg gtgatagctc     2820
aaggattatg actgctatca gttttgtagg gagaaaaatc actggctaaa aggttgaaca     2880
```

-continued aatgaaacat ggggagtgac taataaaatg ctggcatata tgctggatgt gaaagtccac    2940
tcaggaagca gtttgaagcc aggcagggct gtacagttaa ctccgtctta ataaaa         2996

<210> SEQ ID NO 64
<211> LENGTH: 303
<212> TYPE: DNA
<213> ORGANISM: Artificial Sequence
<220> FEATURE:
<223> OTHER INFORMATION: Synthetic polynucleotide

<400> SEQUENCE: 64
gaagctgctg agaaggctaa atgtgaactt tcctcatctg tgcagactga catcaacttg     60
ccatacctta ccatggatgc ttctggacca aagcatttga atatgaagct gactcgagct    120
cagtttgaag gcattgtcac agatctaatc aagagaacta ttgctccgtg tcagaaagct    180
atgcaggatg cagaagtcag caagagtgac ataggagaag tgattctggt tggtggcatg    240
acaaggatgc ccaaggttca gcagactgta caagatcttt ttggcagagc cccgagtaaa    300
gct                                                                 303

<210> SEQ ID NO 65
<211> LENGTH: 90
<212> TYPE: DNA
<213> ORGANISM: Artificial Sequence
<220> FEATURE:
<223> OTHER INFORMATION: Synthetic polynucleotide

<400> SEQUENCE: 65
ggagaagtga ttctggttgg tggcatgaca aggatgccca aggttcagca gactgtacaa     60
gatctttttg gcagagcccc gagtaaagct                                     90

<210> SEQ ID NO 66
<211> LENGTH: 6
<212> TYPE: PRT
<213> ORGANISM: Artificial Sequence
<220> FEATURE:
<223> OTHER INFORMATION: Synthetic oligopeptide

<400> SEQUENCE: 66

Leu Phe Gly Arg Ala Pro
1               5

<210> SEQ ID NO 67
<211> LENGTH: 15
<212> TYPE: PRT
<213> ORGANISM: Artificial Sequence
<220> FEATURE:
<223> OTHER INFORMATION: Synthetic oligopeptide

<400> SEQUENCE: 67

Pro Lys Val Gln Gln Thr Val Gln Asp Leu Phe Gly Arg Ala Pro
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Synthetic oligopeptide

<400> SEQUENCE: 68

Lys Val Gln Gln Thr Val Gln Asp Leu Phe Gly Arg Ala Pro Ser
1               5                   10                  15

-continued

```
<210> SEQ ID NO 69
<211> LENGTH: 15
<212> TYPE: PRT
<213> ORGANISM: Artificial Sequence
<220> FEATURE:
<223> OTHER INFORMATION: Synthetic oligopeptide

<400> SEQUENCE: 69

Val Gln Gln Thr Val Gln Asp Leu Phe Gly Arg Ala Pro Ser Lys
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: Synthetic oligopeptide

<400> SEQUENCE: 70

Gln Gln Thr Val Gln Asp Leu Phe Gly Arg Ala Pro Ser Lys Ala
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Synthetic oligopeptide

<400> SEQUENCE: 71

Gln Thr Val Gln Asp Leu Phe Gly Arg Ala Pro Ser Lys Ala Val
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Synthetic oligopeptide

<400> SEQUENCE: 72

Thr Val Gln Asp Leu Phe Gly Arg Ala Pro Ser Lys Ala Val Asn
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Synthetic oligopeptide

<400> SEQUENCE: 73

Val Gln Asp Leu Phe Gly Arg Ala Pro Ser Lys Ala Val Asn Pro
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Synthetic oligopeptide

<400> SEQUENCE: 74

Gln Asp Leu Phe Gly Arg Ala Pro Ser Lys Ala Val Asn Pro Asp
1               5                   10                  15

<210> SEQ ID NO 75
```

```
<211> LENGTH: 15
<212> TYPE: PRT
<213> ORGANISM: Artificial Sequence
<220> FEATURE:
<223> OTHER INFORMATION: Synthetic oligopeptide

<400> SEQUENCE: 75

Asp Leu Phe Gly Arg Ala Pro Ser Lys Ala Val Asn Pro Asp Glu
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Synthetic oligopeptide

<400> SEQUENCE: 76

Leu Phe Gly Arg Ala Pro Ser Lys Ala Val Asn Pro Asp Glu Ala
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: Synthetic oligopeptide

<400> SEQUENCE: 77

Lys Ala Met Gln Asp Ala Glu Val Ser Lys Ser Asp Ile Gly Glu
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Synthetic oligopeptide

<400> SEQUENCE: 78

Gly Glu Val Ile Leu Val Gly Gly Met Thr Arg Met Pro Lys Val
1               5                   10                  15

<210> SEQ ID NO 79
<211> LENGTH: 14
<212> TYPE: PRT
<213> ORGANISM: Artificial Sequence
<220> FEATURE:
<223> OTHER INFORMATION: Synthetic oligopeptide

<400> SEQUENCE: 79

Glu Val Ile Leu Val Gly Gly Met Thr Arg Met Pro Lys Val
1               5                   10

<210> SEQ ID NO 80
<211> LENGTH: 15
<212> TYPE: PRT
<213> ORGANISM: Artificial Sequence
<220> FEATURE:
<223> OTHER INFORMATION: Synthetic oligopeptide

<400> SEQUENCE: 80

Gly Met Thr Arg Met Pro Lys Val Gln Gln Thr Val Gln Asp Leu
1               5                   10                  15

<210> SEQ ID NO 81
<211> LENGTH: 15
<212> TYPE: PRT
```

<213> ORGANISM: Artificial Sequence
<220> FEATURE:
<223> OTHER INFORMATION: Synthetic oligopeptide

<400> SEQUENCE: 81

```
Thr Arg Met Pro Lys Val Gln Gln Thr Val Gln Asp Leu Phe Gly
1               5                   10                  15
```

<210> SEQ ID NO 82
<211> LENGTH: 15
<212> TYPE: PRT
<213> ORGANISM: Artificial Sequence
<220> FEATURE:
<223> OTHER INFORMATION: Synthetic oligopeptide

<400> SEQUENCE: 82

```
Arg Met Pro Lys Val Gln Gln Thr Val Gln Asp Leu Phe Gly Arg
1               5                   10                  15
```

<210> SEQ ID NO 83
<211> LENGTH: 426
<212> TYPE: DNA
<213> ORGANISM: Artificial Sequence
<220> FEATURE:
<223> OTHER INFORMATION: Synthetic polynucleotide

<400> SEQUENCE: 83

```
agatctcgat cccgcgaaat taatacgact cactataggg gaattgtgag cggataacaa      60
ttcccctcta gaaataattt tgtttaactt taagaaggag atatacatat gaaatacctg     120
ctgccgaccg ctgctgctgg tctgctgctc ctcgctgccc agccggcgat ggccatggat     180
atcggaatta attcggatcc gaattcgagc tccgtcgaca gcttgcggc cgcactcgag      240
atcaaacggg ctagccagcc agaactcgcc ccggaagacc ccgaggatgt cgagcaccac     300
caccaccacc actgagatcc ggctgctaac aaagcccgaa aggaagctga gttggctgct     360
gccaccgctg agcaataact agcataaccc cttggggcct ctaaacgggt cttgaggggt     420
tttttg                                                                426
```

<210> SEQ ID NO 84
<211> LENGTH: 68
<212> TYPE: PRT
<213> ORGANISM: Artificial Sequence
<220> FEATURE:
<223> OTHER INFORMATION: Synthetic polypeptide

<400> SEQUENCE: 84

```
Met Lys Tyr Leu Leu Pro Thr Ala Ala Ala Gly Leu Leu Leu Leu Ala
1               5                   10                  15

Ala Gln Pro Ala Met Ala Met Asp Ile Gly Ile Asn Ser Asp Pro Asn
                20                  25                  30

Ser Ser Ser Val Asp Lys Leu Ala Ala Ala Leu Glu Ile Lys Arg Ala
            35                  40                  45

Ser Gln Pro Glu Leu Ala Pro Glu Asp Pro Glu Asp Val Glu His His
        50                  55                  60

His His His His
65
```

<210> SEQ ID NO 85
<211> LENGTH: 780
<212> TYPE: DNA
<213> ORGANISM: Artificial Sequence
<220> FEATURE:
<223> OTHER INFORMATION: Synthetic polynucleotide

<400> SEQUENCE: 85

```
atggactaca aagatgttgt gatgacccag actccactca ctttgtcggt taccattgga      60
caaccagcct ccatctcttg caagtcaagt cagagcctcc tagatagtga tggaaagaca     120
tatttgaatt ggttgttaca gaggccaggc cagtctccaa agcgcctaat ctatctggtg     180
tctaaactgg actctggagt ccctgacagg ttcactggca gtggatcagg gacagatttc     240
acactgaaaa tcagcagagt ggaggctgag gatttgggag tttattattg ctggcaaggt     300
acacattttc ctcggacgtt cggtggaggc accaagctgg aaatcaaacg gcctaacggc     360
gcgagcaaca gtagttctgc tccggaaact agttctgctt cgggatccca ggtccaactg     420
cagcagcctg gggctgagct tgtgaagcct ggggcttcag tgaagctgtc ctgcaaggct     480
tctggctaca ccttcaccag ctactggatg cactgggtga agcagaggcc tggacaaggc     540
cttgagtgga tcggagagat tgatccttct gatagttata ctaagtacaa tcaaaagttc     600
aagggcaagg ccacattgac tgtagacaaa tcctccagca cagcctacat gcagctcagc     660
agcctgacat ctgaggactc tgcggtctat tactgtgcaa gggggggacta ctggggccaa     720
ggcaccactc tcacagtcct ctcatctgac tacaaggacg acgacgacaa ggctagctac     780
```

<210> SEQ ID NO 86
<211> LENGTH: 260
<212> TYPE: PRT
<213> ORGANISM: Artificial Sequence
<220> FEATURE:
<223> OTHER INFORMATION: Synthetic polypeptide

<400> SEQUENCE: 86

Met Asp Tyr Lys Asp Val Val Met Thr Gln Thr Pro Leu Thr Leu Ser
1               5                   10                  15

Val Thr Ile Gly Gln Pro Ala Ser Ile Ser Cys Lys Ser Ser Gln Ser
            20                  25                  30

Leu Leu Asp Ser Asp Gly Lys Thr Tyr Leu Asn Trp Leu Leu Gln Arg
        35                  40                  45

Pro Gly Gln Ser Pro Lys Arg Leu Ile Tyr Leu Val Ser Lys Leu Asp
    50                  55                  60

Ser Gly Val Pro Asp Arg Phe Thr Gly Ser Gly Ser Gly Thr Asp Phe
65                  70                  75                  80

Thr Leu Lys Ile Ser Arg Val Glu Ala Glu Asp Leu Gly Val Tyr Tyr
                85                  90                  95

Cys Trp Gln Gly Thr His Phe Pro Arg Thr Phe Gly Gly Gly Thr Lys
            100                 105                 110

Leu Glu Ile Lys Arg Pro Asn Gly Ala Ser Asn Ser Ser Ser Ala Pro
        115                 120                 125

Glu Thr Ser Ser Ala Ser Gly Ser Gln Val Gln Leu Gln Gln Pro Gly
    130                 135                 140

Ala Glu Leu Val Lys Pro Gly Ala Ser Val Lys Leu Ser Cys Lys Ala
145                 150                 155                 160

Ser Gly Tyr Thr Phe Thr Ser Tyr Trp Met His Trp Val Lys Gln Arg
                165                 170                 175

Pro Gly Gln Gly Leu Glu Trp Ile Gly Glu Ile Asp Pro Ser Asp Ser
            180                 185                 190

Tyr Thr Lys Tyr Asn Gln Lys Phe Lys Gly Lys Ala Thr Leu Thr Val
        195                 200                 205

Asp Lys Ser Ser Ser Thr Ala Tyr Met Gln Leu Ser Ser Leu Thr Ser
    210                 215                 220

```
Glu Asp Ser Ala Val Tyr Tyr Cys Ala Arg Gly Asp Tyr Trp Gly Gln
225                 230                 235                 240

Gly Thr Thr Leu Thr Val Leu Ser Ser Asp Tyr Lys Asp Asp Asp Asp
                245                 250                 255

Lys Ala Ser Tyr
            260

<210> SEQ ID NO 87
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 87

Arg Ala Gln Phe Glu Gly Ile Val Thr Asp Leu Ile Arg Arg Thr
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 88

Ala Gln Phe Glu Gly Ile Val Thr Asp Leu Ile Arg Arg Thr Ile
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 89

Gln Phe Glu Gly Ile Val Thr Asp Leu Ile Arg Arg Thr Ile Ala
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 90

Phe Glu Gly Ile Val Thr Asp Leu Ile Arg Arg Thr Ile Ala Pro
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 91

Glu Gly Ile Val Thr Asp Leu Ile Arg Arg Thr Ile Ala Pro Cys
1               5                   10                  15

<210> SEQ ID NO 92
<211> LENGTH: 15
<212> TYPE: PRT
<213> ORGANISM: Artificial Sequence
```

```
<220> FEATURE:
<223> OTHER INFORMATION: Synthetic polypeptide

<400> SEQUENCE: 92

Gly Ile Val Thr Asp Leu Ile Arg Arg Thr Ile Ala Pro Cys Gln
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 93

Ile Val Thr Asp Leu Ile Arg Arg Thr Ile Ala Pro Cys Gln Lys
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 94

Val Thr Asp Leu Ile Arg Arg Thr Ile Ala Pro Cys Gln Lys Ala
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 95

Thr Asp Leu Ile Arg Arg Thr Ile Ala Pro Cys Gln Lys Ala Met
1               5                   10                  15

<210> SEQ ID NO 96
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 96

Asp Leu Ile Arg Arg Thr Ile Ala Pro Cys Gln Lys Ala Met Gln
1               5                   10                  15

<210> SEQ ID NO 97
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 97

Leu Ile Arg Arg Thr Ile Ala Pro Cys Gln Lys Ala Met Gln Asp
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: Synthetic polypeptide
```

```
<400> SEQUENCE: 98

Ile Arg Arg Thr Ile Ala Pro Cys Gln Lys Ala Met Gln Asp Ala
1               5                   10                  15

<210> SEQ ID NO 99
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 99

Arg Arg Thr Ile Ala Pro Cys Gln Lys Ala Met Gln Asp Ala Glu
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 100

Arg Thr Ile Ala Pro Cys Gln Lys Ala Met Gln Asp Ala Glu Val
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 101

Thr Ile Ala Pro Cys Gln Lys Ala Met Gln Asp Ala Glu Val Ser
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 102

Ile Ala Pro Cys Gln Lys Ala Met Gln Asp Ala Glu Val Ser Lys
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 103

Ala Pro Cys Gln Lys Ala Met Gln Asp Ala Glu Val Ser Lys Ser
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 104
```

```
Pro Cys Gln Lys Ala Met Gln Asp Ala Glu Val Ser Lys Ser Asp
1               5                   10                  15
```

<210> SEQ ID NO 105
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 105

```
Cys Gln Lys Ala Met Gln Asp Ala Glu Val Ser Lys Ser Asp Ile
1               5                   10                  15
```

<210> SEQ ID NO 106
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 106

```
Gln Lys Ala Met Gln Asp Ala Glu Val Ser Lys Ser Asp Ile Gly
1               5                   10                  15
```

<210> SEQ ID NO 107
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 107

```
Lys Ala Met Gln Asp Ala Glu Val Ser Lys Ser Asp Ile Gly Glu
1               5                   10                  15
```

<210> SEQ ID NO 108
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 108

```
Ala Met Gln Asp Ala Glu Val Ser Lys Ser Asp Ile Gly Glu Val
1               5                   10                  15
```

<210> SEQ ID NO 109
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 109

```
Met Gln Asp Ala Glu Val Ser Lys Ser Asp Ile Gly Glu Val Ile
1               5                   10                  15
```

<210> SEQ ID NO 110
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 110

```
Gln Asp Ala Glu Val Ser Lys Ser Asp Ile Gly Glu Val Ile Leu
```

```
1               5                   10                  15

<210> SEQ ID NO 111
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 111

Asp Ala Glu Val Ser Lys Ser Asp Ile Gly Glu Val Ile Leu Val
1               5                   10                  15

<210> SEQ ID NO 112
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 112

Ala Glu Val Ser Lys Ser Asp Ile Gly Glu Val Ile Leu Val Gly
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 113

Glu Val Ser Lys Ser Asp Ile Gly Glu Val Ile Leu Val Gly Gly
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 114

Val Ser Lys Ser Asp Ile Gly Glu Val Ile Leu Val Gly Gly Met
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 115

Ser Lys Ser Asp Ile Gly Glu Val Ile Leu Val Gly Gly Met Thr
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 116

Lys Ser Asp Ile Gly Glu Val Ile Leu Val Gly Gly Met Thr Arg
1               5                   10                  15
```

```
<210> SEQ ID NO 117
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 117

Ser Asp Ile Gly Glu Val Ile Leu Val Gly Gly Met Thr Arg Met
1               5                   10                  15

<210> SEQ ID NO 118
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 118

Asp Ile Gly Glu Val Ile Leu Val Gly Gly Met Thr Arg Met Pro
1               5                   10                  15

<210> SEQ ID NO 119
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 119

Ile Gly Glu Val Ile Leu Val Gly Gly Met Thr Arg Met Pro Lys
1               5                   10                  15

<210> SEQ ID NO 120
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 120

Gly Glu Val Ile Leu Val Gly Gly Met Thr Arg Met Pro Lys Val
1               5                   10                  15

<210> SEQ ID NO 121
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 121

Glu Val Ile Leu Val Gly Gly Met Thr Arg Met Pro Lys Val Gln
1               5                   10                  15

<210> SEQ ID NO 122
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 122

Val Ile Leu Val Gly Gly Met Thr Arg Met Pro Lys Val Gln Gln
1               5                   10                  15

<210> SEQ ID NO 123
```

```
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 123

Ile Leu Val Gly Gly Met Thr Arg Met Pro Lys Val Gln Gln Thr
1               5                   10                  15

<210> SEQ ID NO 124
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 124

Leu Val Gly Gly Met Thr Arg Met Pro Lys Val Gln Gln Thr Val
1               5                   10                  15

<210> SEQ ID NO 125
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 125

Val Gly Gly Met Thr Arg Met Pro Lys Val Gln Gln Thr Val Gln
1               5                   10                  15

<210> SEQ ID NO 126
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 126

Gly Gly Met Thr Arg Met Pro Lys Val Gln Gln Thr Val Gln Asp
1               5                   10                  15

<210> SEQ ID NO 127
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 127

Gly Met Thr Arg Met Pro Lys Val Gln Gln Thr Val Gln Asp Leu
1               5                   10                  15

<210> SEQ ID NO 128
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 128

Met Thr Arg Met Pro Lys Val Gln Gln Thr Val Gln Asp Leu Phe
1               5                   10                  15

<210> SEQ ID NO 129
<211> LENGTH: 15
<212> TYPE: PRT
```

<213> ORGANISM: Artificial Sequence
<220> FEATURE:
<223> OTHER INFORMATION: Synthetic polypeptide

<400> SEQUENCE: 129

Thr Arg Met Pro Lys Val Gln Gln Thr Val Gln Asp Leu Phe Gly
1               5                   10                  15

<210> SEQ ID NO 130
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 130

Arg Met Pro Lys Val Gln Gln Thr Val Gln Asp Leu Phe Gly Arg
1               5                   10                  15

<210> SEQ ID NO 131
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 131

Met Pro Lys Val Gln Gln Thr Val Gln Asp Leu Phe Gly Arg Ala
1               5                   10                  15

<210> SEQ ID NO 132
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 132

Pro Lys Val Gln Gln Thr Val Gln Asp Leu Phe Gly Arg Ala Pro
1               5                   10                  15

<210> SEQ ID NO 133
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 133

Lys Val Gln Gln Thr Val Gln Asp Leu Phe Gly Arg Ala Pro Ser
1               5                   10                  15

<210> SEQ ID NO 134
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 134

Val Gln Gln Thr Val Gln Asp Leu Phe Gly Arg Ala Pro Ser Lys
1               5                   10                  15

<210> SEQ ID NO 135
<211> LENGTH: 15
<212> TYPE: PRT
<213> ORGANISM: Artificial Sequence
<220> FEATURE:

<223> OTHER INFORMATION: Synthetic polypeptide

<400> SEQUENCE: 135

Gln Gln Thr Val Gln Asp Leu Phe Gly Arg Ala Pro Ser Lys Ala
1               5                   10                  15

<210> SEQ ID NO 136
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 136

Gln Thr Val Gln Asp Leu Phe Gly Arg Ala Pro Ser Lys Ala Val
1               5                   10                  15

<210> SEQ ID NO 137
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 137

Thr Val Gln Asp Leu Phe Gly Arg Ala Pro Ser Lys Ala Val Asn
1               5                   10                  15

<210> SEQ ID NO 138
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 138

Val Gln Asp Leu Phe Gly Arg Ala Pro Ser Lys Ala Val Asn Pro
1               5                   10                  15

<210> SEQ ID NO 139
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 139

Gln Asp Leu Phe Gly Arg Ala Pro Ser Lys Ala Val Asn Pro Asp
1               5                   10                  15

<210> SEQ ID NO 140
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 140

Asp Leu Phe Gly Arg Ala Pro Ser Lys Ala Val Asn Pro Asp Glu
1               5                   10                  15

<210> SEQ ID NO 141
<211> LENGTH: 15
<212> TYPE: PRT
<213> ORGANISM: Artificial Sequence
<220> FEATURE:
<223> OTHER INFORMATION: Synthetic polypeptide

```
<400> SEQUENCE: 141

Leu Phe Gly Arg Ala Pro Ser Lys Ala Val Asn Pro Asp Glu Ala
1               5                   10                  15

<210> SEQ ID NO 142
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 142

Phe Gly Arg Ala Pro Ser Lys Ala Val Asn Pro Asp Glu Ala Val
1               5                   10                  15

<210> SEQ ID NO 143
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 143

Gly Arg Ala Pro Ser Lys Ala Val Asn Pro Asp Glu Ala Val Ala
1               5                   10                  15

<210> SEQ ID NO 144
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 144

Arg Ala Pro Ser Lys Ala Val Asn Pro Asp Glu Ala Val Ala Ile
1               5                   10                  15

<210> SEQ ID NO 145
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 145

Ala Pro Ser Lys Ala Val Asn Pro Asp Glu Ala Val Ala Ile Gly
1               5                   10                  15

<210> SEQ ID NO 146
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 146

Pro Ser Lys Ala Val Asn Pro Asp Glu Ala Val Ala Ile Gly Ala
1               5                   10                  15

<210> SEQ ID NO 147
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 147
```

-continued

```
Ser Lys Ala Val Asn Pro Asp Glu Ala Val Ala Ile Gly Ala Ala
1               5                   10                  15

<210> SEQ ID NO 148
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 148

Lys Ala Val Asn Pro Asp Glu Ala Val Ala Ile Gly Ala Ala Ile
1               5                   10                  15

<210> SEQ ID NO 149
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 149

Ala Val Asn Pro Asp Glu Ala Val Ala Ile Gly Ala Ala Ile Gln
1               5                   10                  15

<210> SEQ ID NO 150
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 150

Val Asn Pro Asp Glu Ala Val Ala Ile Gly Ala Ala Ile Gln Gly
1               5                   10                  15

<210> SEQ ID NO 151
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 151

Asn Pro Asp Glu Ala Val Ala Ile Gly Ala Ala Ile Gln Gly Gly
1               5                   10                  15

<210> SEQ ID NO 152
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 152

Pro Asp Glu Ala Val Ala Ile Gly Ala Ala Ile Gln Gly Gly Val
1               5                   10                  15

<210> SEQ ID NO 153
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 153

Asp Glu Ala Val Ala Ile Gly Ala Ala Ile Gln Gly Gly Val Leu
1               5                   10                  15
```

-continued

```
<210> SEQ ID NO 154
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 154

Glu Ala Val Ala Ile Gly Ala Ala Ile Gln Gly Gly Val Leu Ala
1               5                   10                  15

<210> SEQ ID NO 155
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 155

Ala Val Ala Ile Gly Ala Ala Ile Gln Gly Gly Val Leu Ala Gly
1               5                   10                  15

<210> SEQ ID NO 156
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 156

Val Ala Ile Gly Ala Ala Ile Gln Gly Gly Val Leu Ala Gly Asp
1               5                   10                  15

<210> SEQ ID NO 157
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 157

Ala Ile Gly Ala Ala Ile Gln Gly Gly Val Leu Ala Gly Asp Val
1               5                   10                  15

<210> SEQ ID NO 158
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 158

Ile Gly Ala Ala Ile Gln Gly Gly Val Leu Ala Gly Asp Val Thr
1               5                   10                  15

<210> SEQ ID NO 159
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 159

Gly Ala Ala Ile Gln Gly Gly Val Leu Ala Gly Asp Val Thr Asp
1               5                   10                  15
```

```
<210> SEQ ID NO 160
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 160

Ala Ala Ile Gln Gly Gly Val Leu Ala Gly Asp Val Thr Asp Val
1               5                   10                  15

<210> SEQ ID NO 161
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 161

Ala Ile Gln Gly Gly Val Leu Ala Gly Asp Val Thr Asp Val Leu
1               5                   10                  15

<210> SEQ ID NO 162
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 162

Ile Gln Gly Gly Val Leu Ala Gly Asp Val Thr Asp Val Leu Leu
1               5                   10                  15

<210> SEQ ID NO 163
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 163

Gln Gly Gly Val Leu Ala Gly Asp Val Thr Asp Val Leu Leu Leu
1               5                   10                  15

<210> SEQ ID NO 164
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 164

Gly Gly Val Leu Ala Gly Asp Val Thr Asp Val Leu Leu Leu Asp
1               5                   10                  15

<210> SEQ ID NO 165
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 165

Gly Val Leu Ala Gly Asp Val Thr Asp Val Leu Leu Leu Asp Val
1               5                   10                  15

<210> SEQ ID NO 166
<211> LENGTH: 15
```

```
<212> TYPE: PRT
<213> ORGANISM: Artificial Sequence
<220> FEATURE:
<223> OTHER INFORMATION: Synthetic polypeptide

<400> SEQUENCE: 166

Val Leu Ala Gly Asp Val Thr Asp Val Leu Leu Leu Asp Val Thr
1               5                   10                  15

<210> SEQ ID NO 167
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 167

Leu Ala Gly Asp Val Thr Asp Val Leu Leu Leu Asp Val Thr Pro
1               5                   10                  15

<210> SEQ ID NO 168
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 168

Ala Gly Asp Val Thr Asp Val Leu Leu Leu Asp Val Thr Pro Leu
1               5                   10                  15

<210> SEQ ID NO 169
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 169

Gly Asp Val Thr Asp Val Leu Leu Leu Asp Val Thr Pro Leu Ser
1               5                   10                  15

<210> SEQ ID NO 170
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 170

Asp Val Thr Asp Val Leu Leu Leu Asp Val Thr Pro Leu Ser Leu
1               5                   10                  15

<210> SEQ ID NO 171
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 171

Val Thr Asp Val Leu Leu Leu Asp Val Thr Pro Leu Ser Leu Gly
1               5                   10                  15

<210> SEQ ID NO 172
<211> LENGTH: 15
<212> TYPE: PRT
<213> ORGANISM: Artificial Sequence
```

```
<220> FEATURE:
<223> OTHER INFORMATION: Synthetic polypeptide

<400> SEQUENCE: 172

Thr Asp Val Leu Leu Leu Asp Val Thr Pro Leu Ser Leu Gly Ile
1               5                   10                  15

<210> SEQ ID NO 173
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 173

Asp Val Leu Leu Leu Asp Val Thr Pro Leu Ser Leu Gly Ile Glu
1               5                   10                  15

<210> SEQ ID NO 174
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 174

Val Leu Leu Leu Asp Val Thr Pro Leu Ser Leu Gly Ile Glu Thr
1               5                   10                  15

<210> SEQ ID NO 175
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 175

Leu Leu Leu Asp Val Thr Pro Leu Ser Leu Gly Ile Glu Thr Leu
1               5                   10                  15

<210> SEQ ID NO 176
<211> LENGTH: 23
<212> TYPE: DNA
<213> ORGANISM: Artificial Sequence
<220> FEATURE:
<223> OTHER INFORMATION: Synthetic polynucleotide primer

<400> SEQUENCE: 176
gctcactgga tggtgggaag atg                                              23
```

US 8,591,893 B2

PARATOPE AND EPITOPE OF ANTI-MORTALIN ANTIBODY

TECHNICAL FIELD

The present invention relates to variable regions from an anti-mortalin antibody having a cellular internalizing function and a carrier for cellular internalization based on a single-chain antibody that contains the variable regions.

The present invention also relates to an epitope in the amino acid sequence of mortalin, which recognizes an anti-mortalin antibody as having or not having the cellular internalizing function.

BACKGROUND ART

Mortalin (mortalin 2) is a protein of 679 amino acids and having a molecular weight of 73,913 daltons. Its proprotein has a mitochondrial transfer signal peptide of 46 amino acids. Mortalin is a member of the Hsp70 family proteins, and it is a non-thermoresponsive protein. Mortalin has very high homology with *Escherichia coli* DnaK, yeast SSC1p, and Hsp70 family proteins such as Hsp70, which is constantly expressed in rat cytoplasmic fractions, Hsc70, and BiP, which is an isoform existing in rat endoplasmic reticula. Regarding mortalin, first, a mortalin 1 (mot-1) gene has been isolated from cytoplasmic fractions of normal mouse-derived fibroblasts (Wadhwa, R., Kaul, S. C., Ikawa, Y., and Sugimoto, Y. (1993) J Biol Chem 268, 6615-6621). Next, through immunological cloning of the cDNA of mouse immortalized cells and comparison with a sequence isolated from normal cells, the presence of a mortalin 2 gene (mot-2) encoding a protein differing by only 2 amino acid residues at the carboxyl terminus has been revealed (Wadhwa, R., Kaul, S. C., Sugimoto, Y., and Mitsui, Y. (1993) J BiolChem 268, 22239-22242). Mortalin 1 (mot-1) is present in normal cells, but mortalin 2 (mot-2) is present in immortalized cells. As revealed by nude mouse assay, whereas the expression of mortalin 1 (mot-1) causes a cellular-senescence-like phenotype, the overexpression of mortalin 2 (mot-2) causes malignant mutation. These indicates that mot-1 and mot2 exert biological activities that contrast one another (Wadhwa, R., Shyichi, T., Robert, M., Yoshida, A., Reddel, R. R., Nomura, H., Mitsui, Y., and Kaul, S. C. (1998) J Biol Chem 273, 29586-29591). Human mortalin has homology as high as 95% with mouse mortalin at the protein level and is also referred to as human mortalin 2 (hmot-2) because of the presence of only one type that exerts functions and properties similar to those of mortalin 2 (Kaul, S. C., Duncan, E. L., Englezou, A., Takano, S., Reddel, R. R., Mitsui, Y., and Wadhwa, R. (1998) Oncogene 17, 907-911). In the present invention, unless particularly specified, mouse mortalin 2 and human mortalin 2 are both simply referred to as mortalin or mortalin 2.

It has been suggested that mortalin 2 binds to various molecules at various positions within cells via calcium-dependent self-phosphorylation and then is involved in wide-ranging functions including mitochondrial transport, intracellular transport, chaperonin functions, stress responses, tumorigenesis, and the like. In particular, it has been revealed that: mortalin 2 binds to p53, a tumor suppressor protein, so as to inactivate the transcriptional activity functions of p53 (Wadhwa, R., Shyichi, T., Robert, M., Yoshida, A., Reddel, R. R., Nomura, H., Mitsui, Y., and Kaul, S. C. (1998) J Biol Chem 273, 29586-29591); and mortalin 2 cooperates with telomerase to immortalize human foreskin fibroblasts (Kaul, S. C., Yaguchi, T., Taira, K., Reddel, R. R., and Wadhwa, R. (2002) ECR submitted), for example. Hence, essential involvement of mortalin 2 in oncogenesis has been revealed (Kaul, S. C., Taira, K., Pereira-Smith, O. M., and Wadhwa, R. (2002) Exp Gerontol 37, 1157-1164; Wadhwa, R., Takano, S., Kaur, K., Deocaris, C. C., Pereira-Smith, O. M., Reddel, R. R., and Kaul, S. C. (2006) Int J Cancer 118, 2973-2980; Deocaris, C. C., Kaul, S. C., and Wadhwa, R. (2006) Cell Stress Chaperones 11, 116-128; Dundas, S. R., Lawrie, L. C., Rooney, P. H., and Murray, G. I. (2005) J Pathol 205, 74-81; Shin, B. K., Wang, H., Yim, A. M., Le Naour, F., Brichory, F., Jang, J. H., Zhao, R., Purays, E., Tra, J., Michael, C. W., Misek, D. E., and Hanash, S. M. (2003) J Biol Chem 278, 7607-7616; Pizzatti, L., Sa, L. A., de Souza, J. M., Bisch, P. M., and Abdelhay, E. (2006) Biochim Biophys Acta 1764, 929-942; Walker, C., Bottger, S., and Low, B. (2006) Am J Pathol 168, 1526-1530; and International Patent Publication WO2006/022344 A1 and JP Patent Publication (Kokai) No. 2006-89471 A. It has also been shown that the possibility exists for a molecule such as an anti-mortalin antibody to bind to mortalin, so as to suppress the effects and functions of mortalin, can be used as an anticancer agent (Walker, C., Bottger, S., and Low, B. (2006) Am J Pathol 168, 1526-1530; Wadhwa, R., Sugihara, T., Yoshida, A., Nomura, H., Reddel, R. R., Simpson, R., Maruta, H., and Kaul, S. C. (2000) Cancer Res 60, 6818-6821; Wadhwa, R., Ando, H., Kawasaki, H., Taira, K., and Kaul, S. C. (2003) EMBO Rep 4, 595-601; Deocaris, C. C., Widodo, N., Shrestha, B. G, Kaur, K., Ohtaka, M., Yamasaki, K., Kaul, S. C., and Wadhwa, R. (2007) Cancer Lett (in press)).

The present inventors have previously examined whether mortalin can be an effective target for cancer treatment, in addition to examination of the relationship between an increased expression level of mortalin and oncogenesis. Thus, they have applied for a patent relating to an anti-mortalin antibody having a internalizing function into cancer cells, a pharmaceutical composition for cancer treatment using the antibody, a drug carrier, and the like (International Patent Publication WO2006/022344 A1, JP Patent Publication (Kokai) No. 2006-89471 A). Such anti-mortalin antibody having the internalizing function into cancer cells can be used itself not only as an antibody drug, but also as a drug carrier that delivers immunotoxins or the like to tumor cells.

In the course of examining them, the present inventors have observed that not all antibodies specifically recognizing mortalin have such internalizing function into cancer cells. Thy have also observed the presence of antibodies capable of specifically recognizing mortalin, but incapable of being internalized into cancer cells. However, essential differences in terms of amino acid sequences or structures between antibodies having a internalizing function into cancer cells and antibodies not having such function have not been elucidated. Hence, the kind of region in the full-length antibody that is involved in the internalization mechanism has remained completely unknown.

Drugs preferred herein are humanized antibodies with low immunogenicity that causes low adverse reaction in normal cells or drugs characterized in that only a region that is as short as possible can be administered. Accordingly, in addition to elucidation of the internalization mechanism of a mortalin antibody, elucidation of a region involved in internalization has been desired.

Also, as a first step for internalization of an anti-mortalin antibody within cancer cells, first, interaction of the antibody with mortalin is thought to be essential. Hence, elucidation of a site on mortalin involved in the interaction with an anti-mortalin antibody, and particularly, elucidation of recognition regions recognized by antibodies having the internalizing function and antibodies not having such function, have also been desired.

Furthermore, if an epitope sequence to be recognized by an antibody having the internalizing function can be determined, the epitope is expressed on cancer cell surfaces using the nucleic acid molecule encoding the epitope, so that internalization of the anti-mortalin antibody can be accelerated. Therefore, in particular, the sequencing of an epitope of an antibody having the internalizing function has been strongly desired.

All descriptions of these cited documents are incorporated into the specification of the present application.

DISCLOSURE OF THE INVENTION

Problem to Be Solved by the Invention

An object of the present invention is to: determine the nucleotide sequence of DNA encoding each variable region of an anti-mortalin antibody having the internalizing function and an anti-mortalin antibody not having such function; determine, through comparison of their amino acid sequences, a region of the anti-mortalin antibody that is involved in the internalizing function into tumor cells and the amino acid sequence thereof; and provide a carrier containing the region for drug delivery into tumor cells.

Another object of the present invention is to determine a region on mortalin interacting with the region of an anti-mortalin antibody involved in the internalizing function into cancer cells and the amino acid sequence thereof.

Still another object of the present invention is to determine the sequence of an epitope to be recognized by an anti-mortalin antibody having the internalizing function and to accelerate the internalization of the anti-mortalin antibody and a drug containing the anti-mortalin antibody as a carrier through expression of the epitope on cancer cell surfaces using the nucleic acid molecule encoding the epitope.

Means to Solve the Problems

The present inventors have determined each amino acid sequence of L chains and H chains of 6 types of monoclonal antibodies binding to mortalin and then compared the amino acid sequences of those having the internalizing function (internalization function) with the same of those not having such function. The present inventors have discovered significant sequential differences in the variable regions.

Whereas 4 out of 5 types of antibodies having the internalizing function into cells have variable regions that have sequences significantly analogous to each other, the antibodies have low similarity with antibodies not having the function. In particular, their CDR sequences significantly differ from each other. A single-chain antibody (single chain Fv, scFv) is prepared with the use of cDNA of the monoclonal antibody, wherein L chain and H chain variable regions are linked via a peptide linker, and then its binding activity as a paratope for mortalin was confirmed.

Also, as a result of examining the position of an epitope of mortalin to be recognized by an antibody paratope using each partially deleted antibody, the present inventors have also confirmed that the two recognize different amino acid sequences of epitopes.

These results suggest a high possibility that whether or not an anti-mortalin antibody has capability of being internalized intracellularly would depend on its unique CDR sequence and at least on the sequences of both L-chain and H-chain variable regions. Specifically, the results strongly suggest the possibility that a chimeric antibody prepared using both L-chain and H-chain variable regions from an anti-mortalin antibody having the capability of being internalized intracellularly, or a single-chain antibody, and also a humanized antibody prepared using the CDR sequence would be sufficiently internalized into cancer cells in a cancer-cell-specific manner, so as to suppress mortalin functions. In contrast, the results suggest the high possibility that a chimeric antibody prepared using a variable region from an anti-mortalin antibody not having the capability of being internalized intracellularly, a single-chain antibody, and a humanized antibody prepared using the CDR sequence would remain on cancer cell surfaces, so as to bind to mortalin on the cancer cell surfaces.

The former type of antibodies can be drugs or drug carriers that are internalized into cancer cells, so as to inhibit mortalin activity. The latter type of antibodies can be used as a drug having a neutralizing activity for mortalin, which can inhibit the internalization of mortalin into cells. Specifically, the present invention provides an anticancer pharmaceutical composition containing as active ingredients the variable regions alone of an anti-mortalin monoclonal antibody, or a single-chain antibody prepared using the variable regions. The present invention also provides a drug carrier for cancer cells containing the same variable regions or a single-chain antibody containing the same as a carrier or provides a carrier for detection of the live image of cancer cells.

The present inventors have conceived of using an anti-mortalin antibody having the cellular internalizing function as a nucleic acid carrier for gene therapy for cancer with the use of the antibody's property of being internalized specifically into cancer cells. Specifically, the present inventors have confirmed that a molecular conjugate prepared by linking cationic polymers to an H chain and an L chain of the antibody and then mixing the resultant with a gene-containing plasmid is specifically incorporated into cancer cells, following which the gene is expressed within the cancer cells. The present inventors filed a patent application regarding the aforementioned points having the same priority date as the present application (JP Patent Application No. 2007-141073, which is now pending as JP Patent Application No. 2007-243934; the descriptions thereof are incorporated herein).

Furthermore, in the present invention, a region having an epitope sequence to be recognized by an anti-mortalin antibody having the internalizing function could be successfully determined in view of these findings. The region was narrowed down to 30 amino acid residues, an epitope mapping method was applied, and then the amino acid sequence of an epitope that is specifically recognized only by an anti-mortalin antibody having the internalizing function was determined. Through the use of a peptide containing the epitope as an immunogen, an anti-mortalin peptide antibody with a further enhanced internalizing function can be prepared, the antibody can be directly used as an anticancer agent, and the antibody can also be used for the delivery of anticancer agents (low-molecular-weight compounds, toxins, or nucleic acid molecules) and labeling compounds (fluorescent substances or metal particles such as quantum dots) into cancer cells.

Furthermore, a mortalin epitope can be expressed on cancer cell surfaces using a nucleic acid encoding a polypeptide containing the epitope sequence. Such mortalin epitope on cancer cell surfaces can accelerate the internalization of an anti-mortalin antibody and a drug containing an anti-mortalin antibody as a carrier. Hence, an expression vector containing a nucleic acid that encodes a polypeptide containing the epitope sequence can be used as an agent for accelerating the internalization of an anti-mortalin antibody and a drug bound thereto into cancer cells.

Specifically, the present invention is as described below.

[1] An L-chain variable region of a recombinant anti-mortalin antibody, which specifically recognizes mortalin 2 and has a cellular internalizing function, wherein CDR1 consists of the sequence "KSSQSLLDSDGKTYLN (SEQ ID NO: 1)," CDR2 consists of the sequence "LVSKLDS (SEQ ID NO: 2)," and CDR3 consists of the sequence "WQGTHF-PRT (SEQ ID NO: 3)."

[2] The L-chain variable region of the recombinant anti-mortalin antibody according to [1] above, which consists of the following amino acid sequence (a) or (b):
(a) the amino acid sequence shown in SEQ ID NO: 4 or 5; and
(b) an amino acid sequence derived from the amino acid sequence shown in SEQ ID NO: 4 or 5 by deletion, substitution, and/or addition of one or several amino acids in a signal sequence and/or a framework sequence.

[3] An L-chain variable region of a recombinant anti-mortalin antibody, which specifically recognizes mortalin 2 and has a cellular internalizing function, wherein CDR1 consists of the sequence "RASQEISGYLS (SEQ ID NO: 6)," CDR2 consists of the sequence "AASTLDS (SEQ ID NO: 7)," and CDR3 consists of the sequence "LQYASYPPT (SEQ ID NO: 8)."

[4] The L-chain variable region of the recombinant anti-mortalin antibody according to [3] above, which consists of the following amino acid sequence (a) or (b):
(a) the amino acid sequence shown in SEQ ID NO: 9; or
(b) an amino acid sequence derived from the amino acid sequence shown in SEQ ID NO: 9 by deletion, substitution, and/or addition of one or several amino acids in a signal sequence and/or a framework sequence.

[5] An L-chain variable region of a recombinant anti-mortalin antibody, which specifically recognizes mortalin 2, but does not have a cellular internalizing function, wherein CDR1 consists of the sequence "RSSKSLLYSNGITYLY (SEQ ID NO: 10)," CDR2 consists of the sequence "QMSNLAS (SEQ ID NO: 11)," and CDR3 consists of the sequence "AQNLELPWT (SEQ ID NO: 12)."

[6] The L-chain variable region of the recombinant anti-mortalin antibody according to [5] above, which consists of the following amino acid sequence (a) or (b):
(a) the amino acid sequence shown in SEQ ID NO: 13; or
(b) an amino acid sequence derived from the amino acid sequence shown in SEQ ID NO: 13 by deletion, substitution, and/or addition of one or several amino acids in a signal sequence and/or a framework sequence.

[7] An H-chain variable region of a recombinant anti-mortalin antibody, which specifically recognizes mortalin 2 and has a cellular internalizing function, wherein CDR1 consists of the sequence "SYWMH (SEQ ID NO: 14)," CDR2 consists of the sequence "EIDPSDSYTKYNQKFKG (SEQ ID NO: 15)" or "EIDPSDSYTDYNQNFKG (SEQ ID NO: 18)," and CDR3 consists of the sequence "GDY (SEQ ID NO: 16)."

[8] The H-chain variable region of the recombinant anti-mortalin antibody according to [7] above, which consists of the following amino acid sequence (a) or (b):
(a) the amino acid sequence shown in SEQ ID NO: 17, 19, or 20; or
(b) an amino acid sequence derived from the amino acid sequence shown in SEQ ID NO: 17, 19, or 20 by deletion, substitution, and/or addition of one or several amino acids in a signal sequence and/or a framework sequence.

[9] An H-chain variable region of a recombinant anti-mortalin antibody, which specifically recognizes mortalin 2 and has a cellular internalizing function, wherein CDR1 consists of the sequence "TNAMN (SEQ ID NO: 21)," CDR2 consists of the sequence "RIRSKSNNYATYYADSVKD (SEQ ID NO: 22)," and CDR3 consists of the sequence "DGYYSY (SEQ ID NO: 23)."

[10] The H-chain variable region of the recombinant anti-mortalin antibody according to [9] above, which consists of the following amino acid sequence (a) or (b):
(a) the amino acid sequence shown in SEQ ID NO: 24; or
(b) an amino acid sequence derived from the amino acid sequence shown in SEQ ID NO: 24 by deletion, substitution, and/or addition of one or several amino acids in a signal sequence and/or a framework sequence.

[11] An H-chain variable region of a recombinant anti-mortalin antibody, which specifically recognizes mortalin 2, and does not have a cellular internalizing function, wherein CDR1 consists of the sequence "SYWMH (SEQ ID NO: 25)," CDR2 consists of the sequence "EINPSNGRTNYNEKFKS (SEQ ID NO: 26)," and CDR3 consists of the sequence "SRYYGSCYFDY (SEQ ID NO: 27)."

[12] The H-chain variable region of the recombinant anti-mortalin antibody according to [11] above, which consists of the following amino acid sequence (a) or (b):
(a) the amino acid sequence shown in SEQ ID NO: 28; or
(b) an amino acid sequence derived from the amino acid sequence shown in SEQ ID NO: 28 by deletion, substitution, and/or addition of one or several amino acids in a signal sequence and/or a framework sequence.

[13] An anti-mortalin single-chain antibody specifically recognizing mortalin 2, which comprises an L-chain variable region of an anti-mortalin antibody and an H-chain variable region of an anti-mortalin antibody,
wherein the L-chain variable region consists of any one of the following amino acid sequences (a) to (d):
(a) the amino acid sequence shown in SEQ ID NO: 4 or 5,
(b) an amino acid sequence derived from the amino acid sequence shown in SEQ ID NO: 4 or 5 by deletion, substitution, and/or addition of one or several amino acids in a signal sequence and/or a framework sequence,
(c) the amino acid sequence shown in SEQ ID NO: 9, and
(d) an amino acid sequence derived from the amino acid sequence shown in SEQ ID NO: 9 by deletion, substitution, and/or addition of one or several amino acids in a signal sequence and/or a framework sequence;
wherein the H-chain variable region consists of any one of the following amino acid sequences (e) to (h):
(e) the amino acid sequence shown in SEQ ID NO: 17, 19, or 20,
(f) an amino acid sequence derived from the amino acid sequence shown in SEQ ID NO: 17, 19, or 20 by deletion, substitution, and/or addition of one or several amino acids in a signal sequence and/or a framework sequence,
(g) the amino acid sequence shown in SEQ ID NO: 24, and
(h) an amino acid sequence derived from the amino acid sequence shown in SEQ ID NO: 24 by deletion, substitution, and/or addition of one or several amino acids in a signal sequence and/or a framework sequence.

[14] An anti-mortalin single-chain antibody specifically recognizing mortalin 2, which comprises an L-chain variable region of an anti-mortalin antibody and an H-chain variable region of an anti-mortalin antibody, wherein the L-chain variable region consists of the following amino acid sequence (a) or (b):
(a) the amino acid sequence shown in SEQ ID NO: 13, or
(b) an amino acid sequence derived from the amino acid sequence shown in SEQ ID NO: 13 by deletion, substitution, and/or addition of one or several amino acids in a signal sequence and/or a framework sequence;
wherein the H-chain variable region consists of the following amino acid sequence (c) or (d):
(c) the amino acid sequence shown in SEQ ID NO: 28, or
(d) an amino acid sequence derived from the amino acid sequence shown in SEQ ID NO: 28 by deletion, substitution, and/or addition of one or several amino acids in a signal sequence and/or a framework sequence.

[15] A DNA which encodes an L-chain variable region of an anti-mortalin antibody specifically recognizing mortalin 2 and having a cellular internalizing function, wherein the DNA is any one of the following DNAs (a) to (d):
(a) a DNA encoding the amino acid sequence shown in SEQ ID NO: 4, 5, or 9;
(b) a DNA encoding an amino acid sequence derived from the amino acid sequence shown in SEQ ID NO: 4, 5, or 9 by deletion, substitution, and/or addition of one or several amino acids in a signal sequence and/or a framework sequence;
(c) a DNA consisting of the nucleotide sequence shown in SEQ ID NO: 42, 43, 44, 45, or 46; and
(d) a DNA hybridizing under stringent conditions to the nucleotide sequence shown in SEQ ID NO: 42, 43, 44, 45, or 46.

[16] A DNA which encodes an H-chain variable region of an anti-mortalin antibody specifically recognizing mortalin 2 and having a cellular internalizing function, wherein the DNA is any one of the following DNAs (a) to (d):
(a) a DNA encoding the amino acid sequence shown in SEQ ID NO: 17, 18, or 20;
(b) a DNA encoding an amino acid sequence derived from the amino acid sequence shown in SEQ ID NO: 17, 18, or 20 by deletion, substitution, and/or addition of one or several amino acids in a signal sequence and/or a framework sequence;
(c) a DNA consisting of the nucleotide sequence shown in SEQ ID NO: 48, 49, 50, 51, or 52; and
(d) a DNA hybridizing under stringent conditions to the nucleotide sequence shown in SEQ ID NO: 48, 49, 50, 51, or 52.

[17] A DNA which encodes an L-chain variable region of an anti-mortalin antibody specifically recognizing mortalin 2, but not having a cellular internalizing function, wherein the DNA is any one of the following DNAs (a) to (d):
(a) a DNA encoding the amino acid sequence shown in SEQ ID NO: 13;
(b) a DNA encoding an amino acid sequence derived from the amino acid sequence shown in SEQ ID NO: 13 by deletion, substitution, and/or addition of one or several amino acids in a signal sequence and/or a framework sequence;
(c) a DNA consisting of the nucleotide sequence shown in SEQ ID NO: 47; and
(d) a DNA hybridizing under stringent conditions to the nucleotide sequence shown in SEQ ID NO: 47.

[18] A DNA which encodes an H-chain variable region of an anti-mortalin antibody specifically recognizing mortalin 2, but not having a cellular internalizing function, wherein the DNA is any one of the following DNAs (a) to (d):
(a) a DNA encoding the amino acid sequence shown in SEQ ID NO: 28;
(b) a DNA encoding an amino acid sequence derived from the amino acid sequence shown in SEQ ID NO: 28 by deletion, substitution, and/or addition of one or several amino acids in a signal sequence and/or a framework sequence;
(c) a DNA consisting of the nucleotide sequence shown in SEQ ID NO: 53; and
(d) a DNA hybridizing under stringent conditions to the nucleotide sequence shown in SEQ ID NO: 53.

[19] A DNA encoding an anti-mortalin single-chain antibody that specifically recognizes mortalin 2, which comprises the DNA according to [15] above that encodes the L-chain variable region of the anti-mortalin antibody specifically recognizing mortalin 2 and having a cellular internalizing function; and the DNA according to [16] above that encodes the H-chain variable region of the anti-mortalin antibody specifically recognizing mortalin 2 and having a cellular internalizing function.

[20] An expression vector, which comprises the DNA encoding the single-chain antibody according to [19] above.

[21] The expression vector according to [20] above, wherein the vector is a pET-27b(+) plasmid vector or a plasmid vector containing a PelB sequence incorporated therein.

[22] A DNA encoding an anti-mortalin single-chain antibody that specifically recognizes mortalin 2, which comprises the DNA according to [17] above that encodes the L-chain variable region of the anti-mortalin antibody specifically recognizing mortalin 2, but not having a cellular internalizing function; and the DNA according to [18] above that encodes the H-chain variable region of the anti-mortalin antibody specifically recognizing mortalin 2, but not having a cellular internalizing function.

[23] An expression vector, which comprises the DNA encoding the single-chain antibody according to [22] above.

[24] The expression vector according to [23] above, wherein the vector is a pET-27b(+) plasmid vector or a plasmid vector containing a PelB sequence incorporated therein.

[25] An anticancer agent which suppresses mortalin activity within a cancer cell, comprising, as an active ingredient, the anti-mortalin single-chain antibody according to [13] above or a conjugate of said single-chain antibody with a therapeutic compound bound thereto.

[26] An anticancer agent which suppresses mortalin activity on a cancer cell surface, comprising, as an active ingredient, the anti-mortalin single-chain antibody according to [14] above or a conjugate of said single-chain antibody with a therapeutic compound bound thereto.

[27] An anticancer agent which suppresses mortalin activity within a cancer cell, comprising, as an active ingredient, the DNA encoding the anti-mortalin single-chain antibody according to [19] above or a conjugate of said DNA with a therapeutic DNA bound thereto.

[28] An anticancer agent which suppresses mortalin activity on a cancer cell surface, comprising, as an active ingredient, the DNA encoding the anti-mortalin single-chain antibody according to [22] above or a conjugate of said DNA with a therapeutic DNA bound thereto.

[29] A reagent for detection or identification of a cancer cell, comprising the anti-mortalin single-chain antibody according to [13] or [14] above bound to a fluorescent labeling compound.

[30] A reagent for detection or identification of a cancer cell, comprising the DNA encoding the anti-mortalin single-chain antibody according to [19] or [22] above coupled to a reporter gene.

[31] A polypeptide which contains an amino acid sequence that specifically recognizes an anti-mortalin antibody having a cellular internalizing function, wherein the polypeptide comprises a sequence of at least 8 continuous amino acids selected from the group of partial sequences of the amino acid sequence ranging from amino acid position 310 to position 410 of mortalin 2.

[32] The polypeptide according to [31] above, wherein the amino acid sequence ranging from amino acid position 310 to position 410 of mortalin 2 is the amino acid sequence shown in SEQ ID NO: 55 or 62.

[33] The polypeptide according to [31] or [32] above, which comprises a sequence of at least 8 continuous amino acids selected from the group of partial sequences of the amino acid sequence ranging from amino acid position 381 to position 410 of mortalin 2.

[34] The polypeptide according to [33] above, wherein the amino acid sequence ranging from amino acid position 381 to position 410 of mortalin 2 is the amino acid sequence shown in SEQ ID NO: 56.

[35] The polypeptide according to [33] above, which is a partial sequence of the amino acid sequence ranging from amino acid position 381 to position 410 of mortalin 2, and comprises the amino acid sequence "LFGRAP" shown in SEQ ID NO: 66.

[36] The polypeptide according to [35] above, wherein the partial sequence of the amino acid sequence ranging from amino acid position 381 to position 410 of mortalin 2 is selected from among amino acid sequences "PKVQQTVQDLFGRAP (SEQ ID NO: 67)," "KVQQTVQDLFGRAPS (SEQ ID NO 68)," "VQQTVQDLFGRAPSK (SEQ ID NO: 69)," "QQTVQDLFGRAPSKA (SEQ ID NO: 70)," "QTVQDLFGRAPSKAV (SEQ ID NO: 71)," "TVQDLFGRAPSKAVN (SEQ ID NO 72)," "VQDLFGRAPSKAVNP (SEQ ID NO: 73)," "QDLFGRAPSKAVNPD (SEQ ID NO: 74)," "DLFGRAPSKAVNPDE (SEQ ID NO: 75)," and "LFGRAPSKAVNPDEA (SEQ ID NO: 76)."

[37] The polypeptide according to [34] above, wherein the partial sequence of the amino acid sequence ranging from amino acid position 381 to position 410 of mortalin 2 is selected from among amino acid sequences "KAMQDAEVSKSDIGE (SEQ ID NO: 77)," "GEVILVGGMTRMPKV (SEQ ID NO 78)," "EVILVGGMTRMPKVQ (SEQ ID NO: 79)," "GMTRMPKVQQTVQDL (SEQ ID NO 80)," "TRMPKVQQTVQDLFG (SEQ ID NO: 81)," and "RMPKVQQTVQDLFGR (SEQ ID NO: 82)."

[38] A polypeptide, which consists of the amino acid sequence "LFGRAP (SEQ ID NO: 66)."

[39] A method for screening for an anti-mortalin antibody having a cellular internalizing function or a functional fragment thereof, which comprises reacting the polypeptide according to any one of [33] to [38] above with a sample comprising an antibody to be tested.

[40] An anti-mortalin antibody having a cellular internalizing function or a functional fragment thereof, which recognizes the amino acid sequence "LFGRAP (SEQ ID NO: 66)" as an epitope, wherein the antibody is produced using the polypeptide according to any one of [31] to [38] as an immunogen.

[41] A nucleic acid molecule which encodes an epitope that specifically recognizes an anti-mortalin antibody having a cellular internalizing function, wherein the nucleic acid molecule encodes the polypeptide according to any one of [31] to [38] above.

[42] A nucleic acid molecule which encodes a polypeptide that specifically recognizes an anti-mortalin antibody having a cellular internalizing function, wherein the polypeptide comprises a sequence of at least 15 continuous amino acids of the amino acid sequence ranging from amino acid position 310 to position 410 of mortalin 2, and comprises the amino acid sequence of "LFGRAP (SEQ ID NO: 66)."

[43] A method for screening for an anti-mortalin antibody having a cellular internalizing function or a functional fragment thereof, which comprises expressing on a cell surface an epitope to be recognized by an anti-mortalin antibody having a cellular internalizing function by using the nucleic acid molecule according to [41] or [42] above and reacting a sample comprising an antibody to be tested with a cell expressing the epitope.

[44] An agent for accelerating internalization of an anti-mortalin antibody having a cellular internalizing function or a functional fragment thereof, or a drug or a labeling compound bound to the anti-mortalin antibody or functional fragment thereof, into a cancer cell, wherein the agent comprises, as an active ingredient, an expression vector that comprises the nucleic acid molecule according to [41] or [42] above and enables expression of an epitope to be recognized by the anti-mortalin antibody having the cellular internalizing function on the cancer cell surface.

[45] A method for delivering a drug or a labeling compound bound to an anti-mortalin antibody having a cellular internalizing function or a functional fragment thereof into a cancer cell, which is characterized by using an expression vector that comprises the nucleic acid molecule according to [41] or [42] above and enables expression of an epitope to be recognized by the anti-mortalin antibody having the cellular internalizing function on the cancer cell surface.

[46] A polypeptide, which comprises a sequence of at least 8 continuous amino acids selected from the group of partial sequences of the amino acid sequence ranging from amino acid position 410 to position 435 of mortalin 2 and comprises an epitope that specifically recognizes an anti-mortalin antibody not having a cellular internalizing function.

[47] The polypeptide according to [46] above, wherein the amino acid sequence ranging from amino acid position 410 to position 435 of mortalin 2 is the amino acid sequence shown in SEQ ID NO: 30.

Effects of the Invention

According to the present invention, CDR sequences, and H-chain and L-chain variable region sequences each unique to an anti-mortalin antibody having capability of being internalized intracellularly or an anti-mortalin antibody not having such capability are provided. This enables the production of a chimeric antibody, a humanized antibody, or a single-chain antibody having the same function as such anti-mortalin antibody. Further, an anticancer agent that suppresses mortalin activity, within cancer cells in which it is internalized, or on cancer cell surfaces, can be provided. Also, a carrier for delivering a therapeutic drug or a drug for detection into cancer cells can be provided.

Also, a method for identifying and/or evaluating an anti-mortalin antibody using the sequence information of two epitope regions on mortalin can be provided.

Furthermore, according to the present invention, an epitope sequence to be recognized by an anti-mortalin antibody having the internalizing function can be determined. A peptide containing the epitope sequence can be used for screening for an antibody having the cellular internalizing function or a functional fragment thereof. Also, the peptide can be used as an immunogen, so that a peptide antibody having a better internalizing function can be obtained. Such antibody can be used for delivery of an anticancer agent (a low-molecular-weight compound, a toxin, or a nucleic acid molecule such as siRNA) or a labeling molecule (e.g., fluorescent substances, quantum dots, and metal particles) into cancer cells. Then, an expression vector, in which a nucleic acid encoding a polypeptide containing the epitope sequence has been inserted, can be used as an agent for accelerating internalization of an anti-mortalin antibody and a drug with an anti-mortalin antibody as a carrier into cancer cells through expression of the mortalin epitope on cancer cell surfaces.

BRIEF DESCRIPTION OF THE DRAWINGS

FIG. 1 shows the amino acid sequences of the variable regions (paratopes) of each anti-mortalin antibody. The signal sequence, FR1, CDR1, FR2, CDR2, FR3, CDR3 and FR4 sequences for both the heavy and light chains of each antibody is shown as follows:

Figure 3:
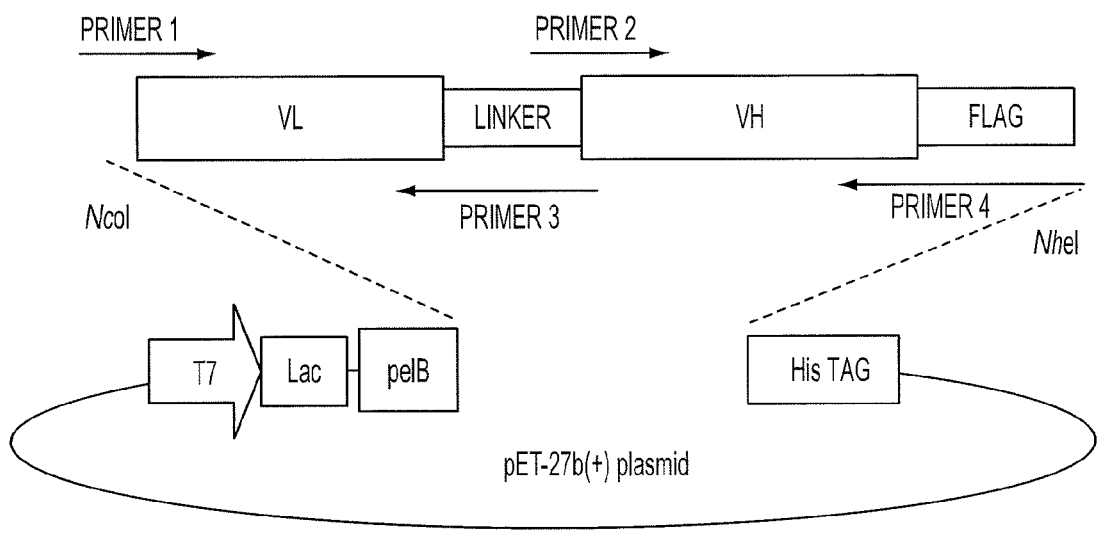

37-1, 37-6, and 96-5 light chain variable regions (signal sequence, residues 1-20 of SEQ ID NO: 4; FR1, residues 21-43 of SEQ ID NO: 4; CDR1, residues 44-59 of SEQ ID NO: 4; FR2, residues 60-74 of SEQ ID NO: 4; CDR2, residues 75-81 of SEQ ID NO: 4, FR3, residues 82-113 of SEQ ID NO: 4, CDR3, residues 114-122 of SEQ ID NO: 4, FR4, residues 123-132 of SEQ ID NO: 4);

38-5 light chain variable region (signal sequence, residues 1-20 of SEQ ID NO: 5; FR1, residues 21-43 of SEQ ID NO: 5; CDR1, residues 44-59 of SEQ ID NO: 5; FR2, residues 60-74 of SEQ ID NO: 5; CDR2, residues 75-81 of SEQ ID NO: 5, FR3, residues 82-113 of SEQ ID NO: 5, CDR3, residues 114-122 of SEQ ID NO: 5, FR4, residues 123-132 of SEQ ID NO: 5);

52-3 light chain variable region (signal sequence, residues 1-21 of SEQ ID NO: 13; FR1, residues 22-44 of SEQ ID NO: 13; CDR1, residues 45-60 of SEQ ID NO: 13; FR2, residues 61-74 of SEQ ID NO: 13; CDR2, residues 76-82 of SEQ ID NO: 13, FR3, residues 83-114 of SEQ ID NO: 13, CDR3, residues 115-123 of SEQ ID NO: 13, FR4, residues 124-133 of SEQ ID NO: 13);

71-1 light chain variable region (signal sequence, residues 1-22 of SEQ ID NO: 9; FR1, residues 23-45 of SEQ ID NO: 9; CDR1, residues 46-56 of SEQ ID NO: 9; FR2, residues 57-71 of SEQ ID NO: 9; CDR2, residues 72-78 of SEQ ID NO: 9, FR3, residues 79-110 of SEQ ID NO: 9, CDR3, residues 111-119 of SEQ ID NO: 9, FR4, residues 120-129 of SEQ ID NO: 9);

37-1 and 37-6 heavy chain variable regions (signal sequence, residues 1-19 of SEQ ID NO: 17; FR1, residues 20-49 of SEQ ID NO: 17; CDR1, residues 50-54 of SEQ ID NO: 17; FR2, residues 55-68 of SEQ ID NO: 17; CDR2, residues 69-85 of SEQ ID NO: 17, FR3, residues 86-117 of SEQ ID NO: 17, CDR3, residues 118-120 of SEQ ID NO: 9, FR4, residues 121-131 of SEQ ID NO: 17);

38-5 heavy chain variable region (signal sequence, residues 1-19 of SEQ ID NO: 20; FR1, residues 20-49 of SEQ ID NO: 20; CDR1, residues 50-54 of SEQ ID NO: 20; FR2, residues 55-68 of SEQ ID NO: 20; CDR2, residues 69-85 of SEQ ID NO: 20, FR3, residues 86-117 of SEQ ID NO: 20, CDR3, residues 118-120 of SEQ ID NO: 20, FR4, residues 121-131 of SEQ ID NO: 20);

96-5 heavy chain variable region (signal sequence, residues 1-19 of SEQ ID NO: 19; FR1, residues 20-49 of SEQ ID NO: 19; CDR1, residues 50-54 of SEQ ID NO: 19; FR2, residues 55-68 of SEQ ID NO: 19; CDR2, residues 69-85 of SEQ ID NO: 19, FR3, residues 86-117 of SEQ ID NO: 19, CDR3, residues 118-120 of SEQ ID NO: 19, FR4, residues 121-131 of SEQ ID NO: 19);

52-3 heavy chain variable region (signal sequence, residues 1-19 of SEQ ID NO: 28; FR1, residues 20-49 of SEQ ID NO: 28; CDR1, residues 50-54 of SEQ ID NO: 28; FR2, residues 55-68 of SEQ ID NO: 28; CDR2, residues 69-85 of SEQ ID NO: 28, FR3, residues 86-117 of SEQ ID NO: 28, CDR3, residues 118-128 of SEQ ID NO: 28, FR4, residues 129-139 of SEQ ID NO: 28);

71-1 heavy chain variable region (signal sequence, residues 1-19 of SEQ ID NO: 24; FR1, residues 20-49 of SEQ ID NO: 24; CDR1, residues 50-54 of SEQ ID NO: 24; FR2, residues 55-68 of SEQ ID NO: 24; CDR2, residues 69-87 of SEQ ID NO: 24, FR3, residues 88-119 of SEQ ID NO: 24, CDR3, residues 120-125 of SEQ ID NO: 24, FR4, residues 126-136 of SEQ ID NO: 24).

FIG. 2 shows the IgG subtype of each mortalin.

FIG. 3 is a schematic view of a plasmid expressing an scFv against mortalin. A DNA fragment in which the VL domain and the VH domain are linked via a linker and a FLAG tag sequence is added thereto was cloned into the Nco I and Nhe I sites of a pET-27b(+) plasmid vector.

FIG. 4 shows each primer sequence (5' terminus on the left and the 3' terminus on the right) used for construction of scFv. The bottom part shows the nucleotide (SEQ ID NO: 83) and amino acid (SEQ ID NO: 84) sequence of a pET-27b(+) plasmid containing multicloning sites.

Figure 5:
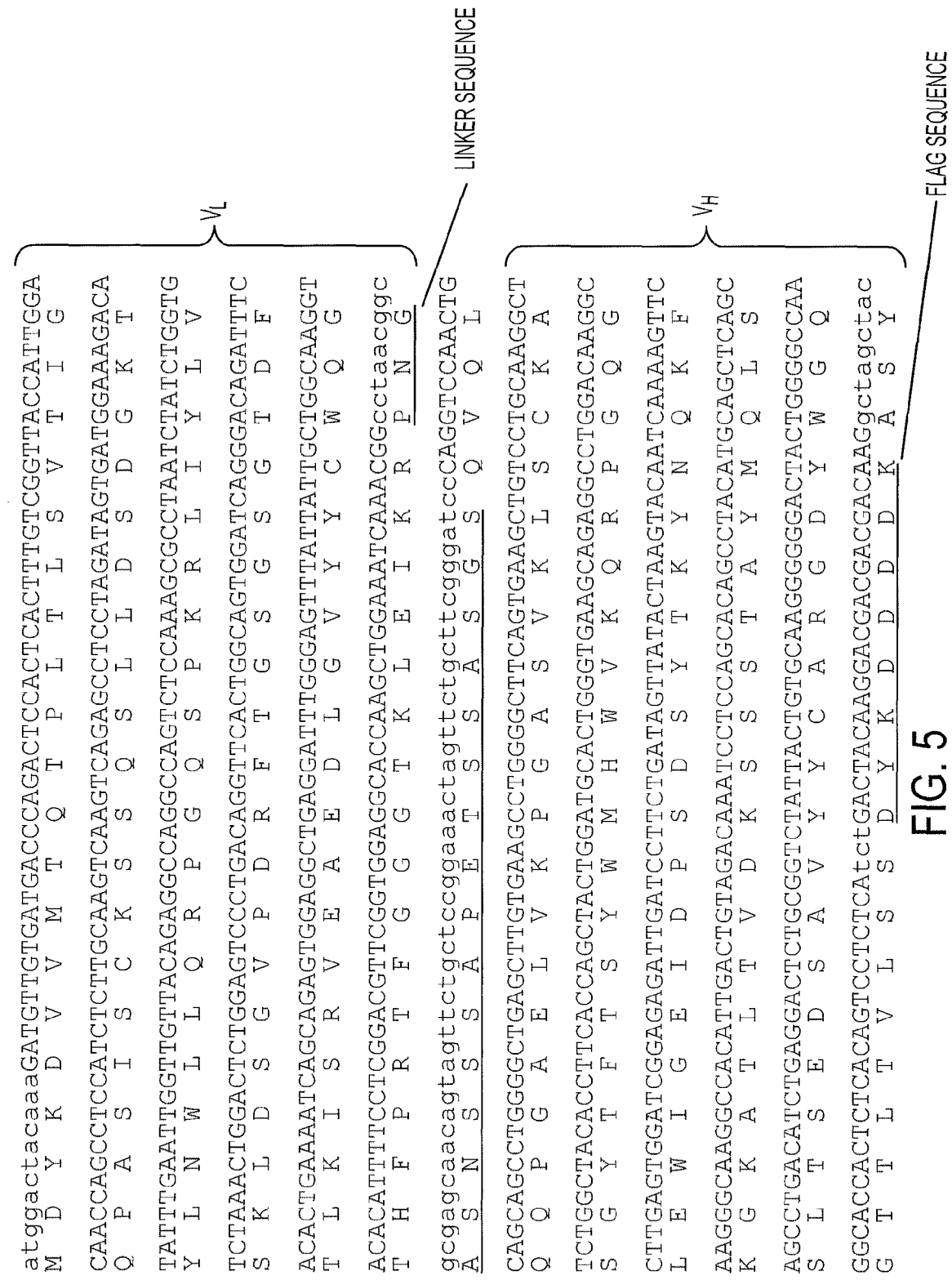

FIG. 5 shows the DNA sequence (SEQ ID NO: 85) and the amino acid sequence (SEQ ID NO: 86) of scFv expected to be expressed. A linker portion and a FLAG tag sequence portion are underlined.

FIG. 6 shows the expression induction and purification of scFv against mortalin in *Escherichia coli*. Protocols for purification of scFv from the periplasm is shown on the left. SDS-PAGE analysis results of the proteins before and after expression induction by IPTG and after purification are shown on the right. Induced protein expression was observed by addition of IPTG at about 30 kDa. Almost single band could be obtained by purification with His tag.

FIG. 7 shows the affinity of monoclonal antibodies and scFv for recombinant mortalin, as anlyzed by ELISA. It was confirmed that scFv bound to the recombinant mortalin with a dissociation constant of approximately 10 nM.

FIG. 8 shows deletion proteins of mortalin. Binding between each deletion protein and an anti-mortalin antibody (38-4, 52-3, or 96-5) was detected by BIACORE. The 3 types of anti-mortalin antibodies bound to full-length mortalin, but the 52-3 anti-mortalin antibody bound to only a deletion protein containing the C-terminal amino acid sequence. The epitope of the 52-3 antibody was considered to be a peptide between amino acid residues 403 and 435 of mortalin.

FIG. 9 shows the binding between each deletion protein and the anti-mortalin antibody (38-4, 52-3, or 96-5) as detected by ELISA. After physical adsorption of the deletion proteins to wells, the anti-mortalin antibody (38-4, 52-3, or 96-5) was added.

After washing, alkaline phosphatase modification anti-mouse IgG was added and then the degree of binding was measured using a substrate (reactant) having absorption at 405 nm. Table shows absorbance at 405 nm. It was considered that the epitope of the 38-4 or the 96-5 antibody was located within the range of amino acid residues 310-410 of mortalin; and it was also considered that the epitope of the 52-3 antibody was located within the range of amino acid residues 403-435 of mortalin.

Figure 10:
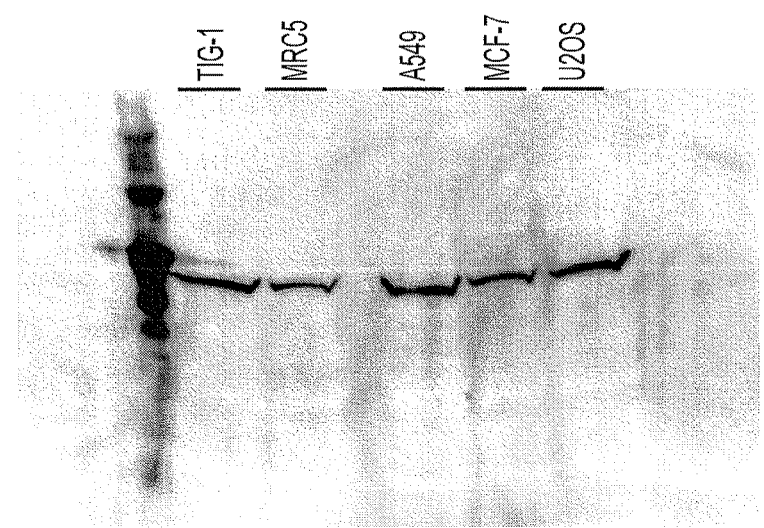

FIG. 10 shows detection of mortalin by Western blotting using scFv. Western blotting analysis was conducted using scFv as a primary probe, revealing that specific detection of the band of mortalin was possible. Detection was carried out using a histidine tag added to the C-terminus of scFv.

Figure 11:
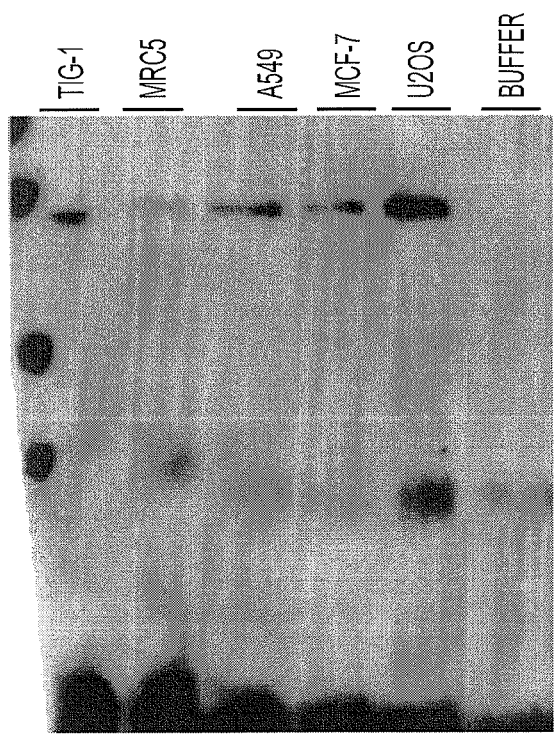

FIG. 11 shows the results of immunoprecipitation of mortalin in cell lysates using scFv. After recovery of scFv using an anti-His antibody, coprecipitation of mortalin could be confirmed by Western blotting.

FIG. 12 shows presumed epitope regions that are recognized by anti-mortalin antibodies having capability of being internalized intracellularly or not having such capability. Interaction between deletion mutants of mortalin and anti-mortalin antibodies was analyzed by (A) ELISA and (B) BIAcore. (C) shows the binding regions in full-length mortalin between the anti-mortalin antibodies not having such capability of being internalized intracellularly and anti-mortalin antibodies having such capability.

FIG. 13 shows the homology between human (SEQ ID NO: 57) and mouse (SEQ ID NO: 61) amino acid sequences (as determined by a BLAST method).

FIGS. 14a and 14b show a peptide array comprising 89 peptides (peptides 1-89 are identified by SEQ ID NOs: 87-175, respectively). Each peptide is 15 amino acids in length, prepared by shifting the 348-450 region of mortalin by one amino acid at a time. Peptides recognized with the use of antibodies are indicated with arrows.

Figure 15:
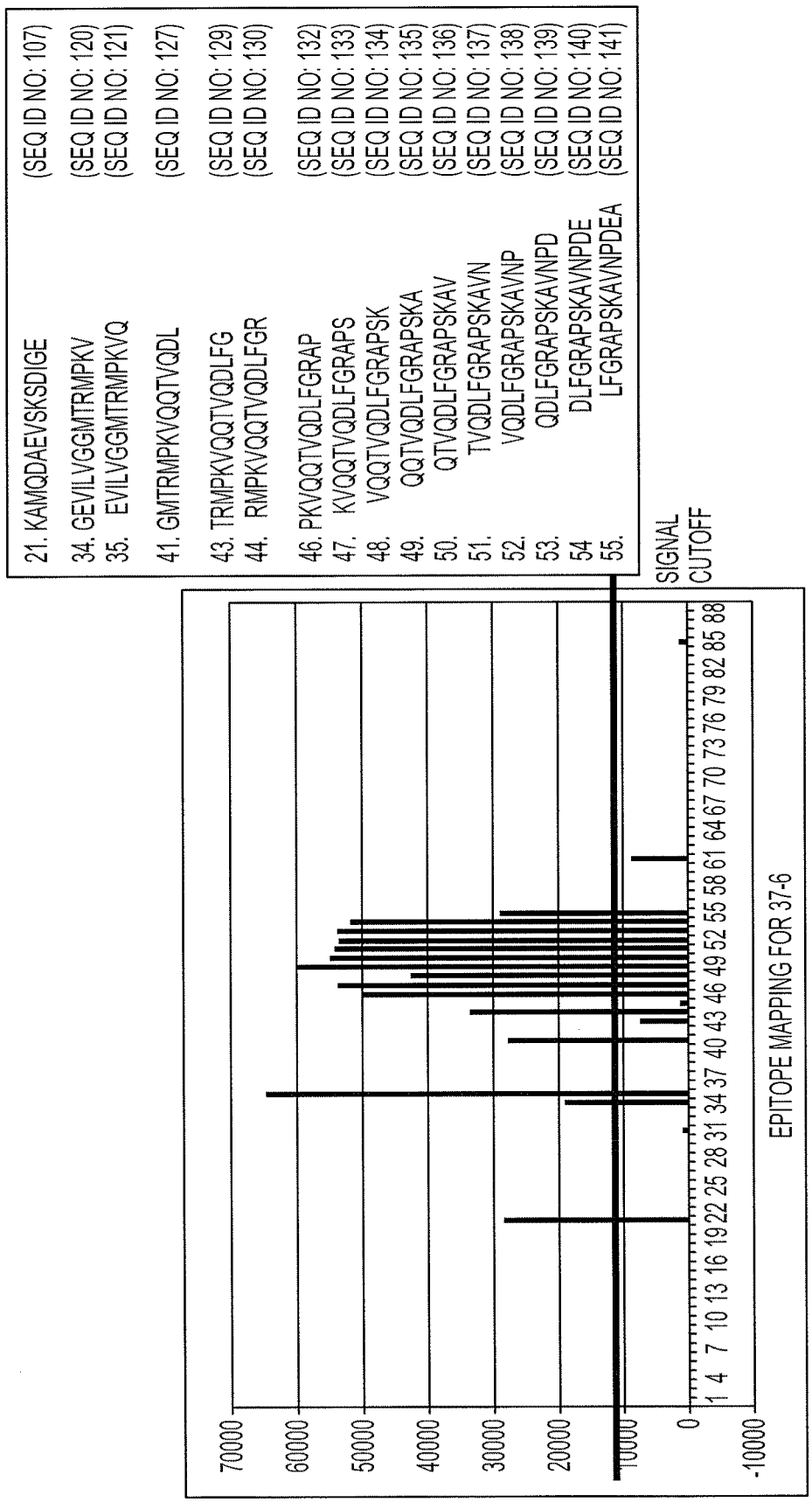

FIG. 15 shows binding signals of peptides that bound to the antibody 37-6. The peptides binding to the antibody and their sequences are shown in the inserted figure.

Figure 16:
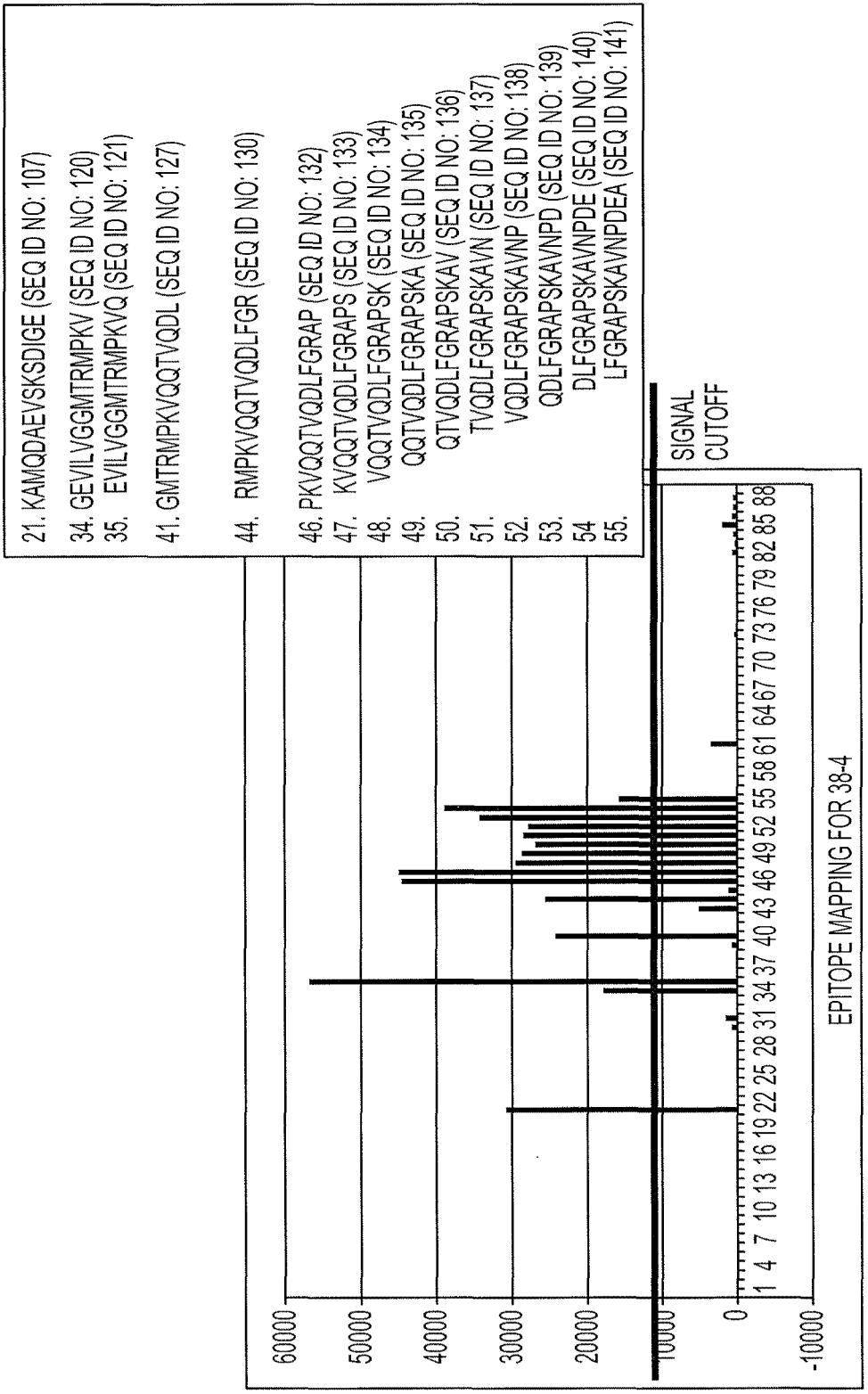

FIG. 16 shows binding signals of peptides that bound to the antibody 38-4. The peptides binding to the antibody and their sequences are shown in the inserted figure.

Figure 17:
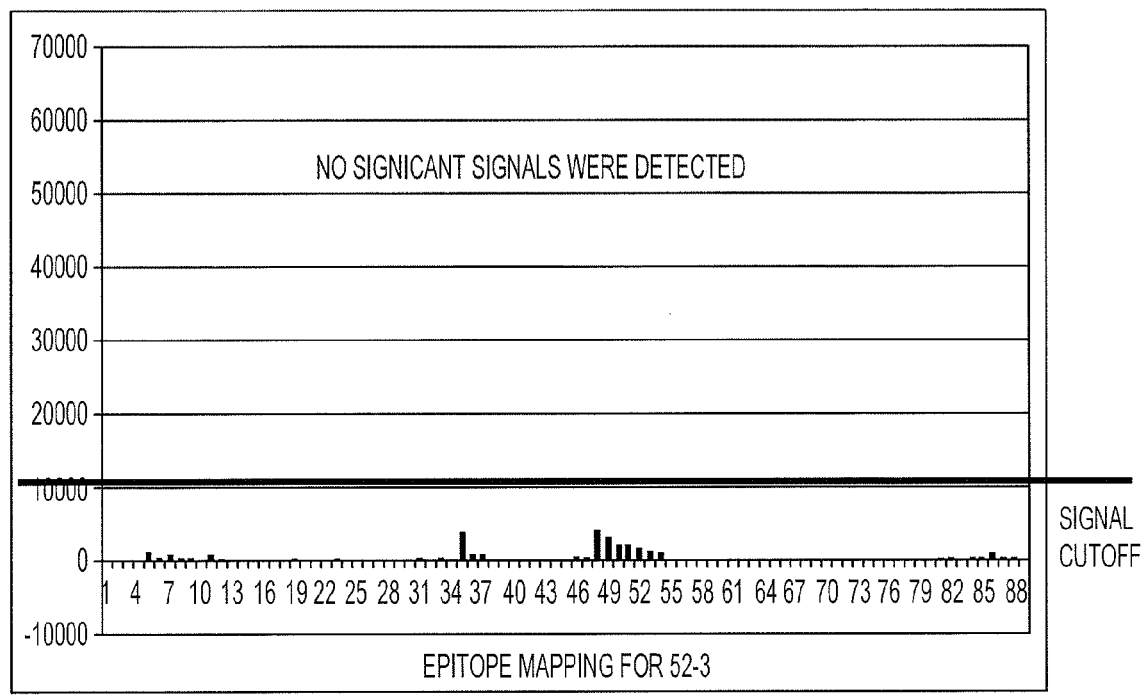

FIG. 17 shows binding signals of peptides that bound to the antibody 52-3. No peptides that bound to the antibody were observed.

FIG. 18 shows RepliTope data summary for peptides 18-58 (SEQ ID NOs: 104-144, respectively). Six (6) amino acids, LFGRAP (SEQ ID NO: 66), which were commonly contained between peptides #46 and #55, were identified as an epitope. Other peptides (#21, 34, 35, 41, 43, and 44) indicated with arrows were also recognized by internalizing antibodies.

FIG. 19 (Reference drawing 1) shows the synthetic scheme for a PEI-imot Ab conjugate.

FIG. 20 (Reference drawing 2) shows gel retardation assay. PEI-imotAb and plasmid DNA were mixed at N/P ratios of 0, 1, 2, 5, 7.5, and 10, followed by 0.8% agarose gel electrophoresis. Subsequently, ethidium bromide staining was carried out, so that DNA was detected.

Figure 21:
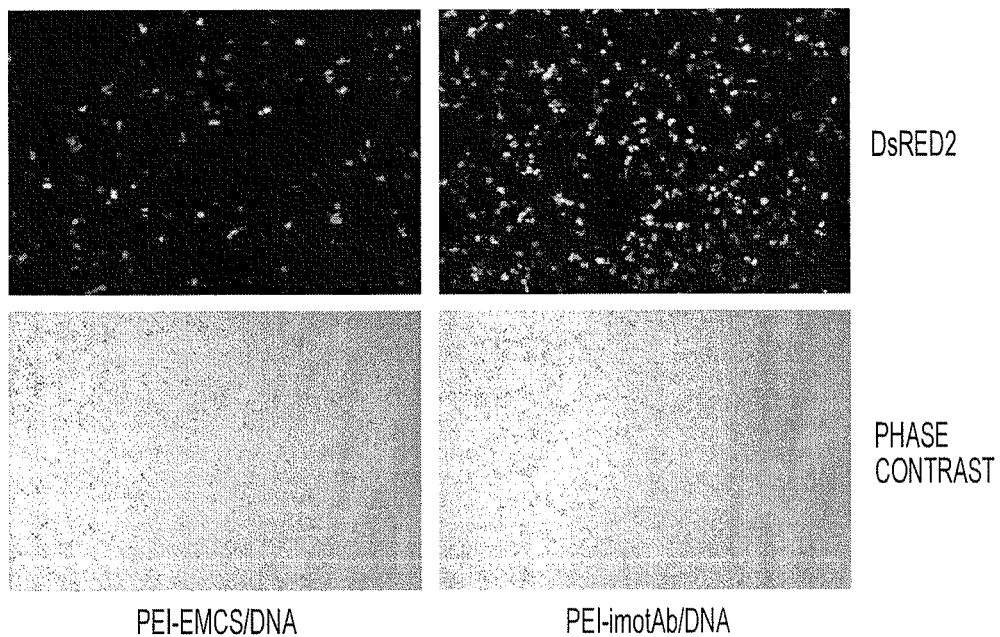

FIG. 21 (Reference drawing 3) shows gene delivery using i-Porter (PEI-imotAb/DNA polyplexes). Plasmid DNA encoding DsRed2 was used and then cells were observed via fluorescence microscopy after delivery. A conjugate of a PEI and DNA bound thereto via crosslinker was used as a control.

Figure 22:
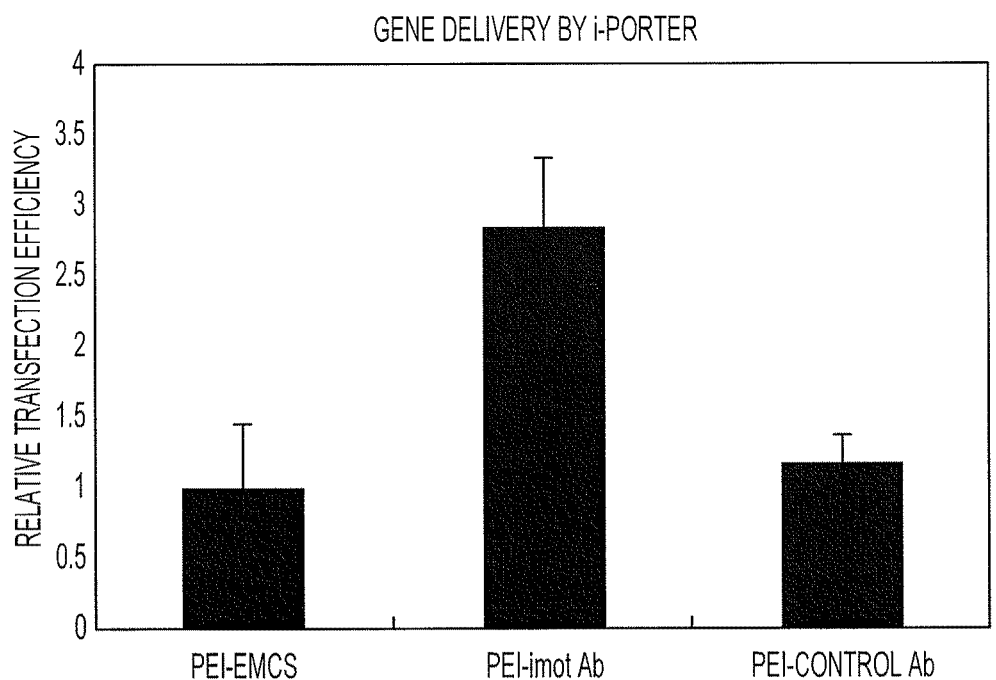

FIG. 22 (Reference drawing 4) shows gene delivery using i-Porter (PEI-imotAb/DNA polyplexes). Plasmid DNA encoding Renilla luciferase was used and then gene delivery and expression efficiency were measured based on normalized luciferase activity. Comparison was made with PEI-control Ab/DNA polyplex in which control Ab recovered from bovine serum had been bound as a control.

Figure 23:
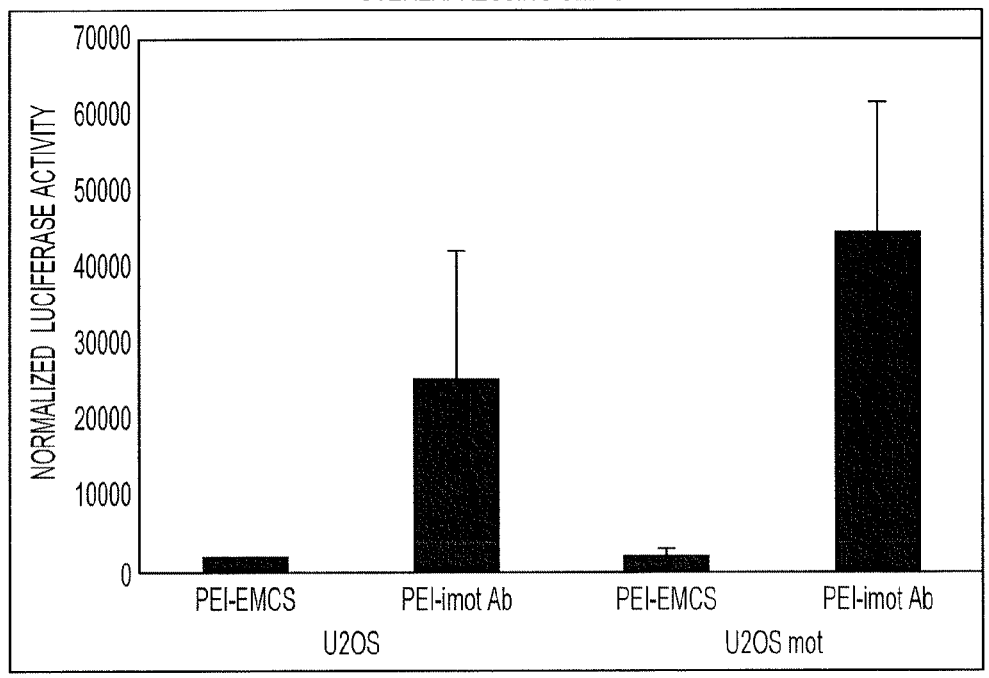

FIG. 23 (Reference drawing 5) shows gene delivery in a general U2OS cell line and an U2OS mot cell line (that is a cell line overexpressing mortalin) using i-Porter (PEI-imotAb/DNA polyplex). Plasmid DNA encoding Renilla luciferase was used and then gene delivery and expression efficiency were measured based on normalized luciferase activity.

Figure 24:
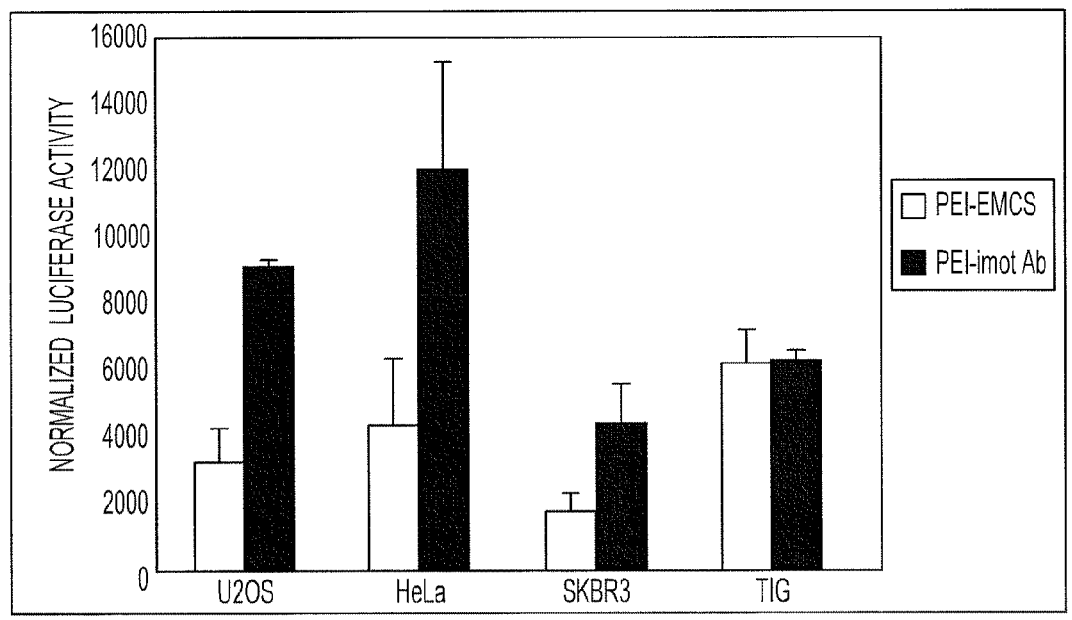

FIG. 24 (Reference drawing 6) shows a gene delivery comparison using i-Porter (PEI-imotAb/DNA polyplexe) in cancer cells (U2OS, SKBR3, and HeLa) and normal cells (TIG-1). Plasmid DNA encoding Renilla luciferase was used and then gene delivery and expression efficiency were measured based on normalized luciferase activity.

Figure 25:
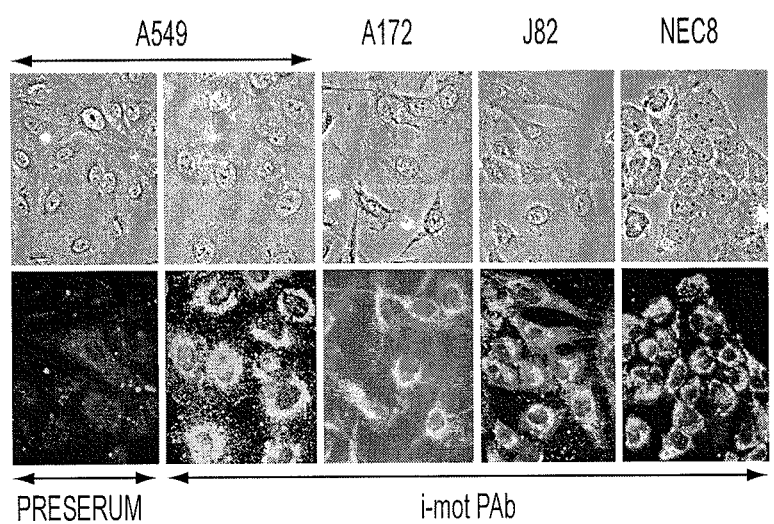

FIG. 25 (Reference drawing 7) shows an experiment of delivery of anti-mortalin polyclonal antibodies modified with fluorescent quantum dots into A549 (lung cancer cells), A172 (glioblastoma cells), J82 (urothelial cancer cells), and NEC8 (human embryonal cancer cells).

BEST MODE FOR CARRYING OUT THE INVENTION

1. Definition of Terms
(1) Mortalin 2 and Anti-Mortalin Antibody

In the present invention, the term "mortalin" or "mortalin 2" refers to mouse mortalin 2 (mot-2) or human mortalin 2 (hmot-2).

Also, the term "anti-mortalin antibody" refers to either an antibody against mouse mortalin 2 or an antibody against human mortalin 2. Mouse and human mortalin proteins have very high homology with each other, so that an antibody prepared against mouse mortalin 2 recognizes a human mortalin protein or vice versa.

Hence, anti-mortalin antibody-producing hybridomas used in the embodiments of the present invention produce mouse monoclonal antibodies prepared via immunization of mice with full-length mouse mortalin 2. A specific method for producing such anti-mortalin monoclonal antibody-producing hybridomas is carried out according to the present inventors' International Patent Publication WO2006/022344 A1 and JP Patent Publication (Kokai) No. 2006-89471 A.

(2) Anti-Mortalin 2 Antibody having Internalizing Function

As described above, anti-mortalin monoclonal antibodies specifically binding to mortalin 2 include two types of antibodies: antibodies having a internalizing function (capability of being internalized intracellularly) into cancer cells; and antibodies not having such function, but binding to mortalin 2 on cancer cell surfaces. The former antibodies are referred to as "anti-mortalin antibodies having the internalizing function" and the latter antibodies are referred to as "anti-mortalin antibodies not having the internalizing function." They may be simply referred to as "antibodies having the internalizing function" or "antibodies not having the internalizing function." A variable region from each antibody is also referred to as "an antibody variable region having the internalizing function" or "an antibody variable region not having the internalizing function." They have their own unique different sequences, and in particular, the CDR sequences thereof have nothing in common.

Here, the anti-mortalin antibody having or not having the internalizing function of the present invention recognizes mortalin that is specifically present on cancer cell surfaces and then undergoes transfer into cancer cells via the mortalin or remains on cancer cell surfaces without such transfer. Here, the term "cancer cells" refers to general cancer cells and examples thereof include, but are not limited to, bone cancer cells, breast cancer cells, fibrosarcoma cells, cervical cancer cells, lung cancer cells, glioblastoma cells, urothelial cancer cells, liver cancer cells, and human embryonal cancer cells.

In the present invention, the term "anti-mortalin antibody" refers to an anti-mortalin monoclonal antibody that is composed of a pair of H chain and L chain, or a fragment antibody thereof having similar functions. Such fragment antibody includes, for example, H-chain and L-chain variable regions, a Fab fragment comprising those variable regions, and an antibody comprising one H chain and one L chain having free SH groups.

The hybridomas producing these antibodies can be prepared by conventional means using antibody-producing cells obtained via immunization of general experimental animals such as mice, rats, or rabbits or using human-derived anti-mortalin antibody-producing lymphocytes directly obtained from cancer patients. The present invention is directed to a "recombinant anti-mortalin antibody" that has been expressed using cDNA obtained from such hybridomas in an appropriate host cell system such as mammalian cells (e.g., CHO cells), bacterial cells (e.g., *Escherichia coli*), or yeast cells. Examples of such recombinant anti-mortalin antibody include a recombinant antibody comprising one H chain and one L chain, a recombinant single-chain antibody (scFv) in which an H-chain variable region and an L-chain variable region are linked via a linker, and an antibody fragment such as recombinant Fab, which have the cellular internalizing function. Examples of the same also include chimeric antibodies and humanized antibodies prepared using the above unique variable region sequences or CDR sequences.

In the embodiments of the present invention, 5 types of "anti-mortalin antibody having the internalizing function" and 1 type of "anti-mortalin antibody not having the internalizing function" were used to determine the amino acid sequences of the variable regions. The amino acid sequences were compared and then sequential characteristics of particularly L chains in a case of having the internalizing function and the same in a case of not having such function were examined as described below.

(3) Single-Chain Antibody and Expression Vector

In the present invention, the term "single-chain antibody" also refers to "scFv (single chain Fv)," which corresponds to a product prepared by linking heavy-chain and light-chain variable regions (VH and VL) of an anti-mortalin antibody via an appropriate peptide linker (Huston J S, Levinson D, Mudgett-Hunter M, Tai M S, Novotny J, Margolies M N, Ridge R J, Bruccoleri R E, Haber E, Crea R, et al. Protein engineering of antibody binding sites: recovery of specific activity in an anti-digoxin single-chain Fv analogue produced in *Escherichia coli*. Proc Natl Acad Sci U.S.A. 1988 August; 85 (16): 5879-83). Such construct was constructed at the gene level and then introduced into *Escherichia coli* using a protein expression vector, so that a single-chain antibody protein can be expressed.

In the embodiments of the present invention, a linker sequence comprising a non-repetitive sequence (used by Luginbuhl et al., Luginbuhl, B., Kanyo, Z., Jones, R. M., Fletterick, R. J., Prusiner, S. B., Cohen, F. E., Williamson, R. A., Burton, D. R., and Pluckthun, A. (2006) J Mol Biol 363, 75-97) was used. Appropriate setting is possible with the use of only approximately 5 to 20 amino acids.

As host cells for expression and expression vectors, combinations of various generally employed host cells and vectors appropriate for the host cells can be adequately selected. With the use of an expression vector constructed by introducing a signal sequence (PelB sequence) for transport to an *Escherichia coli* periplasmic region, a single-chain antibody (scFv) can be simply obtained by causing expression of the gene in *Escherichia coli* and the following secretion within the periplasmic region. In an embodiment of the present application, scFv sequences prepared via amplification using 2 types of primer sets from the cDNA pool of each antibody were each cloned into a "pET-27b(+) plasmid" that is an expression plasmid vector having a PelB sequence.

A single-chain antibody composed only of variable region sequences unique in a cellular internalizing anti-mortalin antibody has been confirmed to be capable of specifically binding to mortalin. Such single-chain antibody is also expected to have a internalizing function into cancer cells, indicating a possible use of such antibody as an anticancer agent that specifically binds to mortalin within cancer cells, so as to suppress mortalin activity. The antibody can also be used as a drug carrier carrying another drug for cancer treatment, such as a low-molecular-weight compound that suppresses mortalin activity, a nucleic acid carrier coupled to a cationic polymer or the like, by which a gene for gene therapy is delivered into cells to be able to function, and a carrier for cancer cell detection, which is prepared by binding a fluorescent substance or the like thereto (the nucleic acid carrier was disclosed in the patent application JP Patent Application No. 2007-141073 having the same priority date as the present application).

A single-chain antibody prepared using variable regions not having the cellular internalizing function is similarly useful as an anticancer agent, a drug carrier, or a carrier for cancer cell detection, since its properties of specifically binding to mortalin on cancer cell surfaces can be used.

(4) Reduced Antibody (the Antibody Comprising one H Chain and one L Chain having Free SH Groups)

For example, a reduced antibody can be simply obtained by adding dithiothreitol (DTT) to an antibody, reacting them for approximately 30 minutes at room temperature, and then removing DTT using a demineralization column or the like (a specific production method therefor is as disclosed in the patent application JP Patent Application No. 2007-141073). Any method may be employed, as long as it is a reduction method by which a free SH group can be formed.

A recombinant anti-mortalin reduced antibody in the present invention can be produced by a gene recombination technique using cDNAs encoding H and L chains.

(5) Chimeric Antibody and CDR Antibody

Examples of the anti-mortalin antibody of the present invention include chimeric antibodies and humanized antibodies that are produced by conventional methods described below. Specifically, a CDR antibody (humanized antibody) can be prepared by: binding a DNA that encodes a variable region from an anti-mortalin antibody having the cellular internalizing function, which is obtained according to the present invention, to a DNA that encodes a constant region of a human-derived antibody and then causing expression by a general recombination technique, so as to prepare a chimeric antibody; or ligating DNAs encoding the CDR1-3 regions to DNAs encoding a framework region and a constant region of a human-derived antibody according to the Dall'Acqua's technique (Dall'Acqua W F, Damschroder M M, Zhang J, Woods R M, Widjaja L, Yu J, Wu H. Antibody humanization by framework shuffling. Methods. 2005 May; 36 (1): 43-60.) and then causing expression.

(6) Epitope

In the present invention, the term "epitope" refers to a region corresponding to an amino acid sequence that is recognized by an anti-mortalin antibody having or not having capability of being internalized intracellularly, in the full-length amino acid sequence of mortalin. Specifically, such epitope corresponding to an antibody having the capability of being internalized intracellularly binds to any one of or all of CDRs corresponding to paratopes of antibodies having the capability of being internalized intracellularly. More specifically, such epitope binds to one or more sequences selected from among: the CDR1 sequence, "KSSQSLLDSDGK-TYLN (SEQ ID NO: 1)," of the L-chain variable region of an anti-mortalin antibody having the cellular internalizing function, the CDR2 sequence, "LVSKLDS (SEQ ID NO: 2)," of the same, the CDR3 sequence, "WQGTHFPRT (SEQ ID NO: 3)," of the same, the CDR1 sequence, RASQEISGYLS (SEQ ID NO: 6)," of the same, the CDR2 sequence, "AASTLDS (SEQ ID NO: 7)," of the same, the CDR3 sequence, "LQYASYPPT (SEQ ID NO: 8)," of the same; and the CDR1 sequence, "SYWMH (SEQ ID NO: 14)," of the H chain variable region of the same, the CDR2 sequence, "EIDPSD-SYTKYNQKFKG (SEQ ID NO: 15)" or "EIDPSDSYT-DYNQNFKG (SEQ ID NO: 18)," of the same, and the CDR3 sequence, "GDY (SEQ ID NO: 16)," of the same.

Meanwhile, an epitope corresponding to an antibody not having the capability of being internalized intracellularly binds to any one of or all of CDRs corresponding to the paratopes of antibodies that are not internalized intracellularly. Specifically, such epitope binds to one or more sequences selected from among: the CDR1 sequence, "RSSKSLLYSNGITYLY (SEQ ID NO: 10)," of the L-chain variable region of a recombinant anti-mortalin antibody not having the cellular internalizing function, the CDR2 sequence, "QMSNLAS (SEQ ID NO: 11)," of the same, and the CDR3 sequence, "AQNLELPWT (SEQ ID NO: 12)," of the same; and the CDR1 sequence, "SYWMH (SEQ ID NO: 25)," of the H-chain variable region of the same, the CDR2 sequence, "EINPSNGRTNYNEKFKS (SEQ ID NO: 26)," of the same, and the CDR3 sequence, "SRYYGSCYFDY (SEQ ID NO: 27)," of the same.

An epitope that is recognized by an anti-mortalin antibody having the cellular internalizing function of the present invention is considered to comprise, in the amino acid sequence of mortalin, continuous or non-continuous 5 to 8 amino acid residues existing in the region ranging from position 381 to position 410 of the amino acid sequence (SEQ ID NO: 56) that is common in human mortalin 2 and mouse mortalin 2. Typically, such epitope comprises a sequence of continuous 8 amino acid residues, preferably a sequence of continuous 10 amino acid residues, more preferably a sequence of continuous 15 amino acid residues, and most preferably a sequence of continuous 20 amino acid residues from the amino acid sequence of SEQ ID NO: 55 or 62.

Mortalin 2 is extremely highly conserved across species. For example, human mortalin 2 and mouse mortalin 2 share amino acid sequence homology of 97.9% as determined by BLAST method (FIG. 13). Accordingly, in the description, typical mouse-derived and human derived sequences are shown, but the examples are not limited thereto. An epitope region of mortalin 2 of another species, which is recognized by an anti-mortalin antibody having the capability of being internalized intracellularly, is also present in the region ranging from position 381 to position 410 of the amino acid sequence of mortalin 2.

Hence, an epitope mapping method was applied to a region ranging from position 348 to position 450 containing a region ranging from position 381 to position 410 shown in SEQ ID NO: 56 above. As a result, the peptide regions shown in SEQ ID NOS: 67 to 76 that are binding sequences specific to an internalizing antibody and their common sequence of 6 amino acids "LFGRAP (SEQ ID NO: 66)" as an epitope sequence were determined. Furthermore, binding sequences specific to such internalizing antibody were successfully determined (SEQ ID NOS: 77-82). The use of peptides containing each of these sequences enables screening for antibodies having the cellular internalizing function or functional fragments thereof. Moreover, the use of such peptides as immunogens enables preparation of peptide antibodies further excellent in the internalizing function.

Also, a nucleotide sequence encoding an amino acid sequence comprising the above-mentioned epitope sequence, for example, an expression vector comprising a nucleic acid that encodes a peptide comprising a partial sequence from SEQ ID NO: 60 or 65 that contains SEQ ID NO: 66, is used to express the epitope of interest in large amounts on cancer cell surfaces, such that the epitope acts as a target region upon delivery. For example, in the method, an anti-mortalin antibody having the capability of being internalized intracellularly can be bound to cancer cell surfaces to assist the internalization of the anti-mortalin antibody into cancer cells. That is, the expression vector can be used as an agent for accelerating the delivery into cancer cells or an agent for accelerating internalization of an anti-mortalin antibody or an anticancer agent or test reagent bound to anti-mortalin antibody. Furthermore, a sample (e.g., blood, body fluids, and cell culture solutions) comprising an anti-mortalin antibody to be tested can be reacted with a synthetic peptide comprising the epitope on a substrate or in a solution, or contacted with cells expressing the epitope, to detect the presence or the absence of the internalizing function into cancer cells for the anti-mortalin antibody. Hence, an anti-mortalin antibody or a functional fragment thereof having even higher internalizing function can be screened for by the detection.

2. Nucleic Acid Carriers and Drug Carriers Using Anti-Mortalin Antibodies having the Internalizing Function into Cancer Cells The anti-mortalin antibody having the cellular internalizing function of the present invention recognizes mortalin specifically existing on cancer cell surfaces and is then transferred into cancer cells via the mortalin. Cancer cells, into which a carrier comprising the anti-mortalin antibody of the present invention used therein can transport a nucleic acid into the cells, may be any general cancer cells. Examples of such cancer cells include, but are not limited to, bone cancer cells, breast cancer cells, fibrosarcoma cells, cervical cancer cells, lung cancer cells, glioblastoma cells, urothelial cancer cells, liver cancer cells, and human embryonal cancer cells.

In Reference examples 4 and 5 as described below of the present invention, it was confirmed by the use of typical cancer cells from among the above cancer cells that an anti-mortalin antibody having the cellular internalizing function can be internalized into any of the cancer cells used.

For nucleic acid carriers in the Reference examples of the present invention, as a cationic polymer to be bound to an anti-mortalin antibody that is internalized intracellularly, a cationic polymer having positive (+) charge known as a nucleic acid carrier can be used, such as polyethylenimine (PEI produced by Aldrich, for example), poly L-lysine (PLL), polylysine, and liposome. Thus, direct binding to or indirect binding via a known crosslinker agent to an antibody is possible.

Any linker agent can be adequately used as a crosslinker for binding. Various crosslinker agents are commercially available from Dojindo, Pierce and the like. In the Reference examples of the present invention, N-(6-Maleimidocaproyloxy)succinimide (EMCS; Dojindo) was used.

As a target nucleic acid that forms a molecular conjugate with a nucleic acid carrier, is introduced specifically into cancer cells, and can be caused to function in the Reference examples of the present invention, nucleic acids having anticancer effects on cancer cells or nucleic acids for detection and identification of cancer cells can be used, for example. In the cases of DNA, examples thereof may be either cases where a DNA having its own anticancer activity or cases where the expression product thereof has anticancer activity, such as a DNA that itself or the expression product thereof leads cancer cells to undergo apoptosis, an antisense DNA, and a DNA encoding an expression product having cytotoxicity (e.g., IFN, TNF, various cytokines, and enzymes). Similarly, reporter genes such as a luciferase gene or labeled DNA, which can be used for identification or detection of cancer cells, can be used. The effects of an anticancer agent can be monitored in real-time through the use of such reporter gene or labeled DNA with a nucleic acid exerting anticancer effects. Such DNA is directly used or used as a recombinant DNA or used in a form incorporated in a recombinant vector such as a known virus or an expression plasmid. Also, RNA such as mRNA, siRNA, or ribozyme can also be used.

In the Reference examples, as a model embodiment, typical polyethylenimine (PEI) among cationic polymers was bound to an anti-mortalin antibody (i-mot Ab) using a commercially available crosslinker to produce a carrier for introducing nucleic acids (PEI-imot Ab) was produced.

Subsequently, a conjugate of PEI-imot Ab and a plasmid DNA was cultured with cells, thereby the plasmid DNA was successfully introduced into cells in an anti-mortalin-antibody-dependent manner. Then the expression of a luciferase gene introduced as a model system into the plasmid DNA was confirmed.

A conjugate was formed herein with the plasmid DNA encoding luciferase as a model system. It is naturally possible to introduce various nucleic acids including a DNA and an RNA into cells with the use of a polyethylenimine-anti-mortalin antibody conjugate. Moreover, such anti-mortalin antibody having the cellular internalizing function can be used not only as a nucleic acid carrier, but also as a drug carrier into cancer cells through its binding to various known therapeutic drugs such as anticancer agents, and drugs for detection.

When used as an anticancer agent, an anti-mortalin antibody can be formulated according to a conventional method (Remington's Pharmaceutical Science, latest edition, Mark Publishing Company, Easton, U.S.A.). The agent may contain both pharmaceutically acceptable carrier and an additive. The agent is generally administered via the route of parenteral administration. For example, the agent is administered in the form of an injection preparation (e.g., subcutaneous injection, intravenous injection, intramuscular injection, and intraperitoneal injection). The agent is also administered via transdermal, transmucosal, nasal, or pulmonary administration, for example. Oral administration thereof is also possible (see, e.g., International Patent Publication WO2006/022344 A1 and JP Patent Publication (Kokai) No. 2006-89471 A).

Also, the amount of a substance such as a nucleic acid bound to the anti-mortalin antibody having the cellular internalizing function of the present invention, which is contained in a preparation, can be determined depending on the type of a disease to be treated, severity of the disease, the age of the patient, and the like.

3. Experimental Methods in the Present Invention

Specific embodiments according to the Examples of the present invention are as described below, but the present invention is not limited thereto.

(1) Sequencing of Variable Regions

A hybridoma producing an anti-mortalin antibody is cultured and then total RNA is extracted. A first 1st-strand cDNA synthesis is carried out using the thus obtained RNA as a template and 5'CDS primers.

Subsequently, touch down PCR is carried out using the 1st-strand cDNA as a template and an Advantage 2 PCR Kit (Clontech, cat. No. K1910-y).

At this time, gene-specific primers to be used herein are designed for the 5' of H-chain and L-chain constant regions, respectively, followed by selection based on antibody subtypes. Primer sequences are as follows.

```
H chain
MHC-IgG1
                                    (SEQ ID NO: 36)
GGGCCAGTGGATAGACAGATG MHC-IgG2a
                                    (SEQ ID NO: 40)
CAGGGGCCAGTGGATAGACCGATG MHC-IgG2b
                                    (SEQ ID NO: 40)
CAGGGGCCAGTGGATAGACTGATG MHC-IgG3
                                    (SEQ ID NO: 39)
CAGGGACCAAGGGATAGACAG L chain
MLC-kappa
                                    (SEQ ID NO: 176)
GCTCACTGGATGGTGGGAAGATG
```

The thus obtained RACE product is subjected to agarose gel electrophoresis, target bands are excised, and then gel extraction (QIAGEN) is carried out. To enhance cloning efficiency, TA cloning may be adequately carried out using a pGEM-T Easy vector (Promega).

Clones in which the target gene has been inserted are selected by colony PCR. In addition, DNA preparation is carried out for 6 or more clones in order to determine a single sequence. Sequencing is carried out using vector primers as follows. Specifically, hybridoma-derived pseudo sequences and sequences containing termination codons in the middle of the sequences are eliminated and then 4 or more clones having similar sequences are selected while paying attention on PCR error, so that they are determined to be correct sequences.

(2) Construction of scFv Against Mortalin and Expression Plasmid Vector therefor Through the use of the cDNA of the antibody obtained from such hybridoma producing a monoclonal antibody against mortalin, the gene of a single-chain antibody (scFv) is constructed and then the scFv gene is cloned into *Escherichia coli* expression plasmid vector pET-27b(+) containing the PelB sequence. Specifically (FIG. 3), first, the VL gene is amplified using a primer set of Primer1 and Primer2 and the VH gene is amplified using a primer set of Primer3 and Primer4. Here, Primer2 contains a polypeptide sequence that links VL and VH. Moreover, each amplification product is designed so that the C-terminal side of VL and the N-terminal side of VH have a homologous sequence. In Primer4, a nucleotide sequence encoding a FLAG tag is inserted, so that the FLAG tag is added on the C-terminal side of VH, with an enterokinase recognition sequence between the C-terminus and the FLAG tag. Each PCR product is further subjected to PCR using a primer set of Primer1 and Primer4, so that a full-length scFv gene is prepared. Its DNA fragment is cloned into a pET-27b(+) plasmid vector (Novagen) (pET27-mot).

*Escherichia coli* is transformed with pET27-mot and then cultured, followed by expression induction using IPTG A protein in a periplasmic fraction is extracted from the cells by an osmotic shock method and then the resultant is purified, so that mortalin scFv is obtained.

(3) Verification of the Functions of Mortalin scFv by ELISA

Whether or not the thus purified scFv binds to mortalin as an antigen is verified by ELISA. Comparison of dissociation constants is made with respect to the monoclonal antibody based on which scFV is prepared.

(4) Epitope Mapping

Full-length mortalin and the sequences of deletion mutant proteins of mortalin are expressed in *Escherichia coli*. The resultants are purified and then used for BIACORE and ELISA experiments.

Intensity of binding between each protein and each anti-mortalin antibody having or not having the capability of being internalized intracellularly is determined by BIACORE (a method for determining intermolecular interaction using surface plasmon resonance (SPR)).

Next, the degree of binding of each protein to each anti-mortalin antibody is measured by ELISA. Taken together with the results of BIACORE, the position of an epitope in a mortalin sequence, which is recognized by a paratope of an anti-mortalin antibody having or not having the capability of being internalized intracellularly and the epitope sequence are determined.

(5) Detection of Mortalin by Western Blotting using scFv

ScFv capable of specifically recognizing mortalin can be applicable to general molecular biological techniques using a specific antibody. Whether or not scFv against mortalin, which is conveniently expressed in large amounts in *Escherichia coli* and then purified, is immunologically applicable as a specific probe for Western blotting is examined.

(6) Examination of Possible Application of scFv to Immunoprecipitation Experiments for Mortalin ScFv capable of specifically recognizing mortalin can be applicable to general molecular biological techniques using a specific antibody. Whether or not scFv against mortalin, which is conveniently expressed in large amounts in *Escherichia coli* and then purified, is immunologically applicable as a specific antigen-binding protein for immunoprecipitation experiments is examined.

The present invention will be described in more detail below with reference to the following examples. However, the present invention is not limited thereto.

Anti-mortalin monoclonal antibodies (37-1, 37-6, 38-5, 71-1, and 96-5) having the cellular internalizing function that were used in the present invention, had been obtained from hybridomas (No. 37, No. 38, No. 71, and No. 96) and are all described in International Patent Publication WO2006/022344 A1 and JP Patent Publication (Kokai) No. 2006-89471 A. The clone (No. 52) producing an anti-mortalin monoclonal antibody (52-3) that is not internalized intracellularly is similarly described in this patent documents. In addition, the clone (37-6) producing an anti-mortalin 2 monoclonal antibody with the highest efficiency of intracellular internalization was deposited with the International Patent Organism Depositary, National Institute of Advanced Industrial Science and Technology under Accession No. FERM ABP-10408 (Date of deposition: Aug. 23, 2005).

Examples

Example 1

Sequencing of Variable Regions 1.1. Isolation of Total RNA

Among anti-mortalin antibodies, hybridomas producing monoclonal antibodies (37-1, 37-6, 38-5, 96-5, and 71-1) having a internalizing function into cancer cells and hybridomas producing monoclonal antibodies not having such internalizing function were separately cultured at a cell concentration of 1×10$^6$ cells/mL or less (approximately 10 mL). Cells were recovered and then stored at −20° C. until RNA extraction. Cells were thawed on ice, RNA extraction was carried out using an RNeasy Mini kit (QIAGEN, cat.No. 74104), and then each total RNA was prepared.

1.2. 1st strand cDNA Synthesis

1st strand cDNA synthesis was carried out using SMART RACE cDNA Amplification (Clontech, cat.No. 634914), RNA (1 µg) obtained in the above section 1. as a template, and 5'CDS primers.

1.3. 5'-RACE

Touch-down PCR was carried out using an Advantage 2 PCR Kit (Clontech, cat. No. K1910-y) included in SMART RACE cDNA Amplification and 2.5 µL of 1st strand cDNA obtained in the above section 2. as a template. Gene specific primers used herein were designed for the 5' of the H-chain and L-chain constant regions, respectively, followed by selection based on the antibody subtype. Primer sequences are as shown below.

```
H chain
MHC-IgG1
                                  (SEQ ID NO: 36)
GGGCCAGTGGATAGACAGATG MHC-IgG2a
                                  (SEQ ID NO: 40)
CAGGGGCCAGTGGATAGACCGATG MHC-IgG2b
                                  (SEQ ID NO: 40)
CAGGGGCCAGTGGATAGACTGATG MHC-IgG3
                                  (SEQ ID NO: 39)
CAGGGACCAAGGGATAGACAG L chain
MLC-kappa
                                 (SEQ ID NO: 176)
GCTCACTGGATGGTGGGAAGATG
```

1.4. Cloning of RACE Product

A RACE product was subjected to agarose gel electrophoresis, a target band was excised, and then the resultant was subjected to gel extraction (QIAGEN). After ligated to a pGEM-T Easy Vector (Promega, cat. No. A1360), the resultant was subjected to TA cloning.

1.5. Sequencing

Colony PCR was carried out using vector primers. Clones in which a target gene had been inserted were selected. DNA preparation was carried out for 6 or more clones for determination of one sequence. Sequencing was carried out using the vector primers. Pseudo sequences from the hybridomas or sequences containing termination codons in the middle of the sequences were removed. Four (4) or more clones having the similar sequences were selected while paying attention on PCR error and then determined as correct sequences. These steps were applied to each antibody. FIG. 1 shows the amino acid sequences of the L-chain and H-chain variable regions of each antibody.

As shown in the sequence comparison of L-chain variable regions in FIG. 1, all the 4 types of the variable regions of the antibodies having the capability of being internalized intracellularly have almost the same sequence. In particular, CDRs thereof involved in binding with mortalin are completely identical to each other. On the other hand, when compared with the variable regions of the antibodies not having the capability of being internalized intracellularly, no differences were observed between the FR3 and FR4 regions, but the CDR regions were significantly different, as were both the signal peptide and FR1 regions.

It was discovered that the amino acid sequences of all of variable regions differed significantly depending on the presence or the absence of the capability of being internalized intracellularly. Thus, it can be sufficiently expected that an antibody retains activity similar to that of the original full-length anti-mortalin monoclonal antibody, as long as it maintains an L-chain variable region and an H-chain variable region (for example, in the case of a single-chain antibody (scFv) prepared by linking the two with a linker region having an appropriate length). Since CDRs have their own unique sequences, epitope sequences (to be recognized by paratopes formed by these CDRs) may be highly likely to differ from each other.

Example 2

Construction of scFv Against Mortalin and Expression Plasmid Vector therefor 2.1. Vector Design The gene of a single-chain antibody (single chain Fv, scFv) was constructed using cDNA of the antibody obtained from the hybridoma producing the monoclonal antibody 37-1 against mortalin. The scFv was prepared by linking antibody heavy-chain and light-chain variable regions (VH and VL) using an appropriate peptide linker, which could be expressed by *Escherichia coli* and purified. The scFv gene was cloned into the recombinant protein expression plasmid vector pET-27b(+) having a PelB sequence that is a signal sequence for transport of the translated protein to the *Escherichia coli* periplasmic region. First, the VL gene was amplified using a primer set of Primer 1 and Primer 2 and the VH gene was amplified using a primer set of Primer 3 and Primer 4. Primer 2 contained a polypeptide sequence for linking VL and VH, and each amplification product was designed so that the C-terminal-side portion of VL and the N-terminal-side portion of VH had a homologous sequence. The polypeptide linker sequence used herein was a linker sequence comprising a non-repetitive sequence used by Luginbuhl et al. (Luginbuhl, B., Kanyo, Z., Jones, R. M., Fletterick, R. J., Prusiner, S. B., Cohen, F. E., Williamson, R. A., Burton, D. R., and Pluckthun, A. (2006) J Mol Biol 363, 75-97). Also, a nucleotide sequence encoding a FLAG tag had been inserted in Primer4. The FLAG tag was added to the C-terminal side of VH, with an enterokinase recognition sequence between the C-terminus and the FLAG tag, (See FIG. 4. The specific amino acid sequences of VH and VL used herein are shown in FIG. 5.)

After purification of each PCR product, they were mixed at a ratio (in the number of molecules) of 1:1, and then PCR was carried out using a primer set of Primer 1 and Primer 4, thereby preparing a full-length scFv gene. The DNA fragment was cloned into a pET-27b(+) plasmid vector (Novagen) using Nco I and Nhe I, so that a protein expression plasmid pET27-mot for expression of scFv against mortalin was constructed (see FIG. 3).

2.2. Expression and Purification of scFv

*Escherichia coli* strain BL21 (DE3) was transformed with pET27-mot and then single clones were cultured in LB medium to approximately 0.4 of turbidity. IPTG was added to 1 mM and then culture was carried out at 27° C. for 12 hours. Subsequently, cells were centrifuged at 6000 g and then recovered. Protein extraction from a periplasmic fraction was carried out by an osmotic shock method (J Biotechnol. 1994 Jul. 29; 36 (1):45-54. Effect of modification of connecting peptide of proinsulin on its export. Kang Y, Yoon J W.). Cells recovered from 50 mL of a culture solution were completely suspended in 30 mL of a solution of 30 mM Tris HCl (pH 8.0) and 20% sucrose and then 60 mL of 0.5 M EDTA was added thereto, followed by 10 minutes of gentle stirring using a magnet stirrer. A supernatant was removed by 10 minutes of centrifugation at 4° C. and 6000 g. The pellet was completely suspended in 30 mL of ice-cooled 5 mM MgSO4, followed by 10 minutes of gentle stirring in ice. A supernatant was recovered by 10 minutes of centrifugation at 4° C. and 6000 g. After addition of 1.5 mL of 500 mM phosphate buffer (pH 8), protein purification was carried out using Talon (Clontech). Talon (200 ml) was added to 30 mL of the solution. After overnight shaking at 4° C., washing was carried out using 20 mM imidazole/PBS. Imidazole/PBS (1 M) was used for elution. For confirmation of the purity of the thus purified scFv, development was carried out by SDS-PAGE and then protein detection was carried out by Coomassie blue staining. Purification of only the target scFv band was confirmed (see FIG. 6).

2.3. Verification of the Functions of Mortalin scFv by ELISA

Whether purified scFv bound to mortalin as an antigen was verified by ELISA. Mortalin (100 ng for each sample) was added to an ELISA plate and then left to stand at room temperature for 2 hours for physical adsorption to the plate. The plate was washed once with washing buffer (PBS/0.2% TritonX100) and then left to stand using a blocking buffer (2% BSA, PBS) for 2 hours at room temperature. After washing once with a washing buffer, diluted scFv was added to the blocking buffer, and then the resultant was left to stand at 4° C. overnight. After washing 3 instances with the washing buffer, a solution of an anti-FLAG antibody (Sigma) diluted 500-fold with a blocking buffer was added. The resultant was left to stand at room temperature for 1 hour, followed by 3 instances of washing with the washing buffer. Similarly, an alkaline phosphatase-modification anti-mouse antibody (PIERCE) diluted 1000 fold was added and then the resultant was left to stand at room temperature for 1 hour, followed by 5 instances of washing with the washing buffer. Subsequently, PNPP (PIERCE) was added and then the resultant was left to stand at room temperature for 30 minutes. Coloring reaction was measured at 405 nM using a plate reader. Simultaneously, non-specific binding of scFv to a plate not coated with mortalin was also measured and the value was subtracted, so that the binding of scFv to mortalin was estimated.

As a result, scFv was found to bind to mortalin at a dissociation constant of approximately 10 nM. Also, when ELISA was similarly carried out using the monoclonal antibody 37-1 based on which scFv had been prepared (such monoclonal antibody 37-1 being used instead of an anti-FLAG antibody), this was found to have a dissociation constant of approximately 0.1 nM.

Example 3

Epitope Mapping 3.1. Expression and Purification of Full-Length Mortalin and Deletion Mutant Protein of Mortalin The full-length sequence of mortalin with an His tag added thereto was cloned into BamH I and Sal I multicloning sites of a pQE30 plasmid vector (QIAGEN) and then expressed by *Escherichia coli*. The pQE30 plasmid vector causes the expression of the protein in which a His tag has been added to the N-terminus of the cloned protein, and the protein can be conveniently purified with Ni-NTA agarose gel. pQE30/full-length mortalin and pQE3Odel-mot plasmid vectors of various types of deletion mutant mortalin shown in FIGS. 8-10 were transformed into *Escherichia coli* M15. Single colonies were cultured using LB medium at 37° C. IPTG (isopropyl-1-thio-β-D-galactopyranoside) was added to 1 mM when the absorbance at 600 nm was approximately 0.4. After 5 hours of further culturing at 37° C., cells were recovered. A pellet was suspended in buffer A (100 mM NaH2PO4, 10 mM Tris-Hcl (pH 8.0), 8 M Urea, 20 mM β-mercaptoethanol, 1% TritonX-100), followed by 1 hour of rotary stirring at room temperature. Subsequently, the resultant was centrifuged at 4° C. and 15000 rpm for 30 minutes, only the supernatant was transferred to another tube, Ni-NTA agarose (SIGMA) was added, and then rotary stirring was carried out at room temperature for 1 hour. Subsequently, Ni-NTA agarose was washed with buffer B (100 mM NaH2PO4, 10 mM Tris-Hcl (pH 6.5), 8 M Urea, 20 mM β-mercaptoethanol), buffer C (100 mM NaH2PO4, 10 mM Tris-Hcl (pH 5.9), 8 M Urea), and then buffer D (100 mM NaH2PO4, 10 mM Tris-Hcl (pH 4.5), 8 M Urea), so that a target protein was eluted in a stepwise manner. The thus eluted proteins were subjected to overnight dialysis using a dialysis membrane (3,500 MW Piarce) and PBS and then used for BIACORE and ELISA experiments.

3.2. Biacore Analysis

Binding of each protein to each anti-mortalin antibody was verified using BIACORE2000 and software attached thereto. Full-length mortalin and deletion mutants of mortalin have an His tag, so that they bind to BIACORE sensor chips on which NTA has been immobilized. Each protein was adjusted to 200 nM using a running buffer (0.01 M HEPES, 0.15 M NaCl, 50 μM EDTA, 0.005% Surfactant P20, pH 7.4) and then 20 μL of the solution was immobilized on a sensor chip at 2 μL/min. Subsequently, anti-mortalin antibodies (38-4, 52-3, and 96-5) were each adjusted to 400 nM using the running buffer, 40 μL of the solution was poured onto the sensor chip at 20 μL/min, and then interaction was detected. Anti-mortalin antibody solutions diluted stepwise (500 nM, 250 nM, 125 nM, 62.5 nM, and 31.25 nM) were used to detect interaction and then to calculate the Kd values (FIG. 8).

3.3. Epitope Mapping of Anti-Mortalin Antibodies by ELISA

Whether the purified deletion mutant proteins of mortalin bound to anti-mortalin antibodies was verified by ELISA. The deletion mutant proteins of mortalin (100 ng each) were added onto ELISA plates, left to stand at room temperature for 2 hours for physical adsorption to the plates. The plates were washed once with a washing buffer (PBS/0.2% TritonX100) and then left to stand using a blocking buffer (2% BSA, PBS) for 2 hours at room temperature. After washing once with a washing buffer, the anti-mortalin antibodies (38-4, 52-3, and 96-5) diluted 1000 fold were each added to a blocking buffer and then the resultant was left to stand at 4° C. overnight. After washing 3 instances with a washing buffer, an alkaline phosphatase-modification anti-mouse antibody (PIERCE) diluted 1000 fold was added. The resultant was left to stand at room temperature for 1 hour and then washed 5 instances with the washing buffer. Subsequently, PNPP (PIERCE) was added, the resultant was left to stand at room temperature for 30 minutes, and then coloring reaction at 405 nm was measured using a plate reader. Simultaneously, non-specific binding of each anti-mortalin antibody to a plate to which no deletion proteins of mortalin had adsorbed was measured, the value was subtracted as negative control (FIG. 9).

As a result of comprehensive determination of the results of BIACOA and ELISA in 3.1 to 3.3 above, it was considered that: the epitope of the 38-4 antibody or the 96-5 antibody having the capability of being internalized intracellularly was located within the range of amino acid residues 310-410 of mortalin; and that the epitope of the 52-3 antibody not having the capability of being internalized intracellularly was located within the range of amino acid residues 403-435.

These results demonstrated that an antibody having the capability of being internalized intracellularly and an antibody not having such capability recognize different epitope regions in the full-length mortalin. The results particularly demonstrated that an anti-mortalin antibody having the capability of being internalized intracellularly is internalized into cancer cells via the epitope of mortalin existing on the cancer cell surfaces. Specifically, delivery of an anti-mortalin antibody, an anticancer agent bound thereto, or a drug for testing into cancer cells can be accelerated by expressing such epitope on cancer cell surfaces in large amounts through the use of an expression vector comprising a nucleic acid encoding the epitope.

Example 4

Further ELISA Analysis

To further narrow down a particular region containing an epitope sequence in mortalin, which is recognized by an antibody having the capability of being internalized intracellularly, a portion of the amino acid sequence of mortalin, ranging from position 310 to position 410, was divided into three portions and then ELISA analysis was carried out using the 38-4 antibody (internalization antibody) and the 52-3 antibody (non-internalization antibody). Experimental procedures conducted herein are similar to those described in 3.3.

As a result, the epitope to be recognized by the anti-mortalin antibody having the capability of being internalized intracellularly of the present invention was considered to be present in the region (SEQ ID NO: 56) ranging from position 381 to position 410 of the amino acid sequence (common in both human and mouse mortalin 2) of mortalin, in the amino acid sequence of mortalin.

Example 5

Eighty nine (89) peptides (15 amino acids each) which were designed to each be shifted by one amino acid on the amino acid sequence ranging from position 348 to position 450 of human mortalin containing the amino acid sequence (SEQ ID NO: 56) ranging from the above position 381 to position 410, were chemically synthesized. Epitope mapping (RepliTope mapping) analysis was then carried out on them using a Tecon HS400 microarray analysis station (FIG. 14).

Background measurement was carried out for each microarray using an Axon Genepix scanner, so that it was confirmed that no signals were detected. All microarrays were treated using a blocking buffer (Pierce, Puperblock TBS #37536).

As anti-mortalin monoclonal antibodies having the cellular internalizing function, two antibodies 37-6 and 38-4 were prepared. Antibody 53-3 that is an anti-mortalin antibody not having the cellular internalizing function was prepared for comparison. Each antibody (30 μg/mL, 200 μL) diluted with a blocking buffer was applied to microarrays and then incubated. After the microarrays were washed 3 instances with a TBS buffer containing 0.1% T20, a fluorescence-labeled secondary antibody (1 μg/mL, anti-mouse-Dylight 649; Pierce #35515) was applied thereto and then incubated. Similarly, a control array subjected to incubation with only the secondary antibody was also treated so as to confirm no detected signals.

Microarrays were washed with a TBS buffer and then dried with nitrogen gas. With the use of Axon Genepix 4000B scanner, appropriate wavelength setting was carried out and then the microarrays were scanned using a spot recognition software package GenepixPro 6.0. The average signal intensity was calculated from the 3 subarrays on each microarray image and then data analysis was carried out. Results are shown in FIGS. 15, 16, and 17, respectively.

It was discovered among these peptides that peptide sequences (SEQ ID NOS: 67-76) were present in succession, such sequences exerted strong specific binding with respect to the anti-mortalin antibodies (antibody 37-6 and antibody 38-4) having the internalizing function. Accordingly, the sequence of 6 amino acids, "LFGRAP (SEQ ID NO: 66)," common among these sequences was confirmed to be a continuous epitope (FIG. 18). Furthermore, internalization antibody-specific binding sequences could be determined (SEQ ID NOS: 77-82).

Blast search for "LFGRAP (SEQ ID NO: 66)" yielded no results other than mortalin. Therefore, it was demonstrated that the sequence is an unique sequence that is present only in mortalin.

Example 6

Detection of Mortalin by Western Blotting using scFv (FIG. 10)

A cell extract was prepared using an NP40 lysis buffer (50 mM HEPES, pH 7.5, 150 mM NaCl, 100 mM NaF, 1 mM PMSF, 0.5% triton-X100, 0.5% NP-40, 1 mM DTT, protease inhibitors cocktail, Roche) and then centrifuged at 13000 rpm and 4° C. for 10 minutes. The supernatant was then separated. Protein concentration was measured by Bradford assay. Ten (10) μg of the protein was mixed with an SDS sample buffer, denaturation was carried out at 96° C. for 5 minutes, and then SDS-PAGE was carried out. The protein was transferred to an Immobilon-P membrane (Millipore) using a semi dry blotting apparatus (Atto, Japan). After 30 minutes of blocking using a TBS-T buffer containing 5% skim milk suspended therein, scFV (5-10 μg/ml) was added and then the solution was left to stand at 4° C. overnight. Subsequently, after washing with a TBS-T buffer, a polyclonal anti-His antibody was added and then the mixture was left to stand at room temperature for 1 hour, followed by washing with the TBS-T buffer. Similarly, an HRP-conjugated secondary anti-rabbit antibody was added and then the mixture was left to stand at room temperature for 30 minutes. After 3 instances of washing with the TBS-T buffer and then washing once with the TBS buffer, bands were detected by a fluorescence detection method using an ECL (Amersham Biosciences) reagent and an Lumino Image Analyzer (LAS3000-mini, FujiFilm). As a result, specific detection of the band of mortalin was possible.

Example 7

Detection of Mortalin by Immunoprecipitation (FIG. 11)

After preparation of a cell extract by the above method, 300 μg of a cell protein was mixed with 10 μg of scFv and then the mixture was left to stand at 4° C. for 3 to 4 hours. Subsequently, an anti-His polyclonal antibody was added and then the resultant was left to stand at 4° C. overnight. Immunocomplexes were pelleted after incubation and mixing with Protein A-agarose, followed by gentle stirring by turning the mixture upside down and rightside up repeatedly for 30 minutes at 4° C. The resultant was centrifuged at 10,000 g for 2 minutes, a protein complex was precipitated, and then the pellets were washed with an NP40 buffer. Subsequently, the thus precipitated protein was detected by Western blotting using an anti-mortalin antibody. As a result, it was demonstrated that scFv binds to mortalin even in a cell solution and can be precipitated and purified in the form of complex.

Based on these results, it was proven that the scFv newly designed based on the results of paratope analysis binds to the mortalin protein.

This also suggests that paratopes formed mainly of CDRs in antibody variable regions of antibodies having the capability of being internalized intracellularly and antibodies not having such function recognize epitopes at different positions of mortalin existing on cancer cell surfaces. In view of the fact that, as described above, antibodies having the capability of being internalized intracellularly and antibodies not having such function possess their own unique CDR sequences, it was strongly suggested that these CDR sequences play extremely important roles in anti-mortalin antibodies' capability of being internalized into cancer cells.

Reference Example 1

Synthesis of Polyethylenimine-Anti-Mortalin Antibody (PEI-imot Ab Conjugate) (FIG. 19)

S1.1 Activation of Polyethylenimine

A crosslinker (0.2 mg) (EMCS) dissolved in dimethyl sulfoxide (DMSO) was added to 0.5 mg of polyethylenimine (dissolved in PBS to 2 mg/mL), followed by 1 hour of reaction by rotating and stirring the mixture at 25° C. To remove the crosslinker that had remained unreacted, purification was carried out using a 10-kDa exclusion column (VIVASPIN 10KMW, Sartrius).

S1.2. Reduction of Antibody

Dithiothreitol (DTT) was added to 1 mg of the anti-mortalin antibody having the internalizing function (detailed information of the anti-mortalin antibody #37-6; i-mot Ab is given in Reference example 6, which is simply referred to as an anti-mortalin antibody in the Reference examples below) to a final concentration of 20 mM, followed by 30 minutes of reaction at room temperature. DTT was removed using a demineralization column (PD-10, GE Healthcare). The antibody was recovered using a buffer (50 mM MOPS, 2 mM EDTA, pH 6.0).

S1.3. Binding of Polyethylenimine with Reduced Antibody

Polyethylenimine activated by the crosslinker (EMCS) was added to the reduced antibody, followed by 1 hour of reaction while rotating and stirring the mixture at 25° C. After purification using a cation exchange column (HiTrap SP HP, GE Healthcare), purification was further carried out using a 100-kDa exclusion column (Microcon YM-100, Millipore), and then recovery was carried out with 0.1 M MOPS and 150 mM NaCl (pH 7.4).

Reference Example 2

Polyplex Formation Using Synthesized PEI-imotAb Conjugate and Plasmid DNA

It was confirmed (FIG. 20) by gel retardation assay that the synthesized PEI-imot Ab interacted with DNA, so as to form a polyplex. PEI-imotAb and plasmid DNA were mixed, so that the N/P ratios were 0, 1, 2, 5, 7.5, and 10. The mixtures were left to stand at room temperature for 30 minutes and then 0.8% agarose gel electrophoresis was carried out. It was revealed that at the N/P ratio of 2 or higher, PEI-imotAb completely interacted with plasmid DNA.

Reference Example 3

Introduction of Plasmid DNA Using the PEI-imotAb Conjugate

DMEM (95 μL) was added to 1 μg of plasmid DNA encoding DsRed2 or Renilla luciferase and then they were mixed well by pipetting. The PEI-imotAb conjugate was added to an N/P ratio of 7.5 (adjustment was performed so that polyethylenimine had a concentration of 0.5 mg/mL and then 4.05 μL of the solution was added to 1 μg of DNA). They were mixed well by pipetting and then the mixture was left to stand at room temperature for 30 minutes.

At 24 hours before transfection, U2OS cells (the cell line expressing mortalin at a high level) were seeded over a 12-well plate to $2 \times 10^5$ cells/well. The medium was exchanged with a new medium immediately before transfection and then a PEI-imotAb/DNA conjugate was added. After 2 hours of culturing at 37° C., the medium was exchanged with a new medium and then the cells were further cultured for 48 hours at 37° C.

After 48 hours, fluorescence of DsRed2 was observed via fluorescence microscopy (FIG. 21). Also, cells transfected with Renilla luciferase were subjected to measurement of gene transfer efficiency and expression efficiency using a Luciferase assay kit (Promega) (FIG. 22). For luciferase activity, RLU (relative light unit/second) was measured using a luminometer (Lumat LB9501). RLU was corrected using a protein level measured using the protein assay kit (Bio-Rad), and such measurement represented gene transfer efficiency and expression efficiency as normalized luciferase activity. As controls, PEI-EMCS prepared by binding a crosslinker to polyethylenimine and a PEI-control Ab conjugate prepared by binding bovine IgG recovered from bovine serum to the same were used. Gene transfer efficiency and expression efficiency resulting from the use of a PEI-imot Ab/DNA polyplex was found to increase at a level higher than that of the control PEI-EMCS/DNA polyplex. Moreover, since no such increase was observed in the case of the control conjugate prepared by binding with the bovine antibody, it can be said that gene transfer efficiency and expression efficiency increased in an anti-mortalin-antibody-dependent manner.

Reference Example 4

Cancer Cell-Specific Gene Transfer

Furthermore, a general U2OS cell line and an U2OS mot cell line overexpressing mortalin were transfected with the PEI-imot Ab/DNA polyplex. In the case of the PEI-EMCS/DNA poleplex, no difference in gene transfer efficiency was found between the U2OS cell line and the U2OS mot cell line. However, in the case of the PEI-imot Ab/DNA polyplex, gene transfer efficiency increased to a greater extent in the cell line overexpressing mortalin (FIG. 23). The results strongly suggest that gene transfer takes place in an anti-mortalin antibody-dependent manner.

Also, the anti-mortalin antibody is internalized specifically into cancer cells. Hence, gene transfer was carried out using cancer cells (U2OS, HeLa, SKBR3) and normal cells (TIG-1) and the PEI-imot Ab/DNA polyplex. Normal cells exhibited gene transfer efficiency to a level equivalent to that of the control PEI-EMCS/DNA polyplex. However, all cancer cell lines exhibited increased gene transfer efficiency and increased expression efficiency when the PEI-imot Ab/DNA polyplex had been used (FIG. 24).

Reference Example 5

Internalization of Anti-Mortalin Antibody into Various Cancer Cells

To confirm that the anti-mortalin antibody of the present invention undergoes internalization into every type of cancer cell, an experiment of internalization into typical cancer cells including bone cancer cells (U2OS and Saos-2), breast cancer cells (MCF7, SKBR3, and T47D), fibrosarcoma cells (HT1080), cervical cancer cells (HeLa), lung cancer cells (A549), glioblastoma cells (A172), urothelial cancer cells (J82), liver cancer cells (HepG2), and human embryonal cancer cells (NEC8) was conducted using an anti-mortalin polyclonal antibody.

Specifically, the anti-mortalin polyclonal antibody was modified according to manuals with Q dots (Invitrogen) emitting fluorescence characteristic of the effects of quantum dots. The thus obtained conjugate (Qd-i-mot Pab) of Qd and the anti-mortalin polyclonal antibody was added to media for culturing the above cancer cells. The media were removed after 24 hours. The resultants were washed 3 instances using a PBS buffer and then fixed with a methanol/acetone (1:1) solution. After fixing, cells were observed via fluorescence microscopy (Axiovert 200 M, Carl Zeiss) such that intracellular internalization of Qd-i-mot Pab was observed.

As a result, it was confirmed by observation via the fluorescence microscopy that in all cancer cells, the conjugate of the anti-mortalin antibody and quantum dots (Qdots) was transferred into the cells.

Among the aforementioned cancer cells, the results for A549 (lung cancer cells), A172 (glioblastoma cells), J82 (urothelial cancer cells), and NEC8 (human embryonal cancer cells) are shown in FIG. 25.

INDUSTRIAL APPLICABILITY

The paratope of the present invention is useful as an anti-cancer agent suppressing mortalin activity within cancer cells or on cancer cell surfaces or is useful as a carrier for the delivery of therapeutic drugs or drugs for detection into cancer cells.

Also, the epitopes of the present invention are useful in identification and/or evaluation methods for anti-mortalin antibodies. In particular, regarding an epitope to be recognized by an anti-mortalin antibody having the internalizing function, an expression vector comprising a nucleic acid that encodes the epitope can be used as an agent for accelerating internalization (into cancer cells) of an anti-mortalin antibody and a drug (such as an anticancer agent, a detection reagent, and the like) bound to an anti-mortalin antibody.

The invention claimed is:

1. An H-chain variable region of a recombinant anti-mortalin antibody which specifically recognizes mortalin 2 and has a cellular internalizing function, wherein the CDR1 consists of the sequence "SYWMH (SEQ ID NO: 14)," CDR2 consists of the sequence "EIDPSDSYTKYNQKFKG (SEQ ID NO: 15)" or "EIDPSDSYTDYNQNFKG (SEQ ID NO:18)," and CDR3 consists of the sequence "GDY (SEQ ID NO: 16)."

2. The H-chain variable region of the recombinant anti-mortalin antibody according to claim 1, which is defined by (i) of claim 1 and consists of the following amino acid sequence (a) or (b):
    (a) the amino acid sequence shown in SEQ ID NO: 17, 19, or 20; or
    (b) an amino acid sequence derived from the amino acid sequence shown in SEQ ID NO: 17, 19, or 20 by deletion, substitution, and/or addition of one or several amino acids in a signal sequence and/or a framework sequence, wherein said signal sequence ranges from position 1 to 19 of SEQ ID NOs: 17, 19, and 20.

3. An anti-mortalin single-chain antibody specifically recognizing mortalin 2, which comprises an L-chain variable region of an anti-mortalin antibody and an H-chain variable region of an anti-mortalin antibody, wherein the L-chain variable region consists of one of the following amino acid sequences (a) or (b):
    (a) the amino acid sequence shown in SEQ ID NO: 4 or 5; or
    (b) an amino acid sequence derived from the amino acid sequence shown in SEQ ID NO:4 or 5 by deletion, substitution, and/or addition of one or several amino acids in a signal sequence and/or a framework sequence, wherein said signal sequence ranges from position 1 to 20 of SEQ ID NOs: 4 and 5;

wherein the H-chain variable region consists of one of the following amino acid sequences (c) or (d):

(c) the amino acid sequence shown in SEQ ID NO: 17, 19, or 20; or (d) an amino acid sequence derived from the amino acid sequence shown in SEQ ID NO: 17, 19, or 20 by deletion, substitution, and/or addition of amino acid in a signal sequence and/or a framework sequence, wherein said signal sequence ranges from position 1 to 19 of SEQ ID NO: 17, 19, and 20.

4. An anticancer agent which suppresses mortalin activity within a cancer cell, comprising, as an active ingredient, the anti-mortalin single-chain antibody according to claim 3 or a conjugate of said single-chain antibody with a therapeutic compound bound thereto.

5. A reagent for detection or identification of a cancer cell, comprising the anti-mortalin single-chain antibody according to claim 3 bound to a fluorescent labeling compound.

* * * * *